US009567598B2

(12) United States Patent
Malcuit et al.

(10) Patent No.: US 9,567,598 B2
(45) **Date of Patent: *Feb. 14, 2017**

(54) PLANT PLASTID TRANSFORMATION METHOD

(75) Inventors: Isabelle Malcuit, London (GB); Alexander Sorokin, London (GB)

(73) Assignee: Algentech SAS, Envry (FR)

( * ) Notice: Subject to any disclaimer, the term of this patent is extended or adjusted under 35 U.S.C. 154(b) by 897 days.

This patent is subject to a terminal disclaimer.

(21) Appl. No.: 13/131,004

(22) PCT Filed: Nov. 25, 2009

(86) PCT No.: PCT/GB2009/002754
§ 371 (c)(1), (2), (4) Date: Sep. 9, 2011

(87) PCT Pub. No.: WO2010/061186
PCT Pub. Date: Jun. 3, 2010

(65) Prior Publication Data

US 2011/0321187 A1 Dec. 29, 2011

(30) Foreign Application Priority Data

Nov. 25, 2008 (GB) .................................. 0821516.2

(51) Int. Cl.

| | |
|---|---|
| ***C12N 15/09*** | (2006.01) |
| ***C12N 15/11*** | (2006.01) |
| ***C12N 15/63*** | (2006.01) |
| ***C12N 15/62*** | (2006.01) |
| ***C12N 15/82*** | (2006.01) |

(52) U.S. Cl.
CPC ....... *C12N 15/8214* (2013.01); *C12N 15/8216* (2013.01); *C12N 15/8217* (2013.01); *C12N 15/8257* (2013.01)

(58) Field of Classification Search
None
See application file for complete search history.

(56) References Cited

U.S. PATENT DOCUMENTS

| | | | | |
|---|---|---|---|---|
| 2,561,330 | A * | 7/1951 | Ayers | 554/198 |
| 2003/0104352 | A1* | 6/2003 | Lambowitz et al. | 435/4 |
| 2004/0142476 | A1* | 7/2004 | Evans et al. | 435/468 |
| 2006/0253916 | A1 | 11/2006 | Biesgen | |
| 2008/0222750 | A1 | 9/2008 | Khan | |
| 2009/0178161 | A1 | 7/2009 | Arar et al. | |

FOREIGN PATENT DOCUMENTS

| | | | |
|---|---|---|---|
| GB | 2 449 466 | A | 11/2008 |
| WO | 02/079409 | A2 | 10/2002 |
| WO | 03/054189 | A2 | 7/2003 |
| WO | 2004/040973 | A2 | 5/2004 |
| WO | 2006/056701 | A1 | 6/2006 |
| WO | 2008/142411 | A1 | 11/2008 |

OTHER PUBLICATIONS

Maliga (Genomics of Chloroplasts and Mitochondria Advances in Photosynthesis and Respiration vol. 35, pp. 393-414, 2012).*
Andres et al (Physiol. Plant. 129, pp. 14-22, 2007).*
Zoschke et al (PNAS, 2010, 107(7), pp. 3245-3250).*
Asakura et al (The Plant Cell, 2007, 19(12), pp. 3864-3875).*
Odom et al (The Plant Journal, 2008, 53, pp. 842-853).*
Deshpande et al (Curr. Genet. 28(2), pp. 122-127, 1995).*
Flores et al (FEBS Letters, 567(1), pp. 42-48, 2004).*
Ruf et al (Nature Biotechnology, 19, pp. 870-875, 2001).*
Lutz, Kerry Ann, et al., "A Guide to Choosing Vectors for Transformation of the Plastid Genome of Higher Plants", Plant Physiology, Dec. 2007, pp. 1201-1210, vol. 145, No. 4.
Mcbride, Kevin E., et al., "Controlled expression of plastid transgenes in plants based on a nuclear DNA-encoded and plastid-targeted T7 RNA polymerase", Proc. Natl. Acad. Sci., Jul. 1994, pp. 7301-7305, vol. 91.

* cited by examiner

*Primary Examiner* — Anne Kubelik
*Assistant Examiner* — Stephen Uyeno
(74) *Attorney, Agent, or Firm* — Sughrue Mion, PLLC

(57) ABSTRACT

Method for heterologous protein production in plant cell plastids comprising introducing into plant cells nucleic acid components that encode heterologous proteins under the control of promoters operative in plastids, vectors, host cells, plants and uses thereof.

11 Claims, 6 Drawing Sheets

PLANT PLASTID TRANSFORMATION METHOD

CROSS REFERENCE TO RELATED APPLICATIONS

Figure 1:
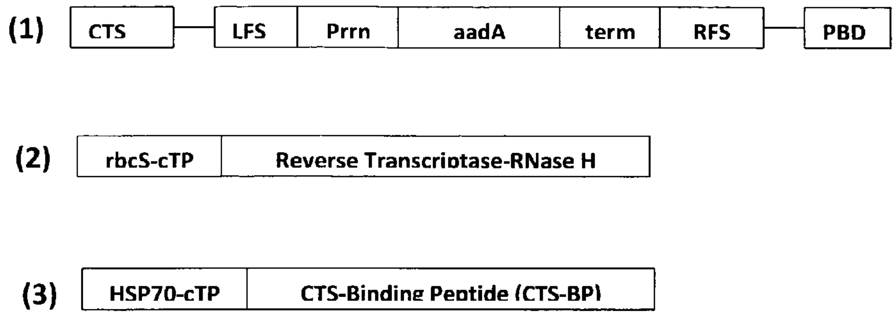

This application is a National Stage of International Application No. PCT/GB2009/002754 filed Nov. 25, 2009, claiming priority based on British Patent Application No. 0821516.2 filed Nov. 25, 2008, the contents of all of which are incorporated herein by reference in their entirety.

The present invention relates to a method for producing heterologous or exogenous RNA species in plant cell material such as genetically transformed plant cells in culture, plant tissue and plants derived from genetically transformed plant cells. In particular, the method relates to a more efficient method for producing RNA species and/or heterologous or exogenous proteins in plastids comprised in plant cell material, the genetic material required therefore, such as DNA and RNA, vectors, host cells, methods of introduction of genetic material into plant cells, plant cells comprising genetically modified plastids, and uses thereof.

A disadvantage of prior art plant plastid transformation methods is that the transformation efficiency in terms of numbers of transformed plastids per cell tends to be low. A further disadvantage of prior art methods is that the delivery of genetic information into the plastid tends to be erratic in the sense that the delivery mechanisms employed rely on chance for the successful delivery of genetic information, such as RNA, into the plastid genome. Prior art methods do not rely on efficient endogenous cellular processes for the transfer of RNA into the plastid genome, subsequent reverse transcription and recombination of it within the plastid genome, and where desired, followed by expression of protein of interest therefrom. As such, prior art processes for genetically modifying plastids appear inefficient. These and other disadvantages of prior art plastid transformation technology will become apparent from the foregoing description.

The present inventors have found that by using or adapting endogenous cellular processes for the transfer of polynucleotide sequences, such as RNAs, from the cytoplasm to the plastid in the plant cell, polynucleotide sequences derived from nuclear transformation of the nucleus of a plant cell can be efficiently transferred or targeted to the plastid genome within a plant cell that is so transformed, and expressed more efficiently in the plastid as described herein. Furthermore, it is apparent that once the plastid is transformed with sequences of the invention, it is not necessary for the nuclear encoded trangenes that are required for the initial transformation of the plastid to remain in the nuclear genome. As a consequence, the nuclear encoded transgenes can be removed through deliberate or natural segregation in subsequent generations of plants. For the purposes of the present invention the terms “plastid” and “plastids” and “plastid population” are used interchangeably, as are the terms “plant cell” and “plant cells”, unless context demands otherwise. By employing or adapting endogenous cellular processes for the transfer of RNA derived from polynucleotide sequences introduced to the nucleus to the plastid genome, as described herein, the method of the invention is considered to be unique over prior art methods for the generation of plant cells or plants possessing genetically modified plastids. The plastid population of the plant cell is constantly bombarded by RNA that is derived from the nucleus of the cell, which is carried over the plastid membrane and into the plastid where it is reverse transcribed, integrated into the genome and then transcribed, resulting in the generation of RNA from which proteins of interest may be expressed.

There exists a need for a more efficient plastid transformation method for the production of RNAs, and where required, proteins of interest in the plastids of transformed plant cells and plant tissue derived therefrom.

The basis for the present invention, which does not appear to have been realised in the prior art, is the supply of a plant plastid transformation unit comprising nucleic acid sequences that encode: i) a plant plastid transformation unit (PTU); ii) a reverse transcriptase fused to a plant-derived chloroplast transit peptide sequence; and iii) an RNA binding protein fused to a plant plastid transit peptide. Such plastid fusion systems do not appear to have been described or alluded to in the prior art. Further simplified modifications of this kind of plant plastid transformation unit include those that comprise nucleic acid sequences that encode i) a plant plastid transformation unit [PTU, for example, a chloroplast transformation unit (CTU)]; a plant plastid translocation sequence (PPS-5'), for example, a chloroplast translocation sequence (CTS-5'), fused to the 5' end of the PTU; a further plant plastid translocation sequence (PPS-3'), for example a chloroplast translocation sequence (CTS-3') fused to the 3'-end of the CTU; and a primer binding domain designed for reverse transcription in plastids using plastid tRNA-Met, such as chloroplast tRNA-Met (PBD-CHL). By placing the PBD-CHL next to the 3' end of the CTS-3', that is to say, outside of the LtrB intron as depicted in FIG. 3(A), the LtrA protein is able to function as both a translocation protein and as a source of reverse transcriptase. In such a variant, there is no need to introduce a second gene for reverse transcriptase functionality. In a second variant of this system, where the PBD (PBD-CYT) is designed to interact with endogenous cytoplasmic tRNA-Met, the PBD may be located adjacent to the 3'-end of the PTU (or preferably, a CTU) and a plastid translocation sequence, preferably a chloroplast translocation sequence, is fused to it downstream. In this second variant, where a PBD is employed that is able to bind with cytoplasmic tRNA-Met as primer, reverse transcription is initiated by endogenous reverse transcriptase in the cytoplasm using cytoplasmic tRNA-Met. Thus, the second variant of the system does not require the co-delivery of a reverse transcriptase nucleic acid sequence to the plastids, such as chloroplasts. The use of such plastid transformation systems provides for an improved yield of RNA and hence protein of interest from plastid sources than has been hitherto achievable in the prior art.

According to the present invention there is provided a method of transforming a plant cell that comprises:

1) introducing into the said plant cell a nucleic acid sequence that comprises a plant nuclear promoter operably linked to a first nucleic acid sequence that comprises a plastid transgene cassette, a plastid translocation sequence (PTS), and a primer binding domain (PBD);

2) introducing into the said plant cell a second nucleic acid sequence that encodes for a plastid translocation sequence binding protein fused to a first plastid transit peptide (PTSBP-TP) wherein said second nucleic acid sequence is operably linked to a plant nuclear promoter; and 3) introducing into the said plant cell a third nucleic acid sequence that encodes for a reverse transcriptase protein fused to a second plastid transit peptide wherein the third nucleic acid sequence is operably linked to a plant nuclear promoter that drives expression in a plant cell nucleus.

The word “plastid” for the purposes of the present invention encompasses chloroplasts, proplastids, etioplasts, chromoplasts, amyloplasts, leucoplasts and elaioplasts. Preferably, “plastid” refers to chloroplasts. For the purposes of the description, the terms “chloroplast” and “chloroplasts” are used interchangeably unless context demands otherwise, as are the terms “plastid” and “plastids”.

The skilled addressee will appreciate that where there are native proteins present in a plant cell that are capable of binding to a plastid translocation sequence, such as a chloroplast translocation sequence, and which are capable of translocating RNA nucleic acid sequences to the plastid, such as viroid proteins, the method of the invention for transforming a plant cell comprises:

1) introducing into the said plant cell a nucleic acid sequence that comprises a plant nuclear promoter operably linked to a first nucleic acid sequence that comprises a plastid transgene cassette, a plastid translocation sequence (PTS), and a primer binding domain (PBD); and 2) introducing into the said plant cell a second nucleic acid sequence that encodes for a reverse transcriptase protein fused to a second plastid transit peptide wherein the said second nucleic acid sequence is operably linked to a plant nuclear promoter that drives expression in a plant cell nucleus.

In a preferment of the above method, the plastid transgene cassette is a chloroplast transgene cassette, and the plastid translocation sequence (PTS) is a chloroplast translocation sequence (CTS), and the reverse transcriptase protein is a reverse transcriptase from a retrotransposon or a retrovirus which is fused to a chloroplast transit peptide for targeting into the chloroplast.

In a further aspect of the invention there is provided a method of transforming a plant cell that comprises introducing into the plant cell a nucleic acid sequence that comprises a plant nuclear promoter operably linked to a first nucleic acid sequence that comprises a first plastid translocation sequence (PTS-5') fused to the 5'-end of the plastid transgene unit (PTU), a second plastid translocation sequence (PTS-3') fused to the 3' end of the PTU, and a primer binding domain designed for reverse transcription in plastids, using tRNA-Met located within the plastids.

Preferably, the first plastid translocation sequence at the 5'-end is a chloroplast translocation sequence (CTS-5'), that is fused to a the 5'-end of a chloroplast transformation unit (CTU), and a second plastid translocation sequence is fused to the 3'-end of the CTU. Preferably, the second plastid translocation sequence is a chloroplast translocation sequence (CTS-3') that is fused to a primer binding domain that is designed for reverse transcription in chloroplast plastids (PBD-CHL), using tRNA-Met as primer that are located within the chloroplasts. The two plastid translocation sequences may be the same or different depending on design. In this variant reverse transcription can be effected when the PBD is located downstream of the CTU, that is to say 3' to a chloroplast translocation sequence (CTS-3'). Such a combination allows both translocation of the CTU into the chloroplast and reverse transcription of the CTU by the LtrA protein and does not require the co-delivery of a nucleic acid sequence for reverse transcriptase functionality.

In a still further variant of the invention, there is provided a method of transforming a plant cell that comprises introducing into the plant cell a nucleic acid sequence that comprises a plant nuclear promoter operably linked to a first nucleic acid sequence that comprises a first plastid translocation sequence (PTS-5') fused to the 5'-end of the plastid transgene unit (PTU), a second plastid translocation sequence (PTS-3') fused to the 3'-end of a primer binding domain for binding tRNA-Met as primer that uses tRNA-Met that is located within the cytoplasm.

Preferably, the first plastid translocation sequence at the 5'-end is a chloroplast translocation sequence (CTS-5'), that is fused to the 5'-end of a chloroplast transformation unit (CTU). The second plastid translocation sequence is a chloroplast translocation sequence (CTS-3') that is fused to a primer binding domain that is capable of utilising native, endogenous reverse transcriptase located in the cytoplasm (PBD-CYT) for reverse transcription using cytoplasmic tRNA-Met as primer. Again, the two plastid translocation sequences may be the same or different depending on design. In this variant, there is also no need to co-deliver a nucleic acid sequence to the chloroplasts for reverse transcriptase functionality.

As another aspect of the invention there is provided a plant cell obtained by any one of the methods of the invention as described herein above.

In a further aspect of the invention there is provided a method of producing at least a heterologous or exogenous RNA species in a plant that comprises:

1) introducing into a regenerable plant cell a nucleic acid sequence that comprises a plant nuclear promoter operably linked to a first nucleic acid sequence that comprises a plastid transgene cassette, a plastid translocation sequence (PTS), and a primer binding domain (PBD);

2) introducing into the said regenerable plant cell a second nucleic acid sequence that encodes for a plastid translocation sequence binding protein fused to a first plastid transit peptide (PTSBP-TP) wherein said second nucleic acid sequence is operably linked to a plant nuclear promoter; and 3) introducing into the said regenerable plant cell a third nucleic acid sequence that encodes for a reverse transcriptase protein fused to a second plastid transit peptide wherein the third nucleic acid sequence is operably linked to a plant nuclear promoter that drives expression in a plant cell;

4) growing said regenerable plant cell of steps 1) to 3);

5) selecting a plant cell of (4) wherein the transgene comprised within the plastid transgene cassette is integrated into the plastid genome;

6) regenerating a plant from the plant cell of (5); and 7) growing the plant of (6).

Preferably, the plant obtained according to the above method is grown under conditions wherein the said heterologous or exogenous RNA species encoded by the transgene integrated into the plastid is expressed as heterologous or exogenous protein.

Again, and with reference to the method of obtaining a plant above, the skilled addressee will appreciate that where there are native proteins present in a plant cell that are capable of binding to a plastid translocation sequence, such as a chloroplast translocation sequence, and which are capable of translocating RNA nucleic acid sequences to the plastid, such as viroid proteins, step 2) of the said method may be omitted. In such an instance, there is provided a a method of producing at least a heterologous or exogenous RNA species in a plant that comprises:

1) introducing into a regenerable plant cell a nucleic acid sequence that comprises a plant nuclear promoter operably linked to a first nucleic acid sequence that comprises a plastid transgene cassette, a plastid translocation sequence (PTS), and a primer binding domain (PBD);

2) introducing into the said regenerable plant cell a second nucleic acid sequence that encodes for a reverse transcriptase protein fused to a second plastid transit peptide wherein the second nucleic acid sequence is operably linked to a plant nuclear promoter that drives expression in a plant cell;

3) growing said regenerable plant cell of steps 1) and 2);

4) selecting a plant cell of (3) wherein the transgene comprised within the plastid transgene cassette is integrated into the plastid genome;

5) regenerating a plant from the plant cell of (4); and 6) growing the plant of (5).

In a further aspect of the invention there is provided a method of producing at least a heterologous or exogenous RNA species in a plant that comprises:

1) introducing into a regenerable plant cell a nucleic acid sequence that comprises a plant nuclear promoter operably linked to a first nucleic acid sequence that comprises a first plastid translocation sequence (PTS-5') fused to the 5'-end of the plastid transgene unit (PTU), a second plastid translocation sequence (PTS-3') fused to the 3'-end of the PTU, and a primer binding domain designed for reverse transcription in plastids;

2) growing said regenerable plant cell of step 1);

3) selecting a plant cell of (2) wherein the transgene comprised within the plastid transgene cassette is integrated into the plastid genome;

4) regenerating a plant from the plant cell of (3); and 5) growing the plant of (4).

Preferably, the first plastid translocation sequence at the 5'-end is a chloroplast translocation sequence (CTS-5'), that is fused to the 5'-end of a chloroplast transformation unit (CTU), and a second plastid translocation sequence is fused to the 3'-end of the CTU. Preferably, the second plastid translocation sequence is a chloroplast translocation sequence (CTS-3') that is fused to a primer binding domain that is designed for reverse transcription in chloroplast plastids (PBD-CHL), using tRNA-Met as primer that are located within the chloroplasts. The two plastid translocation sequences may be the same or different depending on design.

In a further variant of this aspect of the invention there is provided a method of producing at least a heterologous or exogenous RNA species in a plant that comprises:

1) introducing into a regenerable plant cell a nucleic acid sequence that comprises a plant nuclear promoter operably linked to a first nucleic acid sequence that comprises a first plastid translocation sequence (PTS-5') fused to the 5'-end of the plastid transgene unit (PTU), a second plastid translocation sequence (PTS-3') fused to the 3'-end of a primer binding domain for binding tRNA-Met as primer that uses tRNA-Met that is located within the cytoplasm.

2) growing said regenerable plant cell of step 1);

3) selecting a plant cell of (2) wherein the transgene comprised within the plastid transgene cassette is integrated into the plastid genome;

4) regenerating a plant from the plant cell of (3); and 5) growing the plant of (4).

Preferably, the first plastid translocation sequence at the 5'-end is a chloroplast translocation sequence (CTS-5'), that is fused to the 5'-end of a chloroplast transformation unit (CTU). The second plastid translocation sequence is a chloroplast translocation sequence (CTS-3') that is fused to a primer binding domain that is capable of utilising native, endogenous reverse transcriptase located in the cytoplasm (PBD-CYT) for reverse transcription using cytoplasmic tRNA-Met as primer. Again, the two plastid translocation sequences may be the same or different depending on design.

Naturally, the person skilled in the art will understand that the plant nuclear promoter by being operably linked to the nucleic acid sequences provided for herein drives expression of such sequences in the plant nucleus.

The "plastid transgene cassette" comprises a left flanking sequence (LFS) and a right flanking sequence (RFS) which are used for homologous recombination of the cassette into the plastid genome. In between the LFS and RFS are located at least one plastid specific promoter sequence (such as a chloroplast specific promoter, e.g. Prrn) and at least one plastid specific terminator sequence (such as a chloroplast specific terminator, e.g. 3'UTR sequence of psbA gene from tobacco) which in turn flanks at least one isolated gene or isolated nucleic acid sequence of interest, such as a recombinant DNA sequence (e.g. cDNA) or an introduced native DNA sequence. The LFS and RFS may include the chloroplast specific promoter and terminator sequences, respectively, if for example, the isolated nucleic acid of interest is fused to a native chloroplast nucleic acid of interest. Thus, the promoter and the terminator sequences are not necessarily included within the LFS or RFS, respectively per se, or between the LFS and RFS if a transgene is inserted into the chloroplast genome as a cistron unit or if a transgene is translationally fused to a native gene. In such an instance, when a transgene is fused to a native chloroplast coding sequence it is after the transformation event has taken place that the promoter may be found upstream of the sequence that is homologous to the LFS in the chloroplast genome and is available to drive expression of the gene fused to the transgene of interest. For the purposes of the present invention "transgene" includes isolated nucleic acid sequences that may ultimately give rise to the expression of proteins or peptides of interest in the plastid (e.g. chloroplast) as herein described. Thus, the isolated nucleic acid sequence may be one that gives rise to an RNA sequence of interest which may not encode or give rise to the expression of a translatable product, or the isolated nucleic acid sequence may give rise to an RNA sequence that does encode or give rise to the expression of a translatable product such as a protein or peptide of interest. The person skilled in the art will also appreciate that the transgene that is carried on the isolated nucleic acid may also be designed to give rise to an RNA sequence that gives rise to the expression of a translatable product or products, and untranslatable RNAs. Such RNAs that do not give rise to the expression of proteins may give rise to RNA sequences that contain deletions or other mutations and these may find use as research tools for studying gene function in the plastid, e.g. chloroplast. Where the "transgene" gives rise to the expression of proteins or peptides, suitable transgenes of interest include plant proteins capable of conferring desired traits to plant crops, and pharmaceutical proteins for use in mammals, including man, such as insulin, preproinsulin, proinsulin, glucagon, interferons such as α-interferon, β-interferon, γ-interferon, blood-clotting factors selected from Factor VII, VIII, IX, X, XI, and XII, fertility hormones including luteinising hormone, follicle stimulating hormone growth factors including epidermal growth factor, platelet-derived growth factor, granulocyte colony stimulating factor and the like, prolactin, oxytocin, thyroid stimulating hormone, adrenocorticotropic hormone, calcitonin, parathyroid hormone, somatostatin, erythropoietin (EPO), enzymes such as β-glucocerebrosidase, haemoglobin, serum albumin, collagen, biotic and abiotic stress proteins, such as insecticidal and insect toxic proteins, for example from, or derived from Bacillus thuringiensis, nematicidal proteins, herbicide resistance proteins, (e.g. to glyphosate), salt-tolerance proteins, drought tolerant proteins, nutritional enhancement proteins involved in the biosynthesis of phenolics, starches, sugars, alkaloids, vitamins, and edible vaccines, and the like. Furthermore, the method of the invention can be used for the production of specific monoclonal antibodies or active fragments thereof and of industrial enzymes or active fragments thereof.

All proteins mentioned hereinabove are of the plant and human type. Other proteins that are contemplated for production in the present invention include proteins for use in veterinary care and may correspond to animal homologues of human proteins, such as the human proteins mentioned hereinabove.

In a further aspect of the invention there is provided a plant cell that comprises plastids, such as chloroplasts, that are permanently transformed with an exogenous or a heterologous nucleic acid sequence that encodes for a protein or RNA of interest. Suitable proteins and peptides and nucleic acids of interest are provided herein.

The LFS and RFS may be selected from any nucleotide sequences that may be used for homologous recombination in the plastid. Suitable examples include coding sequences such as the sequence coding for psbA, rbcL genes from chloroplasts.

The plant plastid promoter may be selected from the group consisting of the RNA polymerase promoter, rpo B promoter element, atpB promoter element, the clpP promoter element, the 16S rDNA promoter element, PrbcL, Prps16, the Prrn16, Prrn-62, Pycf2-1577, PatpB-289, Prps2-152, Prps16-107, Pycf1-41, PatpI-207, PclpP-511, PclpP-173, PaccD-129, PaccD-129 promoter of the tobacco accD gene, the PclpP-53 promoter of the clpP gene, the Prrn-62 promoter of the rrn gene, the Prps16-107 promoter of the rps16 gene, the PatpB/E-290 promoter of the tobacco atpB/E gene, and the PrpoB-345 promoter of the rpoB gene. Furthermore, all those promoters which belong to class III (Hajdukiewicz P T J et al. (1997) EMBO J 16:4041-4048) and all fragments of the class II promoters which control the initiation of transcription by NEP may be utilized in the method of the invention. Such promoters or promoter moieties are not generally known to be highly conserved. ATAGAATAAA is given as consensus near the transcription initiation site of NEP promoters (Hajdukiewicz P T J et al (1997) EMBO J 16:4041-4048).

The plant plastid terminator, such as a chloroplast transcription terminator may be selected from any plastid terminator such as psbA, atpA, rbcL 3'-UTR region, and bacterial transcription terminators such as rrnB described by Orosz A., et al., Eur. J. Biochemistry, 2005, Volume 201, Issue 3, pp 653-659.

Naturally, the man skilled in the art will appreciate that other terminator DNA sequences may be present in constructs used in the invention.

The plant plastid (e.g. chloroplast) transgene cassette also comprises a primer binding domain (PBD) that once inside the plastid (e.g. chloroplast) is able to capture tRNAs as primers to form template RNA to initiate reverse transcription of introduced plant chloroplast transformation units of the invention. A suitable tRNA for use in the present invention as a primer is tRNA-fMet which forms a template RNA ready for reverse transcription. The skilled person in the art will appreciate that PBDs are found naturally on retroelements including retroviruses and retrotransposons. PBDs comprise specific RNA domains that anneal to specific sequences on tRNA molecules. The tRNA itself does not serve as a PBD but as a primer for reverse transcription, the template for reverse transcription is the RNA molecule that carries a PBD. Novel PBDs can be readily engineered that can anneal to other tRNAs. PBDs can be designed to bind other types of tRNAs such as, tRNA-lys and tRNA-Met of tobacco and others which are known in the art (http://www.unibayreuth.de/departments/biochemie/trna/).

Certain elements of retroelements such as retroviruses or retrotransposons, have native PBDs possessing conserved domains that anneal with complementary domains from tRNA (usually tRNA-met, or tRNA-trp); because of the conserved structures of all tRNAs (the so-called clover-leaf structure), PBDs can be engineered so that they carry specific domains that will anneal with a tRNA of choice.

A "plastid translocation sequence" (PTS, for example a chloroplast translocation sequence (CTS)) is an RNA sequence that is capable of being bound to a plant PTS binding protein and thereby, the PTS and other RNA sequences that may be associated with it or fused with it can be transported across and into the plastid (e.g. chloroplast). The CTS can be selected from naked RNA viruses, including viral RNAs such as those from positive stranded RNA viruses such as potato virus X (PVX), tobacco mosaic virus (TMV), tomato mosaic virus (ToMV), and viral RNAs from negative stranded RNA viruses, such as tomato spotted wilt virus (TSWV) and Impatiens necrotic spotted virus (INSV), viroids such as peach latent mosaic viroid (PLMVd) or avocado sunblotch viroid (ASBV), satellite viruses such as satellite tobacco mosaic virus (STMV) and the like. Other sources of the PTS/CTS include group I and group II intron RNAs or modified versions thereof in which cryptic splicing sites have been eliminated that may be derived from a bacterium, a fungus or a plastid/chloroplast from a plant, such as an LTRB intron lacking the sequence coding for LTRA (the protein encoded by an LTRA sequence being capable of serving as an PTS/CTS-binding protein in the method of the invention).

Preferably, the intron is a group II intron, such as the *Lactococcus lactis* Ll.ltrB intron or a modified version of it in which cryptic splicing sites have been eliminated as outlined herein. Group II introns are widely represented in the organelles of plants and fungi, and in bacteria. Group II introns useful in the method of the invention are mobile, highly structural retroelements that encode multifunctional protein (intron encoded protein or IEP) which possesses reverse transcriptase (RT) activity. The IEP facilitates splicing of intron RNA by stabilization of the catalytically active RNA structure, performs reverse transcription and insertion of the intron into specific DNA target sites of the bacterial genome at high frequency (Moran et al. (1995) Mol Cell Biol 15:2828-2838; Cousineau et al. (1998) Cell 94:451-462).

Group II introns of bacterial origin, such as those derived from *Lactococcus* that comprise a modified LtrA gene, are preferably used in the method of the invention. The LtrA polynucleotide sequence of a *Lactococcus bacterium*, such as *Lactococcus lactis* may be modified for optimum expression in plants by inserting into it at least one polynucleotide sequence comprising one or more introns from at least one plant nucleic acid sequence, such as from one or more plant genes and by substituting certain selected codons having a low frequency of usage in native plants with codons that occur with a higher frequency in such plants. Typically, the bacterial LtrA sequence of interest is analysed with reference to plant codon usage using in silico comparisons such as those found at the website www.kazusa.or.jp/codon for bacterial codons that occur with low frequency in plants. Such codons may then be substituted with codons that have a high frequency of occurrence in plants, and an in silico-derived modified polynucleotide sequence is generated. From this optimised LtrA sequence a synthetic LtrA polynucleotide sequence corresponding to the in silico generated sequence is made using standard polynucleotide synthesis procedures known in the art, and may then be used in the preparation of constructs of use in the present invention as outlined herein. It is thought that by using a modified sequence that comprises plant codon substitutions as outlined above more plant cell environment stable polynucleotide RNA sequences are generated.

Other types of introns that may be used in the method of the invention include, for example, the group I intron from Tetrahymena (GenBank Acc. No.: X54512; Kruger K et al. (1982) Cell 31:147-157; Roman J and Woodson S A (1998) Proc Natl Acad Sci USA 95:2134-2139), the group II rll intron from *Scenedesmus obliquus* (GenBank Acc. No.: X17375.2 nucleotides 28831 to 29438; Hollander V and Kuck U (1999) Nucl Acids Res 27: 2339-2344; Herdenberger F et al. (1994) Nucl Acids Res 22: 2869-2875; Kuck U et al. (1990) Nucl Acids Res 18:2691-2697), and the Ll.LtrB intron (GenBank Acc. No.: U50902 nucleotides 2854 to 5345).

Aside from heterologous introns described herein, endogenous introns that occur naturally in the plastid, for example, in the chloroplast, such as group II introns from plant chloroplasts, for example the atpF, rpl, trnA, trnI, trnK, petD, petB (Jenkins B. D. et al., The Plant Cell, Vol. 9, 283-296, March 1997).

Introns which occur naturally in the plastids, such as chloroplasts of the plant of interest may be modified such that they have a sequence homology of about 50%, 60%, 70%, 75%, 80%, 85%, 90% or 95%, or of any percentage sequence homology therebetween, with the sequence of the starting intron, while retaining functionality, may also be employed in the method of the invention. Other MTS include RNA domains found on tobacco TNT1, yeast Ty1- and Ty3-like retrotransposons or other RNA that harbours a domain that is recognised by an RNA binding protein that is driven into the chloroplasts.

A "plastid translocation sequence binding protein" (PTS-BP, for example, a CTS-BP) can be any RNA binding protein that recognises and binds to specific RNA domains of interest and is fused to a plastid transit peptide, such as a chloroplast transit peptide. Examples of suitable PTS-BP/CTS-BP proteins may be selected from the Ltra protein from the group II intron II LtrB, coat proteins that bind to RNA viruses such as the coat protein from potato virus X (PVX), the coat protein of TMV, RNA-dependent RNA polymerases (RdRpS) of RNA viruses such as the replicases of PVX or TMV, native plant proteins that are responsible for translocation of viroid RNA (such as PLMVd and ASBV viroids) into the chloroplasts, reverse transcriptase protein from retrotransposons, such as tobacco TnT1, yeast Tyl-1 which recognise structures on the retrotransposon RNA molecule, and proteins that bind to cellular RNAs. Preferably, the PTS-BP protein/CTS-BP protein is the LrtA protein from the group II intron LltrB.

A "plant chloroplast transit peptide" (TP) is one that may be derived or obtained from a plastid-targeted protein, for example transit peptide from small subunit of Rubisco (rbcS) or HSP70 proteins (Marshall & Keegstra (1992) Plant Physiology, 100, 1048-1054), and those that may be predicted by chloroplast localisation sequences programmes (http://www.psort.org).

The "reverse transcriptase" protein, if employed, may be selected from a retrovirus source, such as from plant retroviruses such as SIRE-1 from soybean, or from a retrotransposon source such as from the yeast Tyll retrotransposon, for example the reverse transcriptase-RNaseH domain (Goffeau et al., Science 274 (5287), 546-547 (1996)) or the tobacco TnT1 retrotransposon (RTRH domain) (Vernhettes et., al.; Mol. Biol. Evol. 15 (7), 827-836 (1998)).

A plant nuclear promoter (for example, an exogenous nucleus specific promoter) is one that is able to drive expression of a nucleic acid sequence such as a cDNA sequence or a full length gene sequence in the nucleus of a plant cell, forming a transcribed RNA sequence. The plant nuclear promoter is one that is introduced in front of a nucleic acid sequence of interest and is operably associated therewith. Thus a plant nuclear promoter is one that has been placed in front of a selected polynucleotide component. Typically, a plant nuclear promoter, such as an exogenous nucleus specific promoter, is one that is transferred to a host cell or host plant from a source other than the host cell or host plant.

The cDNAs encoding a polynucleotide of the invention contain at least one type of nucleus specific promoter that is operable in a plant cell, for example, an inducible or a constitutive promoter operatively linked to a first and/or second nucleic acid sequence or nucleic acid sequence component as herein defined and as provided by the present invention. As discussed, this enables control of expression of polynucleotides of the invention. The invention also provides plants transformed with polynucleotide sequences or constructs and methods including introduction of such polynucleotide nucleic acid sequences or constructs into a plant cell and/or induction of expression of said first or second nucleic acid sequence or construct within a plant cell, e.g. by application of a suitable stimulus, such as an effective exogenous inducer.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level, which brings about the desired phenotype. One example of an inducible promoter is the ethanol inducible gene switch disclosed in Caddick et al (1998) Nature Biotechnology 16: 177-180. A number of inducible promoters are known in the art.

Chemically regulated promoters can be used to modulate the expression of a gene or a polynucleotide sequence of the invention in a plant through the application of an exogenous chemical regulator. Depending upon the objective, the promoter may be a chemically inducible promoter, where application of the chemical induces gene expression, or a chemical-repressible promoter, where application of the chemical represses gene expression. Chemically inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid.

Other chemically regulated promoters of interest include steroid-responsive promoters (see, for example, the glucocorticoid-inducible promoter in Schena at al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Where enhanced expression in particular tissues is desired, tissue-specific promoters can be utilized. Tissue-specific promoters include those described by Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505.

So-called constitutive promoters may also be used in the methods of the present invention. Constitutive promoters include, for example, CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680; 5,268,463; and 5,608,142. In a preferment, the plant nuclear promoter used in the method of the invention is a constitutive promoter.

The expression in the plastid, such as in the chloroplast, is effected by employing a plant plastid promoter such as plastid specific promoters and/or transcription regulation elements. Examples include the RNA polymerase promoter (WO 97/06250) and other promoters described in the art, eg in WO 00/07431, U.S. Pat. No. 5,877,402, WO 97/06250, WO 98/55595, WO 99/46394, WO 01/42441 and WO 01/07590; the rpo B promoter element, the atpB promoter element, the clpP promoter element (see also WO 99/46394) and the 16S rDNA promoter element. The plastid specific promoter may also have a polycistronic "operon" assigned to it (EP-A 1 076 095; WO 00/20611). Further promoters that may be used in the method of the invention also include the PrbcL promoter, the Prps16 promoter, and the Prrn16 promoter described in US Patent application 2006/0253916, the plastid specific promoters Prrn-62, Pycf2-1577, PatpB-289, Prps2-152, Prps16-107, Pycf1-41, PatpI-207, PclpP-511, PclpP-173 and PaccD-129 (WO 97/06250; Hajdukiewicz P T J et al. (1997) EMBO J 16:4041-4048), the PaccD-129 promoter of the tobacco accD gene (WO 97/06250), the PclpP-53 promoter of the clpP gene as highly active NEP promoter in chloroplasts (WO 97/06250), the Prrn-62 promoter of the rrn gene, the Prps16-107 promoter of the rps16 gene, the PatpB/E-290 promoter of the tobacco atpB/E gene (Kapoor S et al. (1997) Plant J 11:327-337), and the PrpoB-345 promoter of the rpoB gene (Liere K & Maliga P (1999) EMBO J 18: 249-257). Furthermore, all those promoters which belong to class III (Hajdukiewicz P T J et al. (1997) EMBO J 16:4041-4048) and all fragments of the class II promoters which control the initiation of transcription by NEP may be utilized in the method of the invention. Such promoters or promoter moieties are not generally known to be highly conserved. ATAGAATAAA is given as consensus near the transcription initiation site of NEP promoters (Hajdukiewicz P T J et al (1997) EMBO J 16:4041-4048).

Naturally, the man skilled in the art will appreciate that other terminator DNA sequences may be present in constructs used in the invention. A terminator is contemplated as a DNA sequence at the end of a transcriptional unit which signals termination of transcription. These elements are 3'-non-translated sequences containing polyadenylation signals, which act to cause the addition of polyadenylate sequences to the 3' end of primary transcripts. For expression in plant cells the nopaline synthase transcriptional terminator (A. Depicker et al., 1982, J. of Mol. & Applied Gen. 1:561-573) sequence serves as a transcriptional termination signal.

In another aspect of the invention there is provided a plastid transformation sequence that comprises:

i) a plant plastid translocation sequence;

ii) a plastid transgene cassette; and iii) a primer binding domain.

The plant plastid translocation sequence and the primer binding domain are as defined herein.

The plastid transgene cassette comprises a left flanking sequence (LFS) and a right flanking sequence (RFS) as herein described, and may include a promoter region and/or a terminator region sourced from a higher or lower plant plastid, such as a chloroplast, for example from tobacco, *arabidopsis, brassica* sp., potato, corn (maize), canola, rice, wheat, barley, *brassica* sp., cotton, algae (e.g. blue green species), lemnospora ("duckweed"), or moss (e.g. *physcomitrella patens*). Preferably, the promoter and terminator regions are sourced from higher plant species. Where the LFS and RFS do not include a promoter and/or a terminator region, these components may be placed adjacent to the LFS and/or RFS, as appropriate, or there may be a spacer region therein between. Included within the plastid transgene cassette is at least one transgene or one nucleotide sequence of choice that is destined to be transcribed and/or translated in the chloroplast in accordance with the design of the method of the present invention for example, for the production of desired protein(s), RNAs of interest, or knockout of endogenous plastidal genes and regulatory sequences. Suitable transgenes of interest contemplated for protein or peptide production in a method of the present invention include plant proteins and pharmaceutical proteins for use in mammals, including man, such as insulin, preproinsulin, proinsulin, glucagon, interferons such as $\alpha$-interferon, $\beta$-interferon, $\gamma$-interferon, blood-clotting factors selected from Factor VII, VIII, IX, X, XI, and XII, fertility hormones including luteinising hormone, follicle stimulating hormone growth factors including epidermal growth factor, platelet-derived growth factor, granulocyte colony stimulating factor and the like, prolactin, oxytocin, thyroid stimulating hormone, adrenocorticotropic hormone, calcitonin, parathyroid hormone, somatostatin, erythropoietin (EPO), enzymes such as $\beta$-glucocerebrosidase, haemoglobin, serum albumin, collagen, insect toxic protein from Bacillus thuringiensis; herbicide resistance protein (glyphosate); salt-tolerance proteins; proteins involved in conferring cytoplasmic male sterility to plant breeding lines; nutritional enhancement proteins involved in the biosynthesis of phenolics, starches, sugars, alkaloids, vitamins, and edible vaccines, and the like.

Furthermore, the method of the invention can be used for the production of specific monoclonal antibodies or active fragments thereof and of industrial enzymes.

All proteins mentioned hereinabove are of the plant and human type. Other proteins that are contemplated for production in the present invention include proteins for use in veterinary care and may correspond to animal homologues of human proteins, such as the human proteins mentioned hereinabove.

In a further aspect of the invention there is provided a plant cell that comprises plastids, such as chloroplasts, that are permanently transformed with an exogenous or a heterologous nucleic acid sequence that encodes for a protein of interest. Suitable proteins and peptides of interest may be selected from those provided herein. Accordingly, there is also provided a plant derived from a plant cell as described herein.

Naturally, the person skilled in the art will appreciate that where nuclear terminator DNA sequences will be present in constructs used in the methods of the invention, these are contemplated as comprising a DNA sequence at the end of a transcriptional unit which signals termination of transcription. These elements are 3'-non-translated sequences containing polyadenylation signals, which act to cause the addition of polyadenylate sequences to the 3' end of primary transcripts. For expression in plant cells the nopaline synthase transcriptional terminator (A. Depicker et al., 1982, J. of Mol. & Applied Gen. 1:561-573) sequence serves as a transcriptional termination signal.

Those skilled in the art are well able to construct vectors and design protocols for recombinant nucleic acid sequences or gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711-8721 (1984)) and Guerineau and Mullineaux (1993) (Plant transformation and expression vectors. In: Plant Molecular Biology Labfax (Croy R R D ed.) Oxford, BIOS Scientific Publishers, pp 121-148).

Naturally, the skilled addressee will appreciate that each introduced transgene in a transgene cassette will be under regulatory control of its own exogenous plastidal promoter, for example a chloroplast promoter and terminator. When two or more target proteins are destined to be produced from a single carrier RNA it is preferable if they are able to be readily separated, for example by binding to different protein-specific antibodies (monoclonal or polyclonal) in the harvesting phase of the plant cell culture system.

Selectable genetic markers may facilitate the selection of transgenic plants and these may consist of chimeric genes that confer selectable phenotypes such as resistance to antibiotics such as spectinomycin, streptomycin, kanamycin, neomycin, hygromycin, puramycin, phosphinotricin, chlorsulfuron, methotrexate, gentamycin, spectinomycin, imidazolinones and glyphosate.

When introducing selected nucleic acid sequences according to the present invention into a cell, certain considerations must be taken into account, well known to those skilled in the art. The nucleic acid to be inserted should be assembled within a construct, which contains effective regulatory elements, which will drive transcription. There must be available a method of transporting the construct into the cell. Once the construct is within the cell, integration into the endogenous chromosomal material either will or will not occur. Finally, as far as plants are concerned the target cell type must be such that cells can be regenerated into whole plants.

Plants transformed with DNA segments containing sequences of interest as provided herein may be produced by standard techniques, which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or micro projectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

Thus once a nucleic acid sequence or gene has been identified, it may be reintroduced into plant cells using techniques well known to those skilled in the art to produce transgenic plants of the appropriate phenotype.

*Agrobacterium* transformation is widely used by those skilled in the art to transform dicotyledonous species. Production of stable, fertile transgenic plants in almost all economically relevant monocot plants is also now routine: (Toriyama, et al. (1988) *Bio/Technology* 6, 1072-1074; Zhang, et al. (1988) *Plant Cell Rep.* 7, 379-384; Zhang, et al. (1988) *Theor. Appl. Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828). In particular, *Agrobacterium* mediated transformation is now a highly efficient alternative transformation method in monocots (Hiei et al. (1994) *The Plant Journal* 6, 271-282).

The generation of fertile transgenic plants has been achieved in the cereals rice, maize, wheat, oat, and barley (reviewed in Shimamoto, K. (1994) *Current Opinion in Biotechnology* 5, 158-162; Vasil, et al. (1992) *Bio/Technology* 10, 667-674; Vain et al., 1995, *Biotechnology Advances* 13 (4): 653-671; Vasil, 1996, *Nature Biotechnology* 14 page 702). Wan and Lemaux (1994) *Plant Physiol.* 104: 37-48 describe techniques for generation of large numbers of independently transformed fertile barley plants.

Micro projectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium* coated micro particles (EP-A-486234) or micro projectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol. I, II and III, Laboratory Procedures and Their Applications*, Academic Press, 1984, and Weiss Bach and Weiss Bach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

The invention further encompasses a host cell transformed with vectors or constructs as set forth above, especially a plant or a microbial cell. Thus, a host cell, such as a plant cell, including nucleotide sequences of the invention as herein indicated is provided. Within the cell, the nucleotide sequence may be incorporated within the chromosome.

Also according to the invention there is provided a plant cell having incorporated into its genome at least a nucleotide sequence, particularly heterologous nucleotide sequences, as provided by the present invention under operative control of regulatory sequences for control of expression as herein described. The coding sequence may be operably linked to one or more regulatory sequences which may be heterologous or foreign to the nucleic acid sequences employed in the invention, such as those not naturally associated with the nucleic acid sequence(s) for its (their) expression. The nucleotide sequence according to the invention may be placed under the control of an externally inducible promoter to place expression under the control of the user. A further aspect of the present invention provides a method of making such a plant cell involving introduction of nucleic acid sequence(s) contemplated for use in the invention or a suitable vector including the sequence(s) contemplated for use in the invention into a plant cell and causing or allowing recombination between the vector and the plant cell genome to introduce the said sequences into the genome. The invention extends to plant cells containing a nucleotide sequence according to the invention as a result of introduction of the nucleotide sequence into an ancestor cell.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleotide sequence in question, may be provided. The transgene may be on an extra-genomic vector or incorporated, preferably stably, into the genome. A heterologous gene may replace an endogenous equivalent gene, ie one that normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher activity than wild type, may be used in place of the endogenous gene. Nucleotide sequences heterologous, or exogenous or foreign, to a plant cell may be non-naturally occurring in cells of that type, variety or species. Thus, a nucleotide sequence may include a coding sequence of or derived from a particular type of plant cell or species or variety of plant, placed within the context of a plant cell of a different type or species or variety of plant. A further possibility is for a nucleotide sequence to be placed within a cell in which it or a homologue is found naturally, but wherein the nucleotide sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. Particularly provided are transgenic crop plants, which have been engineered to carry genes identified as stated above. Examples of suitable plants include tobacco (*Nicotiana tabacum*) and other *Nicotiana* species, carrot, vegetable and oilseed *Brassicas*, melons, *Capsicums*, grape vines, lettuce, strawberry, sugar beet, wheat, barley, corn (maize), rice, soybean, peas, *sorghum*, sunflower, tomato, cotton, and potato. Especially preferred transgenic plants of the invention include cotton, rice, oilseed *Brassica* species such as canola, corn (maize) and soybean.

In addition to a plant, the present invention provides any clone of such a plant, seed, selfed or hybrid progeny and descendants, and any part of any of these, such as cuttings, seed. The invention provides any plant propagule that is any part which may be used in reproduction or propagation, sexual or asexual, including cuttings, seed and so on. Also encompassed by the invention is a plant which is a sexually or asexually propagated offspring, clone or descendant of such a plant, or any part or propagule of said plant, offspring, clone or descendant.

The present invention also encompasses the polypeptide expression product of a nucleic acid molecule according to the invention as disclosed herein or obtainable in accordance with the information and suggestions herein. Also provided are methods of making such an expression product by expression from a nucleotide sequence encoding therefore under suitable conditions in suitable host cells e.g. *E. coli*. Those skilled in the art are well able to construct vectors and design protocols and systems for expression and recovery of products of recombinant gene expression.

The heterologous or exogenous target protein is contemplated to be any protein of interest that may be produced by the method of the invention.

A polypeptide according to the present invention may be an allele, variant, fragment, derivative, mutant or homologue of the (a) polypeptides as mentioned herein. The allele, variant, fragment, derivative, mutant or homologue may have substantially the same function of the polypeptides alluded to above and as shown herein or may be a functional mutant thereof.

"Homology" in relation to an amino acid sequence or polypeptide sequence produced by the method of the invention may be used to refer to identity or similarity, preferably identity. As noted already above, high level of amino acid identity may be limited to functionally significant domains or regions.

In certain embodiments, an allele, variant, derivative, mutant derivative, mutant or homologue of the specific sequence may show little overall homology, say about 20%, or about 25%, or about 30%, or about 35%, or about 40% or about 45%, with the specific sequence. However, in functionally significant domains or regions, the amino acid homology may be much higher. Putative functionally significant domains or regions can be identified using processes of bioinformatics, including comparison of the sequences of homologues.

Functionally significant domains or regions of different polypeptides may be combined for expression from encoding nucleic acid as a fusion protein. For example, particularly advantageous or desirable properties of different homologues may be combined in a hybrid protein, such that the resultant expression product, may include fragments of various parent proteins, if appropriate.

Similarity of amino acid sequences may be as defined and determined by the TBLASTN program, of Altschul et al. (1990) *J. Mol. Biol.* 215: 403-10, which is in standard use in the art. In particular, TBLASTN 2.0 may be used with Matrix BLOSUM62 and GAP penalties: existence: 11, extension: 1. Another standard program that may be used is BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (*Adv. Appl. Math.* (1981) 2: 482-489). Other algorithms include GAP, which uses the Needleman and Wunsch algorithm to align two complete sequences that maximizes the number of matches and minimizes the number of gaps. As with any algorithm, generally the default parameters are used, which for GAP are a gap creation penalty=12 and gap extension penalty=4. Alternatively, a gap creation penalty of 3 and gap extension penalty of 0.1 may be used. The algorithm FASTA (which uses the method of Pearson and Lipman (1988) *PNAS USA* 85: 2444-2448) is a further alternative.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Further discussion of polypeptides according to the present invention, which may be encoded by nucleic acid according to the present invention, is found below.

The teaching of all references cited herein is incorporated in its entirety into the present description.

There now follow non-limiting examples and figures illustrating the invention.

FIGURES

FIG. 1: the major components of chloroplast transformation system.

(1) Transformation vector contains (i) chloroplast translocation sequence (CTS); (ii) chloroplast transgene cassette comprising left flanking sequence (LFS) and right flanking sequence (RFS) to facilitate insertion of the cassette into the chloroplast genome using homologous recombination, promoter region from tobacco chloroplast rrn16 gene (Prrn), aadA gene as a selectable marker (aadA), transcription terminator from chloroplast genome (term); and (iii) primer binding domain (PBD). (2) Reverse Transcriptase-RNase H gene translationally fused to the chloroplast transit peptide from small subunit of tobacco Rubisco gene (rbcS-cTP). (3) CTS-Binding peptide translationally fused to the chloroplast transit peptide from *Arabidopsis* HSP60 gene (HSP60-cTP).

Figure 2:
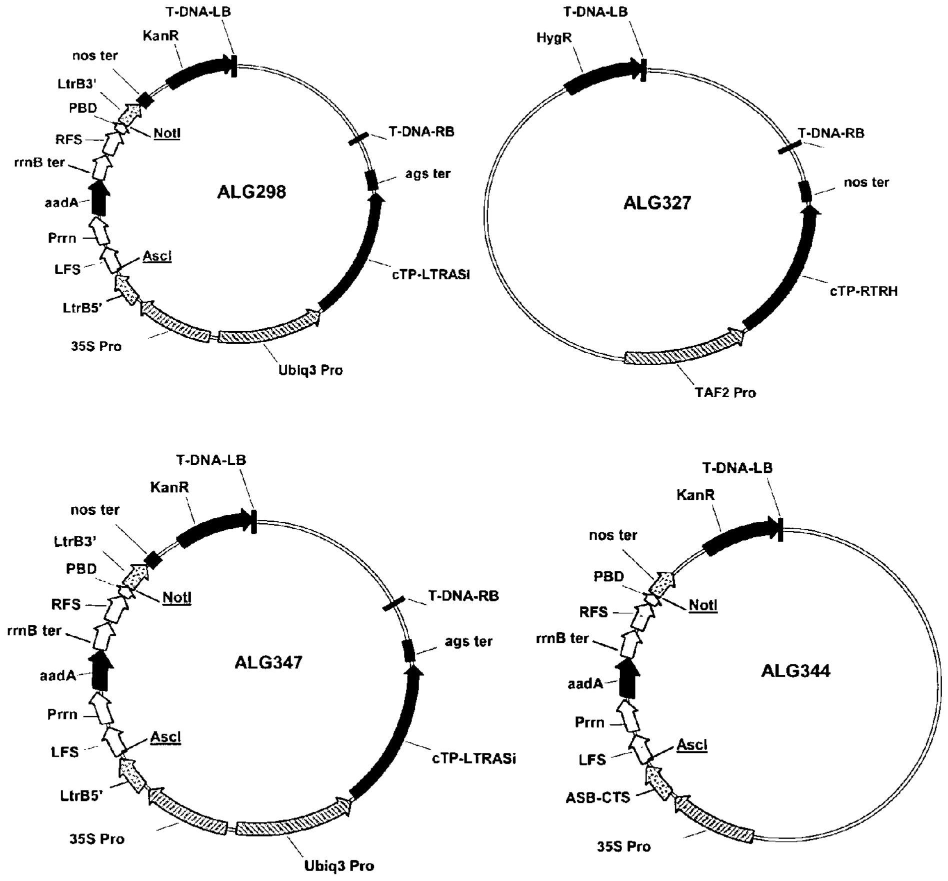

FIG. 2: set of constructs used for chloroplast transformation in tobacco (ALG298, ALG327 and ALG 344) and in *Arabidopsis* (ALG347 and ALG327)

The chloroplast transformation cassette contains left and right flanking sequences (LFS and RFS), Prrn promoter (Prrn), aadA gene for spectinomycin selection (aadA), and rrnB transcription terminator (rrnB ter). Primer binding domain (PBD) from yeast Ty1 retrotransposon designed for capturing tRNA-Met from chloroplasts was fused to chloroplast transgene cassette. The resulting cassette was inserted within domain IV of LtrB (LtrB5' and LtrB3') intron from *Lactococcus lactis* (ALG298 and ALG347) or fused to chloroplast translocation sequence from Avocado sunblotch viroid (ASB-CTS in ALG344). The chloroplast transgene cassette was expressed from nuclear inserted cassette and resultant RNA was translocated into the chloroplast using LtrASi protein for vectors (ALG298 and ALG347), or using native plant proteins for vector ALG344. Reverse transcription of the RNA was performed by Reverse transcriptase-RNaseH fused to chloroplast transit peptide (cTP—RTRH) from HSP60 gene (ALG327). Ubiq3 Pro—*Arabidopsis* promoter from ubiquitin 3 gene; 35S Pro—promoter from Cauliflower Mosaic Virus 35S gene, TAF2 Pro—*Arabidopsis* promoter from TAF 2 gene; nos ter—transcription terminator from *Agrobacterium* nos gene.

Figure 3:
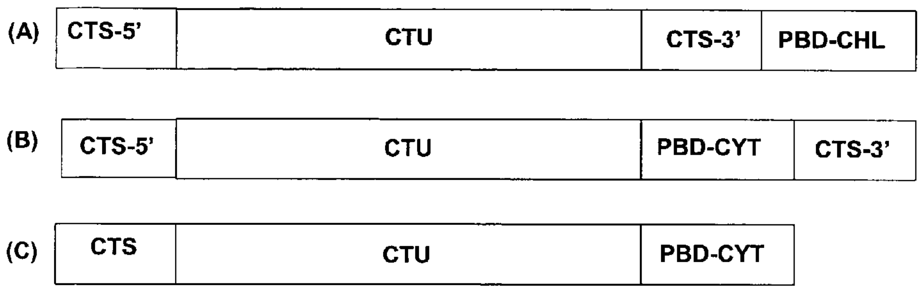

FIG. 3: modifications of the chloroplast transformation cassette were made by designing primer binding domain and positioning of building blocks on the transgene cassette.

CTU—chloroplast transformation unit; CTS-5'-chloroplast translocation sequence located at the 5'-end of the transformation cassette; CTS-3'—chloroplast translocation sequence located at the 3'-end of the transformation cassette; PDB-CHL—primer binding domain designed for reverse transcription in the chloroplasts using tRNA-Met from chloroplasts; PBD-CYT—primer binding domain designed for reverse transcription in the cytoplasm using cytoplasmic tRNA-Met.

The modifications detailed in Example section 1B hereinafter and corresponding figures include a first modification of the use of PBD for the binding of cytoplasmic tRNA-Met as primer [FIG. 3(C)]. As a second modification CTS can be located at both the 5'- and 3'-ends of the transformation cassette, such as in the case with the LtrB intron. The transgene cassette is inserted inside of the LtrB intron (domain IV). The PDB-CHL is located downstream of the LtrB 3'-end of the cassette (CTS-3'), so that the LtrA protein is able to function as both a translocation protein and reverse transcriptase. The LtrA protein has three major functions: (1) as a maturase (it binds to LtrB RNA and stabilises the secondary structure of the RNA, and assists splicing); (2) as an endonuclease (it induces single-stranded DNA breaks on target site); and (3) as a reverse transcriptase (it performs reverse transcription of the intron RNA after insertion of the LtrB intron RNA into the donor site).

The LtrA protein is unable to perform the reverse transcription reaction efficiently if the PBD-CYT is located adjacent to and in front of a chloroplast translocation sequence at the 3'-end of the CTU (CTS-3') as in FIG. 3(B), but can efficiently reverse transcribe RNA if the PBD is located downstream of a chloroplast translocation sequence (CTS-3') as shown in FIG. 3A. Such a positioning or the combination of components of the transformation cassette as shown in FIG. 3(A) allows both the translocation of the CTU into the chloroplast and reverse transcription of the CTU by the LtrA protein. Thus, by positioning of the CTS components and of the PBD-CHL as shown in FIG. 3(A) the procedure of transformation is simplified since there is no requirement to co-deliver another gene to provide a reverse transcriptase function.

A similar simplification of the procedure is achieved if a PBD-CYT is used, since there is a significant amount of native endogenous reverse transcriptase in the cytoplasm, and reverse transcription is initiated by endogenous reverse transcriptase using cytoplasmic tRNA-Met. This also eliminates the necessity for the co-delivery of another gene for reverse transcription in the chloroplasts.

The case in FIGS. 1A and B is attributed to LtrB intron, the case in FIG. 1C attributed to ASB-CTS.

Figure 4:
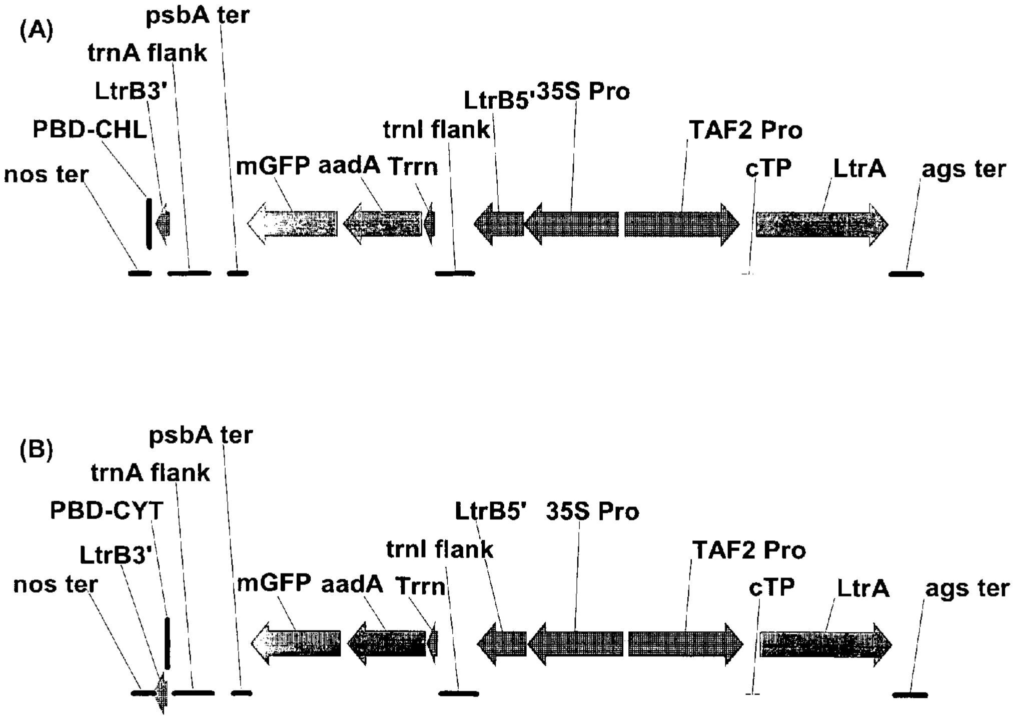

FIG. 4: schematic presentation of constructs based on the LtrB-CTS for chloroplast transformation in tobacco.

Nos ter—nos transcription terminator, LtrB3—3'-prime end of LtrB intron, PBD-CHL—primer binding domain for chloroplast tRNA-Met, PDB-CYT—primer binding domain for cytoplasmic tRNA-Met, trnA flank—left flank of the transgene cassette, psbA ter—chloroplast transcription terminator from tobacco, mGFP—mGFP4 gene, aadA-aadA gene, Trrn—rrn16 chloroplast promoter from tobacco, trnI flank—right flank of transgene cassette, LtrB5—5'-prime end of LtrB intron, 35S Pro—35S promoter from cauliflower mosaic virus (CaMV), TAF2 Pro—promoter from *Arabidopsis* TAF2 gene, cTP—chloroplast transit peptide from rbcS gene of tobacco, LtrA—gene encoded by open reading frame of LtrB intron, ags ter—ags gene transcription terminator.

Figure 5:
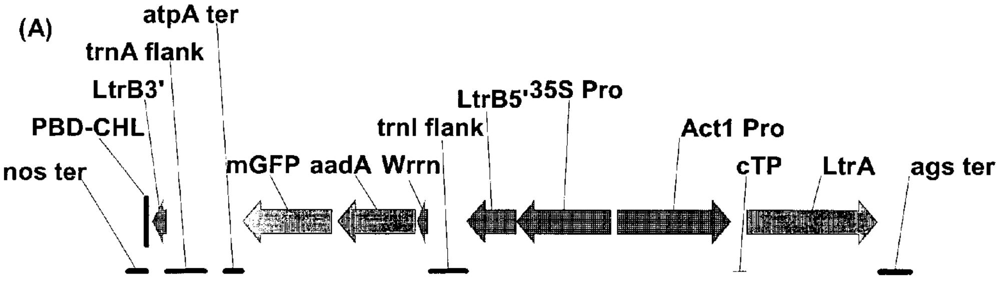
Figure 5:
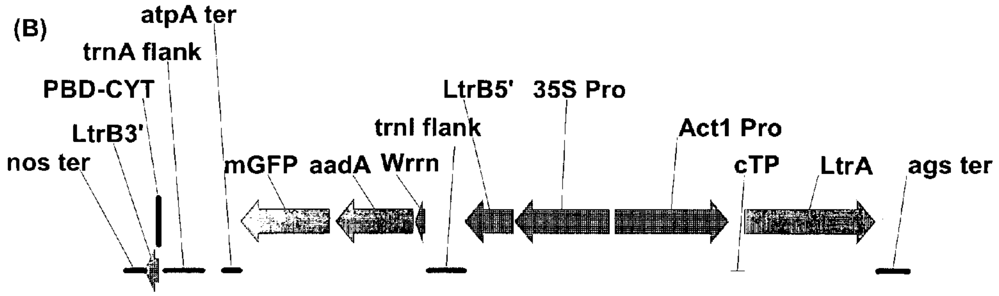

FIG. 5: schematic presentation of constructs based on the LtrB-CTS for chloroplast transformation in rice.

Nos ter—nos transcription terminator, LtrB3—3'-prime end of LtrB intron, PBD-CHL—primer binding domain for chloroplast tRNA-Met, PDB-CYT—primer binding domain for cytoplasmic tRNA-Met, trnA flank—left flank of the transgene cassette, atpA ter—chloroplast transcription terminator from wheat, mGFP—mGFP4 gene, aadA—aadA gene, Wrrn—rrn16 chloroplast promoter from wheat, trnI flank-right flank of transgene cassette, LtrB5—5'-prime end of LtrB intron, 35S Pro—35S promoter from cauliflower mosaic virus (CaMV), Act1 Pro—actin 1 gene promoter from rice, cTP—chloroplast transit peptide from rbcS gene of tobacco, LtrA—gene encoded by open reading frame of LtrB intron, ags ter—ags gene transcription terminator.

Figure 6:
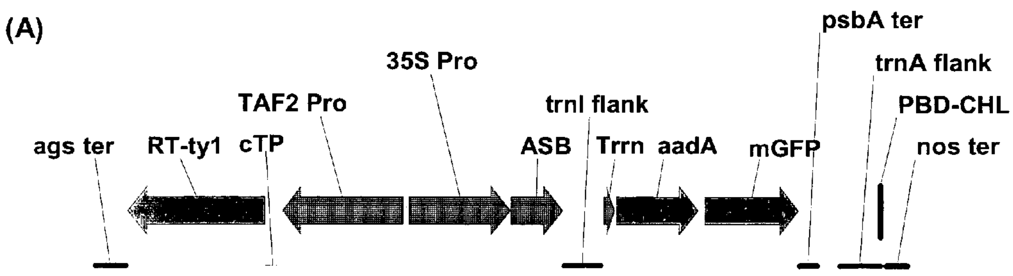
Figure 6:
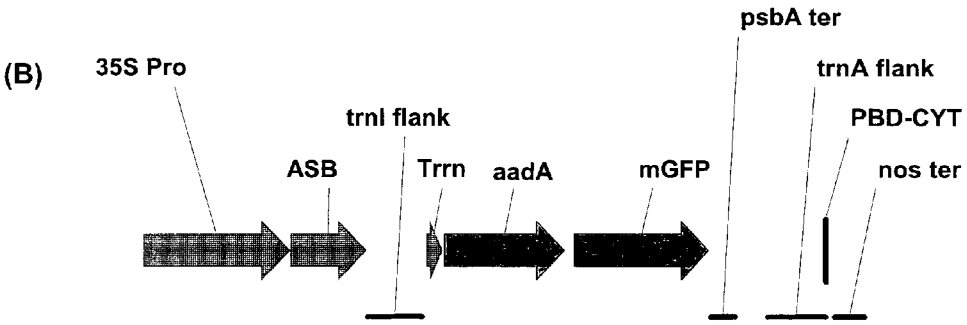

FIG. 6: Schematic presentation of constructs based on ASB-CTS for chloroplast transformation in tobacco.

Nos ter—nos transcription terminator, ASB—sequence from Avocado sunblotch viroid (ASBVd) as CTS, PBD-CHL—primer binding domain for chloroplast tRNA-Met, PDB-CYT—primer binding domain for cytoplasmic tRNA-Met, trnA flank—left flank of the transgene cassette, psbA ter—chloroplast transcription terminator from tobacco, mGFP—mGFP4 gene, aadA—aadA gene, Trrn—rrn16 chloroplast promoter from tobacco, trnI flank—right flank of transgene cassette, 35S Pro—35S promoter from cauliflower mosaic virus (CaMV), TAF2 Pro—promoter from *Arabidopsis* TAF2 gene, cTP—chloroplast transit peptide from rbcS gene of tobacco, RT-ty1—reverse transcriptase gene from yeast ty1 retrotransposon, ags ter—ags gene transcription terminator.

Figure 7:
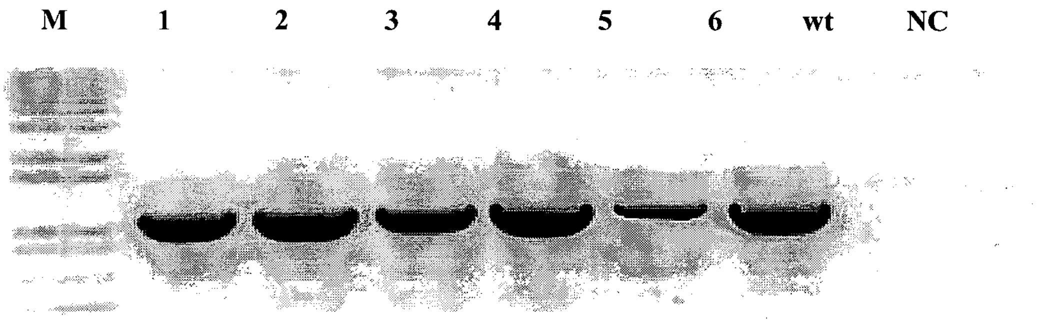

FIG. 7: PCR amplification of left flanking junction in tobacco transformed by the LtrB-CTS-based vectors.

M—DNA marker, 1-6—independent transgenic lines, wt—non-transgenic tobacco, NC—negative control without DNA.

Figure 8:
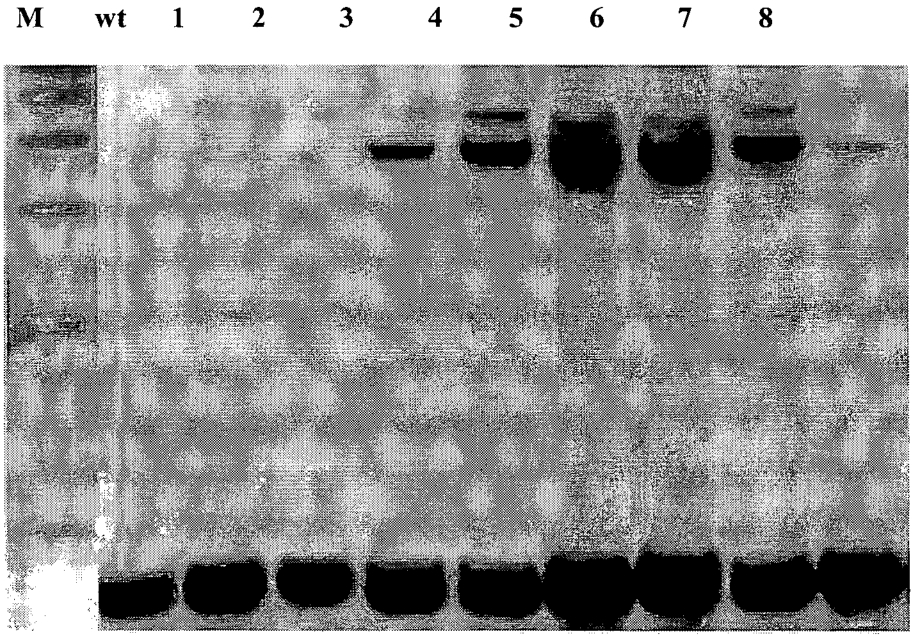

FIG. 8: Southern hybridisation for tobacco transformed with ASB-CTS and LtrB-CTS based vectors.

Expected size of wild type DNA band is ~1.3 kb, and band with transgene insertion ~3.6 kb. Chloroplast probe upstream of LFS was used as a probe. M—DNA marker, wt—DNA from non-transgenic line, 1-3—ASB-CTS lines, 4-8—LtrB-CTS transgenic lines.

Figure 9:
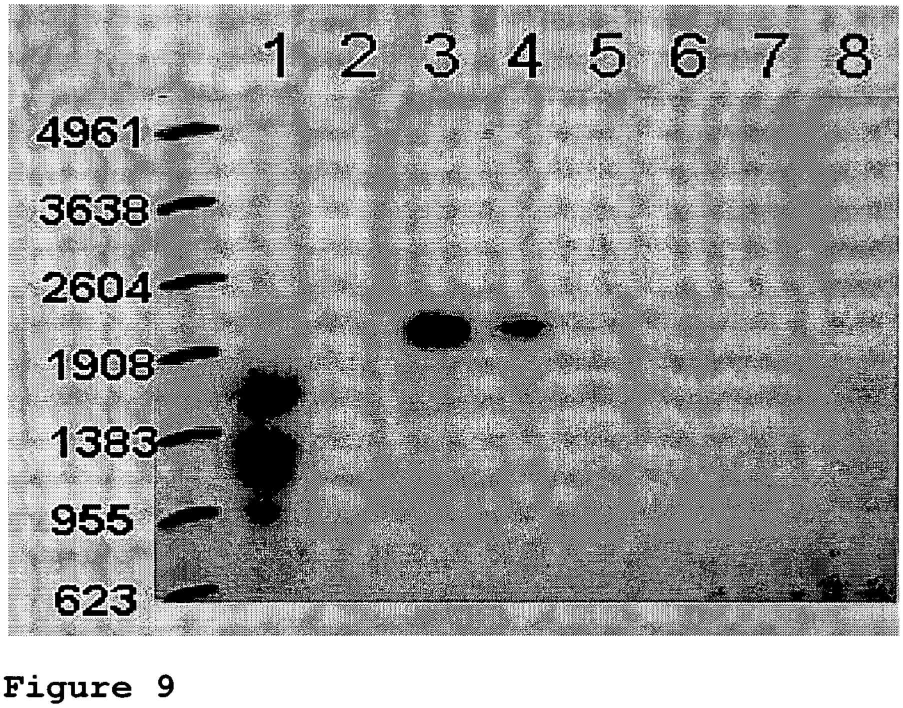

FIG. 9: Northern analysis for tobacco plants transformed with LtrB-CTS based vector.

The aad-GFP DNA probe was used for hybridisation. Expected size of the band is ~1.5 kb. Lane 1—RNA from plants transformed with 35S-aadA-GFP-nos cassette; lane 2—WT RNA; lanes 3-8—independent transgenic lines.

EXPERIMENTAL SECTION 1A

A Novel Approach for Efficient Chloroplast Transformation

A new method for chloroplast transformation in plants comprises (1) a transformation vector consisting of 3 major domains: (i) chloroplast translocation sequence (CTS), (ii) chloroplast transgene cassette, (iii) primer binding domain (PBD) which uses chloroplast tRNA-fMet or any other chloroplast tRNAs as a primer for reverse transcription;

(2) Reverse Transcriptase—RNase H (RT-RH) from retrotransposon or retroviruses fused to chloroplast transit peptide for targeting into chloroplasts;

(3) RNA binding protein that binds to chloroplast translocation sequence (CTS) of the transformation vector, fused to chloroplast transit peptide (FIG. 1).

Technology Rationale

The process of chloroplast transformation comprises two steps:

(1) Targeting of RNA-Protein Complex to the Chloroplasts.

After delivery of the chloroplast transformation construct into the plant cell a strong expression of the RNA which contains the chloroplast translocation sequence (CTS) transgene cassette and primer binding domain (PBD) is achieved from the nuclear specific promoter. The CTS binding protein (CTS-BP) fused to a chloroplast transit peptide, will be also over-expressed on co-delivery from the same or a different vector and then will bind to the CTS, and facilitate translocation of the RNA into the chloroplasts.

Once the chloroplast transformation vector is presented in the plant cell via nuclear transformation, the chloroplast will then be permanently bombarded by the expressed CTS-BP-RNA complex. Such stable and continuous pumping of the complex into the targeted organelle is a prerequisite for achieving a high efficiency of organelle transformation. The technology exploits the finding that the chloroplast transit sequence is sufficient to permit the whole CTS-BP-RNA complex to be then taken up by the chloroplast.

Chloroplast translocation sequence (CTS) can be selected from a number of RNA sequences such as viroid RNA, groupI and groupII intron RNA, viral coat protein binding domains, retrotransposon primer binding sites, which are recognised by corresponding native RNA binding proteins.

(2) Reverse Transcription of the Transgene Cassette and Insertion into the Chloroplast Genome.

Once the RNA of the transformation vector is inside of the organelle, primer binding domain (PBD) of the vector RNA captures tRNA-fMet as a primer, and the over-expression of the reverse transcriptase (RT-RH) fused to the chloroplast transit peptide facilitates reverse transcription of RNA into single stranded DNA. This is followed by insertion of the reverse transcribed cassette into the chloroplast genome using homologous recombination between flanking sequences of the transgene cassette and the homologous regions in the chloroplast genome.

Primer binding domain (PBD) is designed to capture RT-RH protein and chloroplast tRNA-fMet (or other chloroplast tRNAs) as a primer, and initiate reverse transcription of chloroplast transgene cassette RNA into single-stranded DNA.

Once the population of organelle genomes has been transformed in the initial plant line, the nuclear encoded transgenes are no longer required and they can then be removed through segregation in subsequent plant generations, leaving a clean organelle transformed plant line.

Materials and Methods

Preparation of Group II Intron Based Chloroplast Translocation Sequence (CTS)

LtrB intron from *Lactococcus lactis* was synthesised by commercial DNA synthesis provider. Potential splicing sites were eliminated from this sequence as described in our previous patent. The domain for insertion of transgene cassette (AscI-MluI-NotI sites) is underlined and shown in bold letters.

LtrB intron sequence SEQ ID NO. 1

GGATCCCTCGAGGTGCGCCCAGATAGGGTGTTAAGTCAAGTAGTTTAAGGTACTACTCAGTAAGAT

AACACTGAAAACAGCCAACCTAACCGAAAAGCGAAAGCTGATACGGGAACAGAGCACGGTTGGAAA

GCGATGAGTTAGCTAAAGACAATCGGCTACGACTGAGTCGCAATGTTAATCAGATATAAGCTATAA

GTTGTGTTTACTGAACGCAAGTTTCTAATTTCGGTTATGTGTCGATAGAGGAAAGTGTCTGAAACC

TCTAGTACAAAGAAAGCTAAGTTATGGTTGTGGACTTAGCTGTTATCACCACATTTGTACAATCTG

TTGGAGAACCAATGGGAACGAAACGAAAGCGATGGCGAGAATCTGAATTTACCAAGACTTAACACT

AACTGGGGATAGCCTAAACAAGAATGCCTAATAGAAAGGAGGAAAAAGGCTATAGCACTAGAGCTT

GAAAATCTTGCAAGGCTACGGAGTAGTCGTAGTAGTCTGAGAAGGCTAACGGCCTTTACATGGCAA

AGGGCTACAGTTATTGTGTACTAAAATTAAAAATTGATTAGGGAGGAAAACCTCAAAATGAAACCA

ACAATGGCAATTTTAGAAAGAATCAGTAAAAATTCACAAGAAAATATAGACGAAGTTTTTACAAGA

CTTTATCGTTATCTTTTACGTCCTGATATTTATTACGTGGCGGGCGCGCCACGCGTGCGGCCGCTG

GGAAATGGCAATGATAGCGAAAGAACCTAAAACTCTGGTTCTATGCTTTCATTGTCATCGTCACGT

GATTCATAAACACAAGTGAATTTTTACGAACGAACAATAACAGAGCCGTATACTCCGAGAGGGGTA

CGTACGGTTCCCGAAGAGGGTGGTGCAAACCAGTCACAGTAATGTGAACAAGGCGGTACCTCCCTA

CTTCACCATATCATTTTTAATTCTACGAATCTTTATACTGGCAAACAATTTGACTG

-

The chloroplast translocation sequence (CTL) from Avocado sunblotch viroid (Bank Accession No. J02020) was synthesised by PCR using the set of the following overlapping primers:

AS839 SEQ ID NO. 2

GAACTAATTTTTTTAATAAAAGTTCACCACGACTCCTCCTTCTCTCACAA

AS840 SEQ ID NO. 3

TAAAAAAATTAGTTCACTCGTCTTCAATCTCTTGATCACTTCGTCTCTTC

AS841 SEQ ID NO. 4

TGCGAGACTCATCAGTGTTCTTCCCATCTTTCCCTGAAGAGACGAAGTGA

AS842 SEQ ID NO. 5

CTGATGAGTCTCGCAAGGTTTACTCCTCTATCTTCATTGTTTTTTTACAA

AS843 SEQ ID NO. 6

GGGCGCGCCAAGATTTTGTAAAAAAACAATGAAGA

AS844 SEQ ID NO. 7

GCTCGAGACTTGTGAGAGAAGGAGGAGTC

-continued

```
The CTL sequence from Avocado sunblotch viroid          SEQ ID NO. 8
GCTCGAGACTTGTGAGAGAAGGAGGAGTCGTGGTGAACTTTTATTAAAAAAATTAGTTCACTCGTC

TTCAATCTCTTGATCACTTCGTCTCTTCAGGGAAAGATGGGAAGAACACTGATGAGTCTCGCAAGG

TTTACTCCTCTATCTTCATTGTTTTTTTACAAAATCTTGGGCGCGCCC
```

The expression of chloroplast translocation sequence and chloroplast cassette fused to it was driven by 35S promoter from Cauliflower mosaic virus obtained by DNA synthesis

```
35S promoter sequence                                   SEQ ID NO. 9
CAATCCCACAAAAATCTGAGCTTAACAGCACAGTTGCTCCTCTCAGAGCAGAATCGGGTATTCAAC

ACCCTCATATCAACTACTACGTTGTGTATAACGGTCCACATGCCGGTATATACGATGACTGGGGTT

GTACAAAGGCGGCAACAAACGGCGTTCCCGGAGTTGCACACAAGAAATTTGCCACTATTACAGAGG

CAAGAGCAGCAGCTGACGCGTACACAACAAGICAGCAAACAGACAGGTTGAACTTCATCCCCAAAG

GAGAAGCTCAACTCAAGCCCAAGAGCTTTGCTAAGGCCCTAACAAGCCCACCAAAGCAAAAAGCCC

ACTGGCTCACGCTAGGAACCAAAAGGCCCAGCAGTGATCCAGCCCCAAAAGAGATCTCCTTTGCCC

CGGAGATTACAATGGACGATTTCCTCTATCTTTACGATCTAGGAAGGAAGTTCGAAGGTGAAGTAG

ACGACACTATGTTCACCACTGATAATGAGAAGGTTAGCCTCTTCAATTTCAGAAAGAATGCTGACC

CACAGATGGTTAGAGAGGCCTACGCAGCAGGTCTCATCAAGACGATCTACCCGAGTAACAATCTCC

AGGAGATCAAATACCTTCCCAAGAAGGTTAAAGATGCAGTCAAAAGATTCAGGACTAATTGCATCA

AGAACACAGAGAAAGACATATTTCTCAAGATCAGAAGTACTATTCCAGTATGGACGATTCAAGGCT

TGCTTCATAAACCAAGGCAAGTAATAGAGATTGGAGTCTCTAAAAAGGTAGTTCCTACTGAATCTA

AGGCCATGCATGGAGTCTAAGATTCAAATCGAGGATCTAACAGAACTCGCCGTGAAGACTGGCGAA

CAGTTCATACAGAGTCTTTTACGACTCAATGACAAGAAGAAAATCTTCGTCAACATGGTGGAGCAC

GACACTCTGGTCTACTCCAAAAATGTCAAAGATACAGTCTCAGAAGACCAAAGGGCTATTGAGACT

TTTCAACAAAGGATAATTTCGGGAAACCTCCTCGGATTCCATTGCCCAGCTATCTGTCACTTCATC

GAAAGGACAGTAGAAAAGGAAGGTGGCTCCTACAAATGCCATCATTGCGATAAAGGAAAGGCTATC

ATTCAAGATCTCTCTGCCGACAGTGGTCCCAAAGATGGACCCCCACCCACGAGGAGCATCGTGGAA

AAAGAAGACGTTCCAACCACGTCTTCAAAGCAAGTGGATTGATGTGACATCTCCACTGACGTAAGG

GATGACGCACAATCCCACTATCCTTCGCAAGACCCTTCCTCTATATAAGGAAGTTCATTTCATTTG

GAGAGGACACG
```

The chloroplast transgene cassette contains left and right flanking sequences (LFS and RFS) for insertion of whole cassette into the chloroplast genome using homologous recombination, Prrn16 promoter region from tobacco, aadA gene as a selectable marker, and 3'UTR sequence of psbA gene as transcription terminator (FIG. 1).

LFS sequences for tobacco and *Arabidopsis* were amplified using the following PCR primers:

```
AS699                                   SEQ ID NO. 10
GGCGCGCCGTGGGATCCGGGCGGTCCG

AS700                                   SEQ ID NO. 11
GGCATGCTGGCGCAGCTGGGCCATCC

Tobacco LFS sequence                    SEQ ID NO. 12
GGCGCGCCATGGGATCCGGGCGGTCCGGGGGGGACCACCACGGCTCCTCT

CTTCTCGAGAATCCATACATCCCTTATCAGTGTATGGACAGCTATCTCTC
```

-continued

```
GAGCACAGGTTTAGCAATGGGAAAATAAAATGGAGCACCTAACAACGCAT

CTTCACAGACCAAGAACTACGAGATCGCCCCTTTCATTCTGGGGTGACGG

AGGGATCGTACCATTCGAGCCGTTTTTTTCTTGACTCGAAATGGGAGCAG

GTTTGAAAAAGGATCTTAGAGTGTCTAGGGTTGGGCCAGGAGGGTCTCTT

AACGCCTTCTTTTTTCTTCTCATCGGAGTTATTTCACAAAGACTTGCCAG

GGTAAGGAAGAAGGGGGGAACAAGCACACTTGGAGAGCGCAGTACAACGG

AGAGTTGTATGCTGCGTTCGGGAAGGATGAATCGCTCCCGAAAAGGAATC

TATTGATTCTCTCCCAATTGGTTGGACCGTAGGTGCGATGATTTACTTCA

CGGGCGAGGTCTCTGGTTCAAGTCCAGGATGGCCGCATGCC
```

```
Arabidopsis LFS sequence                SEQ ID NO. 13
GGCGCGCCGTGGGATCCGGGCGGTCCGGAGGGGACCACTATGGCTCCTCT
```

-continued

CTTCTCGAGAATCCATACATCCCTTATCAGTGTATGGACAGCTATCTCTC
GAGCGCAGGTTTAGGTTCGGCCTCAATGGGAAAATAAAATGGAGCACCTA
ACAACGTATCTTCACAGACCAAGAACTACGAGATCACCCCTTTCATTCTG
GGGTGACGGAGGGATCGTACCGTTCGAGCCTTTTTTTCATGTTATCTATC
TCTTGACTCGAAATGGGAGCAGGTTTGAAAAAGGATCTTAGAGTGTCTAG
GGTTAGGCCAGTAGGGTCTCTTAACGCCCTCTTTTTTCTTCTCATCGAAG
TTATTTCACAAATACTTCCTATGGTAACGAAGAGGGGGGGAACAAGCACA
CTTGGAGAGCGCAGTACAACGGAGAGTTGTATGCTGCGTTCGGGAAGGAT
GAATCGCTCCCGAAAAGGAATCTATTGATTCTCTCCCAATTGGTTGGACC
ATAGGTGCGATGATTTACTTCACGGGCGAGGTCTCTGGTTCAAATCCAGG
ATGGCCCAGCTGCGCCAGCATGC

RFS sequences were amplified using the following PCR primers:

AS764 SEQ ID NO. 14
TGATATCGGATGGCCCTGCTGCGCCAGGGAAAAGAAT

AS845 SEQ ID NO. 15
GCCGCGGATTGCCCTTCTCCGACCCTGAC

Tobacco RFS sequence SEQ ID NO. 16
GATATCGGATGGCCCTGCTGCGCCAGGGAAAAGAATAGAAGAAGCATCTG
ACTACTTCATGCATGCTCCACTTGGCTCGGGGGGATATAGCTCAGTTGGT
AGAGCTCCGCTCTTGCAATTGGGTCGTTGCGATTACGGGTTGGATGTCTA
ATTGTCCAGGCGGTAATGATAGTATCTTGTACCTGAACCGGTGGCTCACT
TTTTCTAAGTAATGGGGAAGAGGACCGAAACGTGCCACTGAAAGACTCTA
CTGAGACAAAGATGGGCTGTCAAGAACGTAGAGGAGGTAGGATGGGCAGT
TGGTCAGATCTAGTATGGATCGTACATGGACGGTAGTTGGAGTCGGCGGC
TCTCCCAGGGTTCCCTCATCTGAGATCTCTGGGGAAGAGGATCAAGTTGG
CCCTTGCGAACAGCTTGATGCACTATCTCCCTTCAACCCTTTGAGCGAAA
TGCGGCAAAAGAAAAGGAAGGAAAATCCATGGACCGACCCCATCATCTCC
ACCCCGTAGGAACTACGAGATCACCCCAAGGACGCCTTCGGCATCCAGGG
GTCACGGACCGACCATAGAACCCTGTTCAATAAGTGGAACGCATTAGCTG
TCCGCTCTCAGGTTGGGCAGTCAGGGTCGGAGAAGGGCAATCCGCGG

*Arabidopsis* RFS sequence SEQ ID NO. 17
GATATCGGATGGCCCTGCTGCGCCAAGGAAAAGAATATAAGAAGGATCTG
ACTCCTTCATGCATGCTCCACTTGGCTCGGGGGATATAGCTCAGTTGGTA
GAGCTCCGCTCTTGCAATTGGGTCGTTGCGATTACGGGTTGGGTGTCTAA
TTGTCCAGGCGGTAATGATAGTATCTTGTACCTGAACCGGTGGCTCACTT
TTTCTAAGTAATGGGGAAAAGGACCGAAACATGCCACTGAAAGACTCTAC
TGAGACAAAGATGGGCTGTCAAGAACGTAGAGGAGGTAGGATGGTCAGTT
GGTCAGATCTAGTATGGATCGTACATGGACGGTAGTTGGAGTCGGCGGCT
CTCCTAGGGTTCCCTCGTCTGGGATTGATCCCTGGGGAAGAGGATCAAGT
TGGCCCTTGCGAACAGCTTGATGCACTATCTCCCTTCAACCCTTTGAGCG -continued AAATGCGGCAAAAGGAAGGAAAATCCATGGACCGACCCCATCGTCTCCAC
CCCGTAGGAACTACGAGATCACCCCAAGGACGCCTTCGGTATCCAGGGGT
CGCGGACCGACCATAGAACCCTGTTCAATAAGTGGAATGCATTAGCTGTC
CGCTCGCAGGTTGGGCAGTAAGGGTCGGAGAAGGGCAATCCGCGG Prrn promoter was amplified from tobacco genomic DNA cv. Petite Gerard using following PCR primers:

AS750 SEQ ID NO. 18
GGCATGCCGCAATGTGAGTTTTTGTAGTTG

Prrn-R SEQ ID NO. 19
ACTTGTATCGATGCGCTTCATATTCGCCCGGA

Prrn16 promoter sequence SEQ ID NO. 20
GCATGCCGCAATGTGAGTTTTTGTAGTTGGATTTGCTCCCCCGCCGTCGT
TCAATGAGAATGGATAAGAGGCTCGTGGGATTGACGTGAGGGGGCAGGGA
TGGCTATATTTCTGGGAGCGAACTCCGGGCGAATATGAAGCGCATCGATA
CAAGT aadA gene was synthesised by commercial DNA synthesis provider. Three introns from *Arabidopsis* gene At2g29890 were inserted into the coding sequence to optimise expression of the aadA in the cytoplasm of plant cells. The introns are underlined and shown in bold letters.

aadA gene sequence SEQ ID NO. 21
ATGGCAGAAGCGGTGATCGCCGAAGTATCGACTCAACTATCAGAGGTAAG
TAACTTTTAGCTCTCAGCTGCTGTTTACTAAGTTCATGCCATACATTGAT
TCTGGTTTATTAAGGGTTATGTTCAGTATTACTAGTAACAAAATCTATTT
CTTCGTTTCCGTCTGCAGGTAGTTGGCGTCATCGAGCGCCATCTCGAACC
GACGTTGCTGGCCGTACATTTGTACGGCTCCGCAGTGGATGGCGGCCTGA
AGCCACACAGTGATATTGATTTGCTGGTTACGGTGACCGTAAGGCTTGAT
GAAACAACGCGGCGAGCTTTGATCAACGACCTTTTGGAAACTTCGGCTTC
CCCTGGAGAGAGCGAGATTCTCCGCGCTGTAGAGGTAATTTTCATCTTTG
TTTGGCCTTCCAAGTGCTTTTTTTGCTGTTTACGGGTGGAACTTCAGTAA
AAATGGGATCAAAACATCATATGGCATAAATAAATTTTAAGAATGGCGAA
CTCGGGGTTACCGAATATGGCTTCCTTTTTCAGTGTTTCTTAGTCCATTG
TACTTATGAGATTGCAGGTCACCATTGTTGTGCACGACGACATCATTCCG
TGGCGTTATCCAGCTAAGCGCGAACTGCAATTTGGAGAATGGCAGCGCAA
TGACATTCTTGCAGGTATCTTCGAGCCAGCCACGATCGACATTGATCTGG
CTATCTTGCTGACAAAAGCAAGAGAACATAGCGTTGCCTTGGTAGGTCCA
GCGGCGGAGGAACTCTTTGATCCGGTTCCTGAACAGGATCTATTTGAGGC
GCTAAATGAAACCTTAACGCTATGGAACTCGCCGCCCGACTGGGCAGGTA
AGAAATCTTTTCCCATCTTGAAGTCACCTCAAACCGAACGTTAGGAAATT
CCAAAATGTTTTGATAGTAGTCTACTTAGTTTCAAGTTTTGGGTTTGTGT
ATACTTTCACTAATAATATGCGTGGAAACATTGCAGGTGATGAGCGAAAT
GTAGTGCTTACGTTGTCCCGCATTTGGTACAGCGCAGTAACCGGCAAAAT
CGCGCCGAAGGATGTCGCTGCCGACTGGGCAATGGAGCGCCTGCCGGCCC -continued

AGTATCAGCCCGTCATACTTGAAGCTAGACAGGCTTATCTTGGACAAGAA

GAAGATCGCTTGGCCTCGCGCGCAGATCAGTTGGAAGAATTTGTCCACTA

CGTGAAAGGCGAGATCACCAAGGTAGTCGGCAAATAA

The psbA 3'UTR terminator was amplified from the tobacco genomic DNA cv Petite Gerard using the following primers:

AS749 SEQ ID NO. 22
GGATATCAAACAAATACAAAATCAAAATAGA

AS778 SEQ ID NO. 23
GGAATTCTGAGCGCGCTAGAGCGATCCTG psbA 3'UTR sequence SEQ ID NO. 24
GAATTCTGAGCGCGCTAGAGCGATCCTGGCCTAGTCTATAGGAGGTTTTG

AAAAGAAAGGAGCAATAATCATTTTCTTGTTCTATCAAGAGGGTGCTATT

GCTCCTTTCTTTTTTTCTTTTTATTTATTTACTAGTATTTTACTTACATA

GACTTTTTTGTTTACATTATAGAAAAAGAAGGAGAGGTTATTTTCTTGCA

TTTATTCATGATTGAGTATTCTATTTTGATTTTGTATTTGTTTGATAT

Primer Binding Domain (PBD) was designed as described by Friant et al., ((1998) Mol. Cellul. Biology, 18: 799-806) and amplified by PCR using the set of following overlapping primers:

AS830 SEQ ID NO. 25
CCGCGGTATCTCACATTCACCCAATTGTCATGGTT

AS831 SEQ ID NO. 26
TTAGAAGTATCCTGTGCACATCCGCAACCATGACAATTGG

AS832 SEQ ID NO. 27
ACAGGATACTTCTAAGGAAGTCCACACAAATCAAGAACCCTTAGA

AS833 SEQ ID NO. 28
TCACATTCTTCTGTTTTGGTAGCTGAAACGTCTAAGGGTTCTTGA

AS834 SEQ ID NO. 29
CAGAAGAATGTGAGAAGGCTTCCACTAAGGCTAACTCTCAACAG

AS835 SEQ ID NO. 30
CGCGGCCGCGTTGTCTGTTGAGAGTTAGC

PBD sequence SEQ ID NO. 31
CCGCGGTATCTCACATTCACCCAATTGTCATGGTTGCGGATGTGCACAGG

ATACTTCTAAGGAAGTCCACACAAATCAAGAACCCTTAGACGTTTCAGCT

ACCAAAACAGAAGAATGTGAGAAGGCTTCCACTAAGGCTAACTCTCAACA

GACAACGCGGCCGC

LtrA gene from *Lactococcus lactis* encoded by the LtrB intron was synthesised by commercial DNA synthesis provider. The sequence of the LtrA protein was first optimised for codon usage in plants and 5 plant introns were inserted into the coding sequence to improve LtrA expression in plants. Plant introns inserted in the coding sequence of LtrA gene are underlined and shown in bold letters. The introns 1, 2 4 are from *Arabidopsis* gene At5g01290, intron 3 and 5 were selected from *Arabidopsis* gene At5g43940. The clone was named as LtrASi.

LtrASi gene sequence: SEQ ID NO. 32
GCATGCATGAAGCCAACAATGGCAATCCTCGAACGAATCTCTAAGAACTC

ACAGGAGAACATCGACGAGGTACAATAACCCATATATATGAATTGATTCA

TGTGTTACTCGTACTTGTTTGAATATGTTTGGAGCAAGTTTGATACTTTT

-continued

GGATGATGATATCGCAAATTCGTTATCTTTTTGGCGTTATAGGTCTTCAC

AAGACTTTACCGTTACCTTCTCCGTCCTGACATCTACTACGTGGCATATC

AGAACCTCTACTCTAACAAGGGAGCTTCTACAAAGGGAATCCTCGATGAT

ACAGCTGATGGATTCTCTGAGGAGAAGATCAAGAAGATCATCCAATCTTT

GAAGGACGGAACTTACTACCCTCAGCCTGTCCGAAGAATGTACATCGCAA

AGAAGAACTCTAAGAAGATGAGACCTCTTGGAATCCCAACTTTCACAGAC

AAGTTGATCCAGGAGGCTGTGAGAATCATCCTTGAATCTATCTATGAGCC

TGTCTTCGAGGATGTGTCTCACGGTTTCCGACCTCAGCGAAGCTGTCACA

CAGCTTTGAAGACAATCAAGAGAGAGTTCGGAGGTAAATTATATGCTTTG

CCACTTCCTCAAAAGATCATTTTAGGTTCATTGGTATGTGGTTTTTTTCT

TAACAGGTGCAAGATGGTTCGTGGAGGGAGATATCAAGGGATGCTTCGAT

AACATCGACCACGTCACACTCATCGGACTCATCAACCTTAAGATCAAGGA

TATGAAGATGAGCCAGTTGATCTACAAGTTCCTCAAGGCAGGTTACCTCG

AAAACTGGCAGTACCACAAGACTTACAGCGGAACACCTCAGGGCGGAATC

CTCTCTCCTCTCCTCGCTAACATCTATCTTCATGAATTGGACAAGTTCGT

TCTCCAACTCAAGATGAAGTTCGACCGAGAGAGTCCAGAGAGAATCACAC

CTGAATACCGGGAGCTTCACAACGAGATCAAAAGAATCTCTCACCGTCTC

AAGAAGTTGGAGGGCGAGGAGAAGGCTAAGGTTCTCTTGGAATACCAGGA

GAAGAGGAAGAGGTTGCCTACACTCCCTTGTACATCACAAACAAACAAGG

TTCGTTCTCTCCATTTTCATTCGTTTGAGTCTGATTTAGTGTTTTGTGGT

TGATCTGAATCGATTTATTGTTGATTAGTGAATCAATTTGAGGCTGTGTC

CTAATGTTTTGACTTTTGATTACAGGTCTTGAAGTACGTCCGATACGCTG

ACGACTTCATCATCTCTGTTAAGGGAAGCAAGGAGGACTGTCAATGGATC

AAGGAGCAATTGAAGCTCTTCATCCATAACAAGCTCAAGATGGAATTGAG

TGAGGAGAAGACACTCATCACACATAGCAGTCAGCCTGCTCGTTTCCTCG

GATACGACATCCGAGTCAGGAGAAGTGGAACTATCAAGCGATCTGGAAAG

GTTCAATTCTTTCTTTCACATTTGTACTTGTTCACTCGTTTTATTAATCC

TCTTTAGAATGGAGATTCTTACCTCTGTGTGGCCTTTGGCAGGTCAAGAA

GAGAACACTCAACGGGAGTGTGGAGCTTCTCATCCCTCTCCAAGACAAGA

TCCGTCAATTCATCTTCGACAAGAAGATCGCTATCCAGAAGAAGGATAGC

TCATGGTTCCCAGTTCACAGGAAGTACCTTATCCGTTCAACAGACTTGGA

GATCATCACAATCTACAACTCTGAATTGAGAGGTAAGCTGCTACCTCAAA

CTTTCTAGTGCTTCCATATTTCCTTTCTTCTGCAAGGCAGAGAACCATTG

TGGTTAAGTGTTTTAAATTGTGAATGTATAGGTATCTGCAACTACTACGG

TCTCGCAAGTAACTTCAACCAGCTCAACTACTTCGCTTACCTTATGGAAT

ACTCTTGCTTGAAGACTATCGCATCTAAGCATAAGGGAACACTCTCAAAG

ACCATCTCTATGTTCAAGGATGGAAGTGGTTCTTGGGGAATCCCTTACGA

GATCAAGCAGGGGAAGCAGAGGAGATACTTCGCCAACTTCAGTGAATGCA

AATCTCCTTACCAATTCACTGATGAGATCAGTCAAGCTCCTGTGCTTTAC

GGATACGCTCGGAACACTCTTGAGAACAGACTTAAGGCTAAGTGTTGTGA

-continued

GCTTTGTGGAACATCTGATGAGAACACATCTTACGAGATCCACCACGTCA

ACAAGGTCAAGAACCTTAAGGGAAAGGAGAAGTGGGAGATGGCAATGATC

GCTAAGCAGCGGAAGACTCTTGTTGTTTGCTTCCATTGTCATCGTCACGT

GATCCATAAGCACAAGTGAACTAGTAA

The LtrA gene was translationally fused to the chloroplast transit peptide (rbcS-cTP) from tobacco Rubisco small sub-unit gene (Bank Access. No. AY220079) which was amplified using the following PCR primers:

AS794 SEQ ID NO. 33
GCTCGAGACAATGGCTTCCTCAGTTCTTTCCTCT

AS639 SEQ ID NO. 34
CGCATGCTACCTGCATACATTGCACTCTTCCACCAT rbcS-cTP sequence SEQ ID NO. 34
CTCGAGACAATGGCTTCCTCAGTTCTTTCCTCTGCAGCAGTTGCCACTCG

CACCAATGTTGCTCAAGCTAACATGGTTGCACCTTTCACTGGTCTTAAGT

CAGCTGCCTCATTCCCTGTTTCAAGGAAGCAAAACCTTGACATCACTTCC

ATTGCTAGCAATGGTGGAAGAGTGCAATGTATGCAGGTAGCATGC

The 5' promoter region from *Arabidopsis* ubiquitin 3 gene was amplifies with the following primers:

AS724 SEQ ID NO. 35
CGGTACCTACCGGATTTGGAGCCAAGTC

AS726 SEQ ID NO. 36
GTGTTTGGTGACCTGAAATAAAACAATAGAACAAGT

*Arabidopsis* Ubiq3 promoter sequence SEQ ID NO. 37
TACCGGATTTGGAGCCAAGTCTCATAAACGCCATTGTGGAAGAAAGTCTT

GAGTTGGTGGTAATGTAACAGAGTAGTAAGAACAGAGAAGAGAGAGAGTG

TGAGATACATGAATTGTCGGGCAACAAAAATCCTGAACATCTTATTTTAG

CAAAGAGAAAGAGTTCCGAGTCTGTAGCAGAAGAGTGAGGAGAAATTTAA

GCTCTTGGACTTGTGAATTGTTCCGCCTCTTGAATACTTCTTCAATCCTC

ATATATTCTTCTTCTATGTTACCTGAAAACCGGCATTTAATCTCGCGGGT

TTATTCCGGTTCAACATTTTTTTTGTTTTGAGTTATTATCTGGGCTTAAT

AACGCAGGCCTGAAATAAATTCAAGGCCCAACTGTTTTTTTTTTTAAGAA

GTTGCTGTTAAAAAAAAAAAAAAGGGAATTAACAACAACAACAAAAAAAGA

TAAAGAAAATAATAACAATTACTTTAATTGTAGACTAAAAAAACATAGAT

TTTATCATGAAAAAAAGAGAAAAGAAATAAAAACTTGGATCAAAAAAAAA

ACATACAGATCTTCTAATTATTAACTTTTCTTAAAAATTAGGTCCTTTTT

CCCAACAATTAGGTTTAGAGTTTTGGAATTAAACCAAAAAGATTGTTCTA

AAAAATACTCAAATTTGGTAGATAAGTTTCCTTATTTTAATTAGTCAATG

GTAGATACTTTTTTTTCTTTTCTTTATTAGAGTAGATTAGAATCTTTTAT

GCCAAGTATTGATAAATTAAATCAAGAAGATAAACTATCATAATCAACAT

GAAATTAAAAGAAAAATCTCATATATAGTATTAGTATTCTCTATATATAT

TATGATTGCTTATTCTTAATGGGTTGGGTTAACCAAGACATAGTCTTAAT

GGAAAGAATCTTTTTTGAACTTTTTCCTTATTGATTAAATTCTTCTATAG

AAAAGAAAGAAATTATTTGAGGAAAAGTATATACAAAAAGAAAAATAGAA

-continued

AAATGTCAGTGAAGCAGATGTAATGGATGACCTAATCCAACCACCACCAT

AGGATGTTTCTACTTGAGTCGGTCTTTTAAAAACGCACGGTGGAAAATAT

GACACGTATCATATGATTCCTTCCTTTAGTTTCGTGATAATAATCCTCAA

CTGATATCTTCCTTTTTTTGTTTTGGCTAAAGATATTTTATTCTCATTAA

TAGAAAAGACGGTTTTGGGCTTTTGGTTTGCGATATAAAGAAGACCTTCG

TGTGGAAGATAATAATTCATCCTTTCGTCTTTTTCTGACTCTTCAATCTC

TCCCAAAGCCTAAAGCGATCTCTGCAAATCTCTCGCGACTCTCTCTTTCA

AGGTATATTTTCTGATTCTTTTTGTTTTTGATTCGTATCTGATCTCCAAT

TTTTGTTATGTGGATTATTGAATCTTTTGTATAAATTGCTTTTGACAATA

TTGTTCGTTTCGTCAATCCAGCTTCTAAATTTTGTCCTGATTACTAAGAT

ATCGATTCGTAGTGTTTACATCTGTGTAATTTCTTGCTTGATTGTGAAAT

TAGGATTTTCAAGGACGATCTATTCAATTTTTGTGTTTTCTTTGTTCGAT

TCTCTCTGTTTTAGGTTTCTTATGTTTAGATCCGTTTCTCTTTGGTGTTG

TTTTGATTTCTCTTACGGCTTTTGATTTGGTATATGTTCGCTGATTGGTT

TCTACTTGTTCTATTGTTTTATTTCAGGTCACCAAACA

The nos terminator fragment was synthesised based on gene bank sequence accession EU048864.

nos terminator sequence SEQ ID NO. 38
TCTAGAGTCAAGCAGATCGTTCAAACATTTGGCAATAAAGTTTCTTAAGA

TTGAATCCTGTTGCCGGTCTTGCGATGATTATCATATAATTTCTGTTGAA

TTACGTGAAGCATGTAATAATTAACATGTAATGCATGACGTTATTTATGA

GATGGGTTTTTATGATTAGAGTCCCGCAATTATACATTTAATACGCGATA

GAAAACAAAATATAGCGCGCAAACTAGGATAAATTATCGCGCGCGGTGTC

ATCTATGTTACTAGATCGACCTGCAG

The reverse transcriptase-RNase H gene from yeast Ty1-H3 clone (Boeke et al., Mol. Cellul. Biology (1988), 8: 1432-1442; bank accession No. M18706) was optimised for codon usage in plants, and by insertion of 5 introns from *Arabidopsis* genome (intron 1—from At1g04820, intron 2—from At2g29550, intron 3—from At1g31810, intron 4 and 5—from At1g09170). The introns are underlined and shown in bold letters. The clone was synthesised by commercial DNA synthesis provider and named as RTRHi-Ty1.

RTRHi-Ty1 sequence SEQ ID NO. 39
ATGAACAATTCATCCCACAACATCGTTCCTATCAAGACTCCAACTACTGT

TTCTGAGCAGAACACTGAAGAATCTATCATCGCTGATCTTCCACTTCCTG

ATCTTCCTCCAGAATCTCCTACTGAATTTCCTGATCCATTCAAAGAACTT

CCACCTATCAACTCAAGACAAACTAACTCTTCATTGGGCGGAATTGGCGA

TTCTAATGCTTACACTACTATCAACTCTAAGAAGAG<u>GTATTGTAGCCAGC</u>

<u>CTCAACCAGTCTTTTTGCTGTTACATTTTCTTGGGCTCATCTAATGTTAT</u>

<u>TTTCCTATTTTGTTTTCAG</u>GTCACTTGAAGATAATGAAACTGAAATCAAA

GTTTCTAGGGATACATGGAATACTAAGAATATGAGATCACTTGAACCTCC

AAGATCTAAGAAGAGAATCCATCTTATTGCAGCTGTTAAAGCTGTGAAAT

-continued

CAATCAAACCAATTAGAACAACTCTTAGATACGATGAAGCAATTACATAC

AACAAAGACATCAAGGAGAAGGAGAAATACATCGAGGCTTACCACAAAGA

AGTTAACCAACTTCTTAAGATGAAAACTTGGGATACTGATGAATACTACG

ATAGAAAAGAGATTGACCCTAAGAGAGTTATCAACTCAATGTTCATCTTC

AACAAGAAGAGAGACGGAACTCACAAAGCTAGATTCGTTGCAAGAGGAGA

TATTCAGCATCCTGACACTTACGATTCAGGTAAGTATTCCAATGTTCTTC

GATTATGAGTCAATGTTGTTACTGTATCTGTCTCTGTGGTTTATTGTTTC

AGGCTTAGTTATTGATTAGTATTGAAACTTCACTCACATATTTTTTTGTT

TGTTTTCTGAATTGTGCAGGTATGCAATCTAATACTGTTCATCACTACGC

ATTGATGACATCTCTTTCACTTGCATTGGACAATAACTACTACATTACAC

AACTTGACATATCTTCTGCATACCTTTACGCTGATATCAAGGAGGAGCTT

TACATTAGACCTCCACCACATTTGGGAATGAATGATAAGTTGATCCGTTT

GAAGAAATCACTTTACGGATTGAAACAATCTGGAGCTAATTGGTACGAAA

CTATCAAATCATACCTTATTCAGCAATGCGGTATGGAGGAAGTTAGGGGA

TGGTCATGCGTATTCAAGAACTCTCAAGTTACAATCTGCCTCTTCGTTGA

TGATATGGTGCTCTTCTCTAAGAATCTTAACTCAAACAAGAGAATCATTG

AGAAGTTGAAGATGCAATACGACACTAAGATCATCAACCTTGGAGAATCT

GATGAGGAAATTCAATACGACATTCTTGGATTGGAAATCAAATACCAAAG

AGGTGAGTTATATTTAACAGCTCATCAGTTACTTAAACACTTTTTGGGAC

AAGCAGTTCAAACTCATGTTCCAATCCTAAAATTAATTGCAATTCACAGG

TAAGTACATGAAGTTGGGAATGGAAAACTCATTGACTGAGAAGATTCCTA

AACTTAACGTTCCTTTGAATCCAAAGGGAAGAAAGCTCTCTGCTCCAGGA

CAACCAGGACTTTACATTGACCAGGATGAACTTGAGATTGATGAGGATGA

ATACAAGGAGAAAGTACACGAGATGCAGAAGTTGATTGGACTTGCTTCAT

ACGTTGGATACAAATTCAGATTCGACCTTCTTTACTACATCAACACACTT

GCTCAGCATATACTTTTCCCATCTAGGCAAGTTCTTGACATGACATACGA

GCTTATCCAATTCATGTGGGACACTAGAGACAAGCAACTCATATGGCACA

AGAACAAGCCTACAGAGCCAGATAACAAGCTCGTTGCAATCTCTGATGCT

TCTTACGGAAACCAACCATACTACAAATCACAAATTGGAAACATCTACTT

GCTTAACGGAAAGGTACTTTTCTCAAAGACTTTACCTTATTGTGGAATAT

TGAATTTTCTGAAAGACTTCACCTTATCTACATTTGTAATTTTACTATGG

TAATCAGGTGATTGGAGGAAAGAGCACTAAGGCTTCACTTACATGCACTT

CAACTACTGAGGCAGAGATCCACGCTATATCAGAATCTGTACCACTTCTT

AACAACCTTTCTTACCTTATCCAAGAGCTTAACAAGAAGCCAATCATCAA

GGGACTTCTTACTGACTCAAGATCAACAATCTCTATCATTAAGTCTACAA

ATGAAGAGAAATTCAGAAACAGATTCTTCGGAACAAAGGCAATGAGACTT

AGAGATGAAGTTTCAGGTAAGTATTAACTTACCAAATGATCAATATTATT

TTGAAATGCAGGTTTTAGAATAATACTCTCTGCCGTTCTTGTTTATTTCC

AGGTAACAACCTTTACGTTTACTACATCGAGACTAAGAAGAACATTGCTG

ACGTTATGACAAAGCCTCTTCCTATCAAGACCTTCAAGTTGCTTACTAAC

AAATGGATTCATTAA

The RT-RH-Ty1 sequence was translationally fused to the chloroplast transit peptide from pea chloroplast HSP60 heat shock protein (Accession No. L03299). The sequence for the transit peptide (HSP60-cTP) was amplified from pea genomic DNA using the following PCR primers:

AS293 SEQ ID NO. 40
TCTCGAGTTGATGGCTTCTTCTGCTCAAATA

AS294 SEQ ID NO. 41
GGCATGCAACTCTCAAAGTGAAACCCTTC

HSP60-cTP sequence SEQ ID NO. 42
CTCGAGATGGCTTCTTCTGCTCAAATACACGGTCTCGGAACCGCTTCTTT

CTCTTCCCTCAAAAAACCCTCTTCCATTTCCGGTAATTCCAAAACCCTTT

TCTTCGGTCAGCGACTCAATTCCAACCACTCTCCCTTCACCCGCGCCGCA

TTCCCTAAGTTAAGTAGCAAAACCTTTAAGAAGGGTTTCACTTTGAGAGT

TGCATGC

The expression of the RTRHi-Ty1 and HSP60-cTP fusion was driven by TAF2 promoter from *Arabidopsis* taf2 gene. It was amplified from *Arabidopsis* genomic DNA (Col-0) using the following set of primers:

AG3 SEQ ID NO. 43
GGTACCATGATCGCTTCATGTTTTTATC

AG4 SEQ ID NO. 44
CTCGAGGTTCCTTTTTTGCCGATATGTTAG

TAF2 promoter sequence SEQ ID NO. 45
GTACCATGATCGCTTCATGTTTTTATCTAATTTGTTAGCATATTGAATGA

TTGATTTTCTTTTAATTTGGATATGTTGATTGTCTTGTTGCATCATCAAT

GTATGTTTTATTTAACACCGGAAGATCTTATGATGGGTTCATTACTTCAT

AATAATCTCCGAGTTCTACAAGACTACAACTTTCACGTGACTTTTACAGC

GACAAAAAAATGCATCTAGCGAAAATTAATCCACAACCTATGCATTTTTGT

CACTCTTCACACGCGTATGTGCATAAATATATAGTATATACTCGACAATC

GATGCGTATGTGTACACAATTACCAAAACAATTATTTGAATATTCAGACA

TGGGTTGACATCACCAAGTAATATTCACAGTATCTGAAAACTATGTTTTG

ACATCCCTAAATAGTTTGACTAACCAGTTTAATATGAGAGCATTTGTAAG

AGGCAAGAGCCATGGTTTTGTTGGCTCGTTTAATATGCTCATTTAACCCC

CCCAAAAAATACTATTAGATTTAAACGTAAAAGAATTAACGAACACAAGA

ACTGCTAAAACAAAAAAAAATCAATGGCCGACATTTCATAGTTCATACAT

CACTAATACTAAAAGATGCATCATTTCACTAGGGTCTCATGAAATAGGAG

TTGACATTTTTTTTGTAACGACAGAAGTTGACATGTTAAGCATCAATTT

TTTTAAGAGTGGATTATACTAGTTTTTTTTTTTTTTTTTAATGTATGGTA

TGATACAACAACAAAAACTATAAAATAGAAAAAGTCAGTGAAACCTCAAA

TTGAAGGAAAAACTTTTGCACAAAAAGAGAGAGAGAGAGAAAGAATGTAA

ATCCAAATAAATGGGCCTAATTGAGAATGCTTTAACTTTTTTTTTTTGGC

TAAAAGAGAATGCTTTAACTAAGCCCATAAAATGAACATCAAACTCAAAG

GGTAAGATTAATACATTTAGAAAACAATAGCCGAATATTTAATAAGTTTA

AGACATAGAGGAGTTTTATGTAATTTAGGAACCGATCCATCGTTGGCTGT

ATAAAAAGGTTACATCTCCGGCTAACATATCGGCAAAAAAGGAACCTCGA

G

The agropine synthase polyA signal (ags terminator) was synthesized based on the gene bank sequence EU181145.

```
The ags terminator sequence             SEQ ID No. 46
GAATTAACAGAGGTGGATGGACAGACCCGTTCTTACACCGGACTGGGCGC

GGGATAGGATATTCAGATTGGGATGGGATTGAGCTTAAAGCCGGCGCTGA

GACCATGCTCAAGGTAGGCAATGTCCTCAGCGTCGAGCCCGGCATCTATG

TCGAGGGCATTGGTGGAGCGCGCTTCGGGGATACCGTGCTTGTAACTGAG

ACCGGATATGAGGCCCTCACTCCGCTTGATCTTGGCAAAGATATTTGACG

CATTTATTAGTATGTGTTAATTTTCATTTGCAGTGCAGTATTTTCTATTC

GATCTTTATGTAATTCGTTACAATTAATAAATATTCAAATCAGATTATTG

ACTGTCATTTGTATCAAATCGTGTTTAATGGATATTTTTATTATAATATT

GATGAT
```

Plant Transformation

Transformation of *Arabidopsis* Plants

Transformation of *Arabidopsis* plants was performed as described by Clough & Bent (Clough & Bent (1998) Plant Journal 16:735-743). *Agrobacterium tumefacience* strain GV3101 (Koncz & Schell (1986) Mol Gen Genet 204:383-396) was used for transformation. Transformation of plants was carried out with chloroplast transformation constructs (FIG. 2) based on the pGreen 0029 binary vector (Hellens et al (2000) Plant Mol. Biol 42: 819-832). In brief, a chloroplast transformation cassette containing trnI flank, Prrn promoter, aadA gene, psbA 3' UTR, trnA flank and primer binding domain (PBD) was inserted into domain IV of the LtrB or fused to CTL from ASB using AscI-NotI enzymes. The resulting DNA fragment was fused to the 35S promoter and nos terminator and introduced into the pGreen0029 binary vector (EU048864). The fragment of LtrASi was fused to a chloroplast transit peptide (rbcS-cTP) and ubiq3 promoter from *Arabidopsis*. Resulting cassette was inserted into pGreen 0029 together with the chloroplast transformation cassette. The reverse transcriptase-RNase H (RTRHi-Ty1) was fused to HSP60-cTP transit peptide, TAF2 promoter and ags terminator. The resulted cassette was inserted in pSOUP vector (EU048870) carrying T-DNA from pGreen0179 vector (EU048866). The construct carrying the chloroplast cassette and LtrASi was co-transform with construct carrying RTRHi-Ty1 cassette in the same stain of *Agrobacterium* and used for *Arabidopsis* (Col-0) transformation.

Transgenic lines were recovered on selection medium supplemented with 100 mg/l of spectinomycin.

Transformation of Tobacco Plants

Tobacco plants were transformed as described by Horsch et al., (1985) Science 227: 1229-1231, using *Agrobacterium* strain AGL1 (see protocol, below).

The constructs were similar to the constructs used for *Arabidopsis* transformation with exception that trnI and trnA flanking sequences of the chloroplast cassette were amplified from tobacco genomic DNA (FIG. 2).

Transgenic tobacco plants were regenerated on selection medium supplemented with 500 mg/l of spectinomycin.

Transformation of Tobacco Leaf Explants with *Agrobacterium* Strain AGL1

All items are autoclave-sterilised prior to use.

Filter sterilize antibiotics to prevent fungal growth, keep antibiotics for plant tissue culture in separate box Sterilize plant material: take plants of about 9 cm high, they should not have started to flower. Cut leaves with cuticle (4-6 leaves per construct, enough to cut 100 explants), dip in 70% Ethanol and immediately dip in 1% Na-hypochlorite (cat. No 01032500; use bottle of bleach that is no more than 3 months old because the chlorine gas evaporates), hold leaves with forceps and stir in for 20 min. Avoid damaging the cuticle otherwise bleach will enter the vascular system. Rinse briefly in sterile water 5-6 times and leave in water until ready to be cut.

Co-cultivation of agro with tobacco explants: grow AGL1 in LB or L broth with appropriate antibiotics overnight at 28-30° C., the next day re-suspend agro in co-cultivation solution so that the final concentration is around 0.4-0.6 $OD_{600\ nm}$. Place tobacco leaves in co-culture broth and cut squares of 1-1.5 cm×1-1.5 cm with a rounded sterile scalpel using a rolling action. Dip the leaf explants in the agro solution with sterile forceps (stored in 100% ethanol, flamed and let to cool prior to touching the leaf tissue) blot on sterile Whatman paper and transfer on non-selective TSM plates (6 explants per plate) need to prepare about 15 plates per construct. Repeat this procedure for each construct, making sure that the scalpel and forceps, are dipped in ethanol and flamed between each construct to prevent cross-contamination. Leave for 2 days only for AGL1 (3-4 days for other agro strains)

Transfer on selective TSM plates: use sterile flamed forceps to pick up and wash explants in 100 mls co-cultivation broth supplemented with timentin 320 mg/l (one pot per construct), shake well, blot on sterile whatman paper and place the washed explants on selective TSM plates supplemented with appropriate selective antibiotics and timentin 320 mg/l to kill *agrobacterium.*

Shoot regeneration: takes around 1 month to see shoots appear, explants should be transferred on fresh plates every 10-14 days. Watch out for AGL1 recurrent growth, if Timentin is not enough to kill agro, add cefotaxime at 250 mg/l.

Root regeneration: Takes around 1 week. Shoots are cut from the explants and place in growth boxes containing TRM supplemented with the appropriate selective antibiotics and timentin 320 mg/l+cefotaxime 250 mg/l to prevent *agrobacterium* recurrent growth.

Maintain plants in TRM boxes: sub them every two weeks until ready to be transferred into glasshouse Adaptation to glasshouse conditions: soak peat pellets in sterile water until they swell to normal size and carefully place one plant per pellet, incubate the plants under 100% humidity conditions in a propagator, gradually opening the little windows until plants adapt to normal atmosphere over several days.

Recipes:

Co-culture: MS with vitamins and MES+0.1 mg/l NAA+1 mg/l BA+3% sucrose, pH 5.7

TSM: MS with vitamins and MES+0.1 mg/l NAA+1 mg/l BA+3% sucrose, pH5.7, 0.2% gelrite TRM: ½ MS salts with vitamins and MES+0.5% sucrose, pH5.7, 0.2% gelrite.

Autoclave.

Antibiotics Concentration

For *Agrobacterium* LB or L Cultures:

To grow AGL1 carrying pGreen/pSOUP: Carbenicillin 100 mg/l, Tetracycline 5 mg/ml, Rifampicin 50 mg/ml, Kanamycin 50 mg/ml AGL1 carrying pSOUP: Carbenicilin 100 mg/l, Tetracycline 5 mg/ml, Rifampicin 50 mg/ml.

AGL1 empty: Carbenicillin 100 mg/l, Rifampicin 50 mg/ml.

For Plant Culture:

Kanamycin: 300 mg/l (100 mg/l if using *benthamiana*)

Hygromycin: 30 mg/l (10 mg/l if using *benthamiana*)

PPT: 20 mg/l (2 mg/l if using *benthamiana*)

Spectinomycin: 500 mg/l

Timentin: 320 mg/l. It is used to kill agro, fairly unstable make up small amount of stock, store in freezer for up to 1 month after that the antibiotic is no more efficient.

Cefotaxime: 250 mg/l. Also used to kill agro, add to TS

PCR Analysis of Transgenic Plants.

The following primers have been used for amplification of flanking junction sequences:

```
LFS1                                    SEQ ID NO. 47
GAGATGTGGATCATCCAAGGCA

RFS1                                    SEQ ID NO. 48
CTACCATAGAGGCCAACGATAG

AS527                                   SEQ ID NO. 49
AACGTCGGTTCGAGATGG (aadA-R1)

aadA-F1                                 SEQ ID NO. 50
CGAAGGATGTCGCTGCCGACT;
```

and nested primers:

```
                                        SEQ ID NO. 51
LFS2       CTCCTCCTCAGGAGGATAGATG

                                        SEQ ID NO. 52
RFS2       AACTTTCATCGTACTGTGCTCTC

                                        SEQ ID NO. 53
AS526      GAGTCGATACTTCGGCGATC(aadA-R2)

                                        SEQ ID NO. 54
aadA-F2    CTAGACAGGCTTATCTTGGACA
```

The following primers were used for amplification of chloroplast probe for Southern hybridisation:

```
LP-F   CGTGTTTAGTTGCCATCGTTGA   SEQ ID NO. 55

LP-R   GCTGAGAGCCCTCACAGCCCA    SEQ ID NO. 56

RP-F   TGTCAGCGGTTCGAGTCCGCTTA  SEQ ID NO. 57

RP-R   TAACCAAGCCACTGCCTATGAGT  SEQ ID NO. 58
```

The following primers were used for amplification of aadA gene as a probe for Northern hybridisation:

```
aadA1   GTGATCGCCGAAGTATCGACT   SEQ ID NO. 59

aadA2   ATCTCGCCTTTCACGTAGTGG   SEQ ID NO. 60
```

Results and Discussion

The transformation of *Arabidopsis* and tobacco with our vectors containing transgene cassettes generated chloroplast transgenic plants by selection on medium supplemented with 100 mg/l of spectinomycin for *Arabidopsis* and 500 mg/l for tobacco (FIG. 2). In all cases we were able to detect insertion of the transgene cassette into the chloroplast genome using PCR amplification of junction regions. Five independent transgenic lines were analysed for all constructs and we could amplify correct size DNA fragment for insertion junctions in all lines. The amplified fragments were sequenced and correct insertion sites were confirmed.

Southern and Northern analysis was also performed to confirm presence of insertion and the chloroplast transcripts.

EXPERIMENTAL SECTION 1B

Modifications of the chloroplast transformation method used in Experimental section 1A can be improved using PBD designed for reverse transcription in the cytoplasm or in plastids, and by re-positioning of the building blocks on the transformation cassette (FIG. 3).

The set of constructs was prepared for tobacco and rice transformation with LtrB intron (LtrB-CTS) or with ASB sequences (ASB-CTS) as the CTS (FIGS. 4-6). The positioning of transgene cassette building blocks was designed as described in FIG. 3, A-B for LtrB-CTS and FIG. 3, C-D for ASB-CTS.

The PBD-CHL was designed as described previously.

The primer binding domain of the tobacco tnt1 retrotransposon was used as the PBD-CYT, and it was amplified from genomic DNA of tobacco cv Petit Gerard using the following primers:

```
AS912                                   SEQ ID NO. 61
GCCGCGGCTTTATTACCGTGAATATTA

AS913                                   SEQ ID NO. 62
CGCGGCCGCTCTGATAAGTGCAACCTGATT

PBD-CYT                                 SEQ ID NO. 63
CTTTATTACCGTGAATATTATTTTGGTAAGGGGTTTATTCCCAACAACT

GGTATCAGAGCACAGGTTCTGCTCGTTCACTGAAATACTATTCACTGTC

GGTAGTACTATACTTGGTGAAAAATAAAAATGTCTGGAGTAAAGTACGA

GGTAGCAAAATTCAATGGAGATAACGGTTTCTCAACATGGCAAAGAAGG

ATGAGAGATCTGCTCATCCAACAAGGATTACACAAGGTTCTAGATGTTG

ATTCCAAAAAGCCTGATACCATGAAAGCTGAGGATTGGGCTGACTTGGA

TGAAAGAGCTGCTAGTGCAATCAGGTTGCACTTATCAGA
```

In the first case, the PBD-CHL was fused to the 3' end of the LtrB intron (FIG. 3A, FIG. 4A for tobacco and FIG. 5A for rice). As LtrA protein possesses both LtrB-CTS-binding feature and reverse transcription activity it can fulfill both functions of the transgene RNA translocation into plastids and reverse transcription of the RNA cassette using plastid tRNA-Met as a primer.

In the second case, the PBD-CYT was fused to CTU (FIG. 3B, FIG. 4B for tobacco and FIG. 5B for rice), so that reverse transcription of the transgene cassette is initiated and performed by endogenous reverse transcriptases in the cytoplasm using cytoplasmic tRNA-Met. The LtrA protein serves as CTS-binding peptide for translocation of RNA:DNA complex initiated by the reverse transcriptases into the plastids.

The ASB-CTS was fused to the CTU with PBD-CHL or PDB-CYT (FIG. 3, C-D, FIGS. 6, A and B). The reverse transcriptase from yeast ty1 retrotransposon was co-delivered with construct containing PBD-CHL to facilitate reverse transcription reaction in the plastids.

The chloroplast cassette for rice transformation was designed using rice-specific sequences (FIG. 5).

The trnI fragment of the rice chloroplast genome was utilised as the LFS, and it was amplified using the following primers:

```
AS699                                   SEQ ID NO. 64
GGCGCGCCGTGGGATCCGGGCGGTCCG

AS700                                   SEQ ID NO. 65
GGCATGCTGGCGCAGCTGGGCCATCC
```

-continued

```
Rice trnI-LFS                                   SEQ ID NO. 66
Gggatccgggcggtccgggggggggcactacggctcctctcttctcgagaa
tccatacatcccttatcagtgtatggagagctatctctcgagcacaggtt
gaggttcgtcctcaatgggaaaatggagcacctaacaacgcatcttcaca
gaccaagaactacgagatcaccctttcattctggggtgacggagggatcg
taccattcgagcctttttttcatgcttttcccggcggtctggagaaagca
gcaatcaataggacttccctaatcctcccttcctgaaaggaagaacgtga
aattctttttcctttccgcagggaccaggaggttggatctagccataaga
ggaatgcttggtataaataagccacttcttggtcttcgactccctaagtc
actacgagcgccctcgatcagtgcaatgggatgtggctatttatctatct
cttgactcgaaatgggagcagagcaggtttgaaaaaggatcttagagtgt
ctagggttgggccaggagggtctcttaacgccttcctttttctgcccatc
ggagttatttcccaaggacttgccatggtaagggggagaaggggaagaag
cacacttgaagagcgcagtacaacggagagttgtatgctgcgttcgggaa
ggatgaatcgctcccgaaaaggagtctattgattctctcccaattggttg
gatcgtaggggcgatgatttacttcacgggcgaggtctctggttcaagtc
caggatggcccagctgcgcca
```

The trnA fragment of the rice chloroplast genome was used as the RFS, and it was amplified using following primers:

```
AS701                                           SEQ ID NO. 67
gatatcggatggcccagctgcgcca

AS702                                           SEQ ID NO. 68
Gcggccgcattgcccttctccgaccct

Rice trnA-RFS                                   SEQ ID NO. 69
Ggatggcccagctgcgccagggaaaagaatagaagaagcatctgactctt
tcatgcatactccacttggctcggggggatatagctcagttggtagagct
ccgctcttgcaattgggtcgttgcgattacgggttggctgtctaattgtc
caggcggtaatggtagtatcttgtacctgaaccggtggctcactttttct
aagtaatggggaagaggactgaaacatgccactgaaagactctactgaga
caaaaagatgggctgtcaaaaaggtagaggaggtaggatgggcagttggt
cagatctagtatggatcgtacatggacgatagttggagtcggcggctctc
ctaggcttccctcatctgggatccctggggaagaggatcaagttggccct
tgcgaatagcttgatgcactatctcccttcaaccctttgagcgaaatgtg
gcaaaaggaaggaaaatccatggaccgaccccattatctccaccccgtag
gaactacgagatcaccccaaggacgccttcggcgtccaggggtcacggac
cgaccatagaccctgttcaataagtggaacacattagccgtccgctctcc
ggttgggcagtaagggtcggagaagggcaat
```

The chloroplast-specific rrn16 promoter from wheat cv. Pavon was amplified using PCR with the following primers:

```
AS518                                           SEQ ID NO. 70
TATCGATAACATTCCTCTAATTTCATTGCA
```

-continued

```
AS720                                           SEQ ID NO. 71
GGCATGCAGGCTTGTGGGATTGACGTGATAG

Wheat rrn promoter sequence (Wrrn)              SEQ ID NO. 72
Aggcttgtgggattgacgtgatagggtagggttggctatactgctggtg
gcgaactccaggctaataatctgaagcgcatggatacaagttatccttg
gaaggaaagacaattccgaatctgctttgtctacgaataaggaagctat
aagtaatgcaactatgaatctcatg

aadA-mGFP4 fusion sequence
                                                SEQ ID NO. 73
atggcagaagcggtgatcgccgaagtatcgactcaactatcagaggtag
ttggcgtcatcgagcgccatctcgaaccgacgttgctggccgtacattt
gtacggctccgcagtggatggcggcctgaagccacacagtgatattgat
ttgctggttacggtgaccgtaaggcttgatgaaacaacgcggcgagctt
tgatcaacgaccttttggaaacttcggcttcccctggagagagcgagat
tctccgcgctgtagaagtcaccattgttgtgcacgacgacatcattccg
tggcgttatccagctaagcgcgaactgcaatttggagaatggcagcgca
atgacattcttgcaggtatcttcgagccagccacgatcgacattgatct
ggctatcttgctgacaaaagcaagagaacatagcgttgccttggtaggt
ccagcggcggaggaactctttgatccggttcctgaacaggatctatttg
aggcgctaaatgaaaccttaacgctatggaactcgccgcccgactgggc
tggcgatgagcgaaatgtagtgcttacgttgtcccgcatttggtacagc
gcagtaaccggcaaaatcgcgccgaaggatgtcgctgccgactgggcaa
tggagcgcctgccggcccagtatcagcccgtcatacttgaagctagaca
ggcttatcttggacaagaagaagatcgcttggcctcgcgcgcagatcag
ttggaagaatttgtccactacgtgaaaggcgagatcaccaaggtagtcg
gcaaatcaggatccatgagtaaaggagaagaacttttcactggagttgt
cccaattcttgttgaattagatggtgatgttaatgggcacaaattttct
gtcagtggagagggtgaaggtgatgcaacatacggaaaacttaccctta
aatttatttgcactactggaaaactacctgttccatggccaacacttgt
cactactttctcttatggtgttcaatgcttttcaagatacccagatcat
atgaagcggcacgacttcttcaagagcgccatgcctgagggatacgtgc
aggagaggaccatcttcttcaaggacgacgggaactacaagacacgtgc
tgaagtcaagtttgagggagacaccctcgtcaacaggatcgagcttaag
ggaatcgatttcaaggaggacggaaacatcctcggccacaagttggaat
acaactacaactcccacaacgtatacatcatggcagacaaacaaaagaa
tggaatcaaagttaacttcaaaattagacacaacattgaagatggaagc
gttcaactagcagaccattatcaacaaaatactccaattggcgatggcc
ctgtccttttaccagacaaccattacctgtccacacaatctgccctttc
gaaagatcccaacgaaaagagagaccacatggtccttcttgagtttgta
acagctgctgggattacacatggcatggatgaactatacaaataatcta
ga
```

atpA terminator was amplified from wheat DNA using the following primers:

AS753 SEQ ID NO. 74
Accgcggtcaaataaattttgcatgtcta

AS723 SEQ ID NO. 75
Gatatctccatactccttctttatgata

Wheat atpA terminator SEQ ID NO. 76
Caaataaattttgcatgtctactcttgttagtagaataggaatcgttga gaaagatttttcatttgaatcatgcaaaaaagttttctttgtttttagt ttagtatagttatttaaagaatagatagaaataagattgcgtccaatag gatttgaacctataccaaaggtttagaagacctctgtcctatccattag acaatggacgcttttctttcatattttattctttcttttatttttttt cttcttccgagaaaaaactgttagaccaaaactcttttaggaaatcaaa aaatccagatacaaatgcatgatgtatatattatatcatgcatatatca taaagaaggagtatgga The LtrA gene was driven by actin1 rice promoter amplified using the following primers:

ARP1 SEQ ID NO. 77
gtcattcatatgcttgagaaga

ARP2 SEQ ID NO. 78
gcctacaaaaaagctccgcacg

Rice act1 promoter sequence SEQ ID NO. 79
gtcattcatatgcttgagaagagagtcgggatagtccaaaataaaacaa aggtaagattacctggtcaaaagtgaaaacatcagttaaaaggtggtat aagtaaaatatcggtaataaaaggtggcccaaagtgaaatttactcttt tctactattataaaaattgaggatgttttgtcggtactttgatacgtca tttttgtatgaattggtttttaagtttattcgcgatttggaaatgcata tctgtatttgagtcggtttttaagttcgttgcttttgtaaatacagagg gatttgtataagaaatatctttaaaaaacccatatgctaatttgacata atttttgagaaaaatatatattcaggcgaattccacaatgaacaataat aagattaaaatagcttgcccccgttgcagcgatgggtatttttttctagt aaaataaaagataaacttagactcaaaacatttacaaaaacaaccccta aagtcctaaagcccaaagtgctatgcacgatccatagcaagcccagccc aacccaacccaacccaacccaccccagtgcagccaactggcaaatagtc tccacccccggcactatcaccgtgagttgtccgcaccaccgcacgtctc gcagccaaaaaaaaaaaaagaaagaaaaaaaagaaaaagaaaaacagca ggtgggtccgggtcgtgggggccggaaaagcgaggaggatcgcgagcag cgacgaggcccggccctccctccgcttccaaagaaacgccccccatcgc cactatatacatacccccccctctcctcccatcccccccaaccctaccac caccaccaccaccacctcctcccccctcgctgccggacgacgagctcct ccccccctcccccctccgccgccgccggtaaccaccccgcccctctcctct ttctttctccgtttttttttttcgtctcggtctcgatctttggccttggt agtttgggtgggcgagagcggcttcgtcgcccagatcggtgcgcgggag gggcgggatctcgcggctggcgtctccgggcgtgagtcggcccggatcc tcgcggggaatggggctctcggatgtagatctgcgatccgccgttgttg -continued ggggagatgatgggggtttaaaatttccgccatgctaaacaagatcag gaagaggggaaaagggcactatggtttatatttttatatatttctgctg cttcgtcaggcttagatgtgctagatcttctttctttcttctttttgtg gtagaatttgaatccctcagcattgttcatcggtagtttttcttttcat gatttgtgacaaatgcagcctcgtgcggagctttttgtaggc Transformation of Rice Immature Embryos.

Immature Embryo Excision

Day 1:

Remove milky/post-milky stage immature seeds from panicles (immature embryos 1-2 mm in size are desired).

Sterilize immature seeds: 50% sodium hypochlorite (12%)+1 drop of tween 20. Shake 10 min.

Rinse 3-5× in sterile deionised, water. Drain off surplus water. Aliquot seeds (around 40) in sterile Petri dishes.

Set up a 60×15 mm Petri dish containing a 50% sodium hypochlorite solution and next to this a sterile beaker on its side with a sterile filter paper in it. Use sterile forceps to aseptically remove glumes from the first seed. Immerse this seed in the 50% sodium hypochlorite. Remove glumes from a second seed and immerse the second seed into the sodium hypochlorite solution whilst removing the first seed and storing this dehusked/sterilized seed on the filter paper in the beaker. Continue in this manner with all seeds.

After all the glumes are removed:

Sterilize dehusked seeds: 50% sodium hypochlorite: 5 min. with agitation.

Rinse: 5-7× in sterile deionized water, drain.

Place all seeds in a large sterile Petri dish. Aliquot for embryo excision (to keep seeds from drying out, work with only 50-100 in the plate at a time leaving the rest in the master plate).

Remove the embryo from each seed and place embryo, scutellum up, in a 90×15 mm Petri dish containing proliferation medium (40-50 embryos/plate). Culture at 28 e C in the dark for 2 days prior to bombardment Day 3:

Check Each Embryo for Contamination Before Blasting

Remove the embryos from the proliferation medium. Distribute 35-40 embryos scutellum upwards in an area 1 $cm^2$ in the centre of a 60×15 mm target plate containing 10 ml of proliferation medium+osmoticum (0.6M). Check each target plate so that the scutellum is straight. Allow enough room so the scutella do not shade each other out.

Bombardment:

| | |
|---|---|
| Gun | 14 kV |
| | Vacuum: 25 inches of Hg |
| $1^{st}$ bombardment | 4 hours after osmoticum treatment |
| $2^{nd}$ bombardment | 4 hours after $1^{st}$ bombardment |

Day 4:

4-16 hours after the 2nd blast transfer immature embryos to proliferation medium without osmoticum. Culture in the dark at 28° C. for 2 days.

Selection:

Day 5:

Aseptically cut out with scissors the germinating shoot. Transfer 16-20 immature embryos to fresh proliferation medium containing 30-50 mg/l Hygromycin (depending on the genotype); culture in the dark at 28° C.; record total number of embryos.

After 10 days carefully remove the callus from the scutellum by breaking it up into 2-10 small pieces; subculture onto fresh proliferation medium+hygromycin. Do not subculture brown tissue and remaining immature embryo which could inhibit further growth of healthy callus.

Subculture every 10 days by selecting healthy tissue: (embryogenic if present) and transfer it to fresh proliferation medium+hygromycin. Remove brown callus as it could be inhibiting to embryogenic callus.

30 to 40 days after bombardment change selection procedure. Instead of eliminating bad-looking tissue keep embryogenic tissue only (eliminate healthy non-embryogenic tissue)

Regeneration:

After 40 to 60 days, transfer established embryogenic callus showing differential growth on proliferation medium+hygromycin to regeneration medium+hygromycin. Culture at 28 e C under low light for 10 days then under high light for 10 additional days. Check plates periodically in the light for the development of embryos and green shoots. As shoots develop it is sometimes beneficial to gently move the developing shoot away from the callus it originated from and remove any dead tissue from the shoot itself to prevent inhibition of growth.

Germination:

Transfer white compact embryos and green shoots initiating roots to the germination medium under high light at 28 e C for 1 to 2 weeks. Check plates periodically. Remove necrotic tissue and divide germinating embryos if necessary.

Results

The analysis of transgenic plants was performed using PCR for insertion flanking sequences using the following primers for tobacco left flank:

```
AS548   ACGGTGAAGTAAGACCAAGCTCAT    SEQ ID NO. 80

AS549   CTAGGTCGGAACAAGTTGATAGGAC   SEQ ID NO. 81
```

right flank:

```
AS550   GGCTATGCCATCCTAAGGTGCTGCT   SEQ ID NO. 82

AS551   CCATGAATGATAAATCATAGATCGAAC; SEQ ID NO. 83
```

for rice left flank:

```
RC1     CCTGACCCGAAGATGTGGATC       SEQ ID NO. 84

RC2     ACATTAGCATGGCGTACTCCT       SEQ ID NO. 85
```

right flank

```
RC3     AACCAGGAACGGGGAGCTCTC       SEQ ID NO. 86

RC4     CGACTCTTTGATCTTAAACTT       SEQ ID NO. 87
```

Internal primers specific for aadA gene:

```
AS526   GAGTCGATACTTCGGCGATC        SEQ ID NO. 88

AS527   AACGTCGGTTCGAGATGG          SEQ ID NO. 89
```

for mGFP gene

```
AS528   TTACCAGACAACCATTACCTGTC     SEQ ID NO. 90

AS529   GCTGGGATTACACATGGCAT        SEQ ID NO. 91
```

The expected size (1.1 kb) of PCR products were obtained for all tobacco constructs (FIG. 7). Sequencing analysis has confirmed junction site between transgene and plastid genome.

Southern analysis has also confirmed transgene insertions into the correct location of the tobacco chloroplast genome (FIG. 8).

Northern analysis indicated presence of transgene transcript in the fraction of the chloroplast RNA (FIG. 9).

The invention claimed is:

1. A method of transforming the plastids in a tobacco or *Arabidopsis* plant cell, the method comprising:

1) introducing into the nucleus of the plant cell a first nucleic acid construct comprising a *Lactococcus lactis* LtrB, an expression cassette comprising a left flanking sequence, a plastid specific promoter, a nucleic acid of interest, a plastid specific terminator, and a right flanking sequence, and a nucleic acid comprising a primer binding domain (PBD) from tobacco tnt1 retrotransposon or yeast Ty1 retrotransposon; and 2) introducing into the nucleus of the plant cell a second nucleic acid construct encoding a first transit peptide operably linked to a *Lactococcus lactis* LtrA protein, wherein the left and right flanking sequences initiate homologous recombination of the expression cassette into a plastid genome;

wherein said first and second nucleic acid constructs are operably linked to a plant nuclear promoter; and wherein the first and second transit peptides are a small subunit of Rubisco or HSP70.

2. A method of transforming the plastids in a tobacco or *Arabidopsis* plant cell, the method comprising:

1) introducing into the nucleus of the plant cell a first nucleic acid sequence comprising a DNA sequence coding for avocado sunblotch viroid (ASB) RNA, an expression cassette comprising a left flanking sequence, a plastid specific promoter, a nucleic acid of interest, a plastid specific terminator, and a right flanking sequence, and a nucleic acid comprising a primer binding domain (PBD) from tobacco tnt1 retrotransposon or yeast Ty1 retrotransposon; and 2) introducing into the nucleus of the plant cell a second nucleic acid sequence encoding a transit peptide, wherein said transit peptide is from a small subunit of Rubisco or HSP70, operably linked to a reverse transcriptase protein (RTP), wherein said reverse transcriptase protein is selected from the group consisting of retrotransposon encoded reverse transcriptase and retroviral reverse transcriptase, wherein said first and second nucleic acid sequences are operably linked to a plant nuclear promoter.

3. The method according to claim 2, wherein the reverse transcriptase is encoded by a nucleic acid sequence from a yeast retrotransposon Ty1.

4. A method of producing at least a heterologous or exogenous RNA species in a tobacco or *Arabidopsis* plant, the method comprising:

(1) introducing into a regenerable plant cell a first nucleic acid construct comprising a *Lactococcus lactis* LtrB, an expression cassette comprising a left flanking sequence, a plastid specific promoter, a nucleic acid of interest, a plastid specific terminator, and a right flanking sequence, and a nucleic acid comprising a primer binding domain (PBD) from a tobacco tnt1 retrotransposon or a yeast Ty1 retrotransposon; and (2) introducing into the regenerable plant cell a second nucleic acid construct encoding a first transit peptide operably linked a *Lactococcus lactis* LtrA protein (a) wherein said first and second nucleic acid constructs are operably linked to a plant nuclear promoter; and (b) wherein the first and second transit peptides are from a small subunit of Rubisco or HSP70

(3) growing a regenerable plant cell comprising the first and second nucleic acid constructs;

(4) selecting a plant cell of step (3), wherein the expression construct is integrated into the plastid genome;

(5) regenerating a plant from the plant cell of step (4); and (6) growing the plant of step (5), wherein the expression construct that is integrated into the plastid expresses the nucleic acid of interest encoding a heterologous or exogenous protein.

5. A method of producing at least a heterologous or exogenous RNA species in a tobacco or *Arabidopsis* plant, the method comprising:

(1) introducing into a regenerable plant cell a first nucleic acid construct comprising a DNA sequence coding for avocado sunblotch viroid (ASB) RNA, an expression cassette comprising a left flanking sequence, a plastid specific promoter, a nucleic acid of interest, a plastid specific terminator, and a right flanking sequence, and a nucleic acid comprising a primer binding domain (PBD) from tobacco tnt1 retrotransposon or yeast Ty1 retrotransposon;

(2) introducing into the regenerable plant cell a second nucleic acid construct encoding a transit peptide, said transit peptide from a small subunit of Rubisco or HSP70, operably linked to a reverse transcriptase protein (RTP), wherein said reverse transcriptase protein is selected from the group consisting of retrotransposon encoded reverse transcriptase and retroviral reverse transcriptase;

wherein said first and second nucleic acid sequences are operably linked to a plant nuclear promoter;

(3) growing a regenerable plant cell comprising the first and second nucleic acid constructs;

(4) selecting a plant cell of step (3), wherein the expression construct is integrated into the plastid genome;

(5) regenerating a plant from the plant cell of step (4); and (6) growing the plant of step (5), wherein the expression construct that is integrated into the plastid expresses the nucleic acid of interest encoding a heterologous or exogenous protein.

6. A polynucleotide construct that comprises a plant nuclear promoter operably linked to a first nucleic acid sequence comprising a plant plastid translocation sequence wherein said plastid translocation sequence is selected from the group consisting of *Lactococcus lactis* LtrB or avocado sunblotch viroid RNA;

an expression cassette comprising a left flanking sequence, a plastid specific promoter, a nucleic acid of interest, a plastid specific terminator, and a right flanking sequence; and a primer binding domain (PBD) from tobacco tnt1 retrotransposon or yeast Ty1 retrotransposon.

7. A polynucleotide construct that comprises a plant nuclear promoter operably linked to a nucleic acid sequence encoding a plant plastid transit peptide operably linked to a *Lactococcus lactis* LtrA;

wherein said plant plastid transit peptide is from a small subunit of Rubisco or HSP70 proteins.

8. A polynucleotide construct that comprises a plant nuclear promoter operably linked to a nucleic acid sequence encoding a plant plastid transit peptide operably linked to a reverse transcriptase protein, wherein said reverse transcriptase protein is selected from the group consisting of retrotransposon encoded reverse transcriptase and retroviral reverse transcriptase;

wherein said plant plastid transit peptide is from a small subunit of Rubisco or HSP70 proteins; and wherein said plant plastid transit peptide is heterologous with respect to said retroviral reverse transcriptase.

9. A plant comprising the construct according to claim 6.

10. A method of producing a plant, the method comprising incorporating the construct according to claim 9 into an *Arabidopsis* or tobacco plant cell and regenerating a plant from said plant cell.

11. The method according to claim 2, wherein the nucleic acid construct encoding said reverse transcriptase protein is from yeast retrotransposon Ty1 or RNase H.

* * * * *

SEQUENCE LISTING

```
<160> NUMBER OF SEQ ID NOS: 93

<210> SEQ ID NO 1
<211> LENGTH: 980
<212> TYPE: DNA
<213> ORGANISM: Artificial Sequence
<220> FEATURE:
<223> OTHER INFORMATION: Synthetic sequence: LtrB intron sequence

<400> SEQUENCE: 1

ggatccctcg aggtgcgccc agatagggtg ttaagtcaag tagtttaagg tactactcag      60

taagataaca ctgaaaacag ccaacctaac cgaaaagcga aagctgatac gggaacagag     120

cacggttgga aagcgatgag ttagctaaag acaatcggct acgactgagt cgcaatgtta     180

atcagatata agctataagt tgtgtttact gaacgcaagt ttctaatttc ggttatgtgt     240

cgatagagga aagtgtctga aacctctagt acaaagaaag ctaagttatg gttgtggact     300

tagctgttat caccacattt gtacaatctg ttggagaacc aatgggaacg aaacgaaagc     360
```

-continued

```
gatggcgaga atctgaattt accaagactt aacactaact ggggatagcc taaacaagaa    420

tgcctaatag aaaggaggaa aaaggctata gcactagagc ttgaaaatct tgcaaggcta    480

cggagtagtc gtagtagtct gagaaggcta acggccttta catggcaaag ggctacagtt    540

attgtgtact aaaattaaaa attgattagg gaggaaaacc tcaaaatgaa accaacaatg    600

gcaattttag aaagaatcag taaaaattca caagaaaata tagacgaagt ttttacaaga    660

ctttatcgtt atcttttacg tcctgatatt tattacgtgg cgggcgcgcc acgcgtgcgg    720

ccgctgggaa atggcaatga tagcgaaaga acctaaaact ctggttctat gctttcattg    780

tcatcgtcac gtgattcata aacacaagtg aatttttacg aacgaacaat aacagagccg    840

tatactccga gaggggtacg tacggttccc gaagagggtg gtgcaaacca gtcacagtaa    900

tgtgaacaag gcggtacctc cctacttcac catatcattt ttaattctac gaatctttat    960

actggcaaac aatttgactg                                                980


<210> SEQ ID NO 2
<211> LENGTH: 50
<212> TYPE: DNA
<213> ORGANISM: Artificial Sequence
<220> FEATURE:
<223> OTHER INFORMATION: Synthetic sequence: Primer AS839

<400> SEQUENCE: 2

gaactaattt ttttaataaa agttcaccac gactcctcct tctctcacaa                50


<210> SEQ ID NO 3
<211> LENGTH: 50
<212> TYPE: DNA
<213> ORGANISM: Artificial Sequence
<220> FEATURE:
<223> OTHER INFORMATION: Synthetic sequence: Primer AS840

<400> SEQUENCE: 3

taaaaaaatt agttcactcg tcttcaatct cttgatcact tcgtctcttc                50


<210> SEQ ID NO 4
<211> LENGTH: 50
<212> TYPE: DNA
<213> ORGANISM: Artificial Sequence
<220> FEATURE:
<223> OTHER INFORMATION: Synthetic sequence: Primer AS841

<400> SEQUENCE: 4

tgcgagactc atcagtgttc ttcccatctt tccctgaaga gacgaagtga                50


<210> SEQ ID NO 5
<211> LENGTH: 50
<212> TYPE: DNA
<213> ORGANISM: Artificial Sequence
<220> FEATURE:
<223> OTHER INFORMATION: Synthetic sequence: Primer AS842

<400> SEQUENCE: 5

ctgatgagtc tcgcaaggtt tactcctcta tcttcattgt ttttttacaa                50


<210> SEQ ID NO 6
<211> LENGTH: 35
<212> TYPE: DNA
<213> ORGANISM: Artificial Sequence
<220> FEATURE:
<223> OTHER INFORMATION: Synthetic sequence: Primer AS843
```

-continued

<400> SEQUENCE: 6
gggcgcgcca agattttgta aaaaaacaat gaaga 35

<210> SEQ ID NO 7
<211> LENGTH: 29
<212> TYPE: DNA
<213> ORGANISM: Artificial Sequence
<220> FEATURE:
<223> OTHER INFORMATION: Synthetic sequence: Primer AS844

<400> SEQUENCE: 7
gctcgagact tgtgagagaa ggaggagtc 29

<210> SEQ ID NO 8
<211> LENGTH: 180
<212> TYPE: DNA
<213> ORGANISM: Avocado sunblotch viroid

<400> SEQUENCE: 8
gctcgagact tgtgagagaa ggaggagtcg tggtgaactt ttattaaaaa aattagttca 60
ctcgtcttca atctcttgat cacttcgtct cttcagggaa agatgggaag aacactgatg 120
agtctcgcaa ggtttactcc tctatcttca ttgttttttt acaaaatctt gggcgcgccc 180

<210> SEQ ID NO 9
<211> LENGTH: 1331
<212> TYPE: DNA
<213> ORGANISM: Cauliflower mosaic virus

<400> SEQUENCE: 9
caatcccaca aaaatctgag cttaacagca cagttgctcc tctcagagca gaatcgggta 60
ttcaacaccc tcatatcaac tactacgttg tgtataacgg tccacatgcc ggtatatacg 120
atgactgggg ttgtacaaag gcggcaacaa acggcgttcc cggagttgca cacaagaaat 180
ttgccactat tacagaggca agagcagcag ctgacgcgta cacaacaagt cagcaaacag 240
acaggttgaa cttcatcccc aaaggagaag ctcaactcaa gcccaagagc tttgctaagg 300
ccctaacaag cccaccaaag caaaaagccc actggctcac gctaggaacc aaaaggccca 360
gcagtgatcc agccccaaaa gagatctcct ttgccccgga gattacaatg gacgatttcc 420
tctatcttta cgatctagga aggaagttcg aaggtgaagt agacgacact atgttcacca 480
ctgataatga gaaggttagc ctcttcaatt tcagaaagaa tgctgaccca cagatggtta 540
gagaggccta cgcagcaggt ctcatcaaga cgatctaccc gagtaacaat ctccaggaga 600
tcaaatacct tcccaagaag gttaaagatg cagtcaaaag attcaggact aattgcatca 660
agaacacaga gaaagacata tttctcaaga tcagaagtac tattccagta tggacgattc 720
aaggcttgct tcataaacca aggcaagtaa tagagattgg agtctctaaa aaggtagttc 780
ctactgaatc taaggccatg catggagtct aagattcaaa tcgaggatct aacagaactc 840
gccgtgaaga ctggcgaaca gttcatacag agtcttttac gactcaatga caagaagaaa 900
atcttcgtca acatggtgga gcacgacact ctggtctact ccaaaaatgt caaagataca 960
gtctcagaag accaaagggc tattgagact tttcaacaaa ggataatttc gggaaacctc 1020
ctcggattcc attgcccagc tatctgtcac ttcatcgaaa ggacagtaga aaaggaaggt 1080
ggctcctaca aatgccatca ttgcgataaa ggaaaggcta tcattcaaga tctctctgcc 1140
gacagtggtc ccaaagatgg acccccaccc acgaggagca tcgtggaaaa agaagacgtt 1200
ccaaccacgt cttcaaagca agtggattga tgtgacatct ccactgacgt aagggatgac 1260
gcacaatccc actatccttc gcaagaccct tcctctatat aaggaagttc atttcatttg 1320
gagaggacac g 1331

<210> SEQ ID NO 10
<211> LENGTH: 27
<212> TYPE: DNA
<213> ORGANISM: Artificial Sequence
<220> FEATURE:
<223> OTHER INFORMATION: Synthetic sequence: Primer AS699

<400> SEQUENCE: 10
ggcgcgccgt gggatccggg cggtccg 27

<210> SEQ ID NO 11
<211> LENGTH: 26
<212> TYPE: DNA
<213> ORGANISM: Artificial Sequence
<220> FEATURE:
<223> OTHER INFORMATION: Synthetic sequence: Primer AS700

<400> SEQUENCE: 11
ggcatgctgg cgcagctggg ccatcc 26

<210> SEQ ID NO 12
<211> LENGTH: 541
<212> TYPE: DNA
<213> ORGANISM: Nicotiana tabacum

<400> SEQUENCE: 12
ggcgcgccat gggatccggg cggtccgggg gggaccacca cggctcctct cttctcgaga 60
atccatacat cccttatcag tgtatggaca gctatctctc gagcacaggt ttagcaatgg 120
gaaaataaaa tggagcacct aacaacgcat cttcacagac caagaactac gagatcgccc 180
ctttcattct ggggtgacgg agggatcgta ccattcgagc cgttttttttc ttgactcgaa 240 atgggagcag gtttgaaaaa ggatcttaga gtgtctaggg ttgggccagg agggtctctt 300
aacgccttct tttttcttct catcggagtt atttcacaaa gacttgccag ggtaaggaag 360 aagggggggaa caagcacact tggagagcgc agtacaacgg agagttgtat gctgcgttcg 420
ggaaggatga atcgctcccg aaaaggaatc tattgattct ctcccaattg gttggaccgt 480
aggtgcgatg atttacttca cgggcgaggt ctctggttca agtccaggat ggccgcatgc 540
c 541

<210> SEQ ID NO 13
<211> LENGTH: 573
<212> TYPE: DNA
<213> ORGANISM: Arabidopsis thaliana

<400> SEQUENCE: 13
ggcgcgccgt gggatccggg cggtccggag gggaccacta tggctcctct cttctcgaga 60
atccatacat cccttatcag tgtatggaca gctatctctc gagcgcaggt ttaggttcgg 120
cctcaatggg aaaataaaat ggagcaccta acaacgtatc ttcacagacc aagaactacg 180
agatcacccc tttcattctg gggtgacgga gggatcgtac cgttcgagcc tttttttcat 240
gttatctatc tcttgactcg aaatgggagc aggtttgaaa aaggatctta gagtgtctag 300
ggttaggcca gtagggtctc ttaacgccct cttttttctt ctcatcgaag ttatttcaca 360
aatacttcct atggtaacga agaggggggg aacaagcaca cttggagagc gcagtacaac 420

-continued

```
ggagagttgt atgctgcgtt cgggaaggat gaatcgctcc cgaaaaggaa tctattgatt    480

ctctcccaat tggttggacc ataggtgcga tgatttactt cacgggcgag gtctctggtt    540

caaatccagg atggcccagc tgcgccagca tgc                                 573


<210> SEQ ID NO 14
<211> LENGTH: 37
<212> TYPE: DNA
<213> ORGANISM: Artificial Sequence
<220> FEATURE:
<223> OTHER INFORMATION: Synthetic sequence: Primer AS764

<400> SEQUENCE: 14

tgatatcgga tggccctgct gcgccaggga aaagaat                              37


<210> SEQ ID NO 15
<211> LENGTH: 29
<212> TYPE: DNA
<213> ORGANISM: Artificial Sequence
<220> FEATURE:
<223> OTHER INFORMATION: Synthetic sequence: Primer AS845

<400> SEQUENCE: 15

gccgcggatt gcccttctcc gaccctgac                                       29


<210> SEQ ID NO 16
<211> LENGTH: 647
<212> TYPE: DNA
<213> ORGANISM: Nicotiana tabacum

<400> SEQUENCE: 16

gatatcggat ggccctgctg cgccagggaa aagaatagaa gaagcatctg actacttcat     60

gcatgctcca cttggctcgg ggggatatag ctcagttggt agagctccgc tcttgcaatt    120

gggtcgttgc gattacgggt tggatgtcta attgtccagg cggtaatgat agtatcttgt    180

acctgaaccg gtggctcact ttttctaagt aatggggaag aggaccgaaa cgtgccactg    240

aaagactcta ctgagacaaa gatgggctgt caagaacgta gaggaggtag gatgggcagt    300

tggtcagatc tagtatggat cgtacatgga cggtagttgg agtcggcggc tctcccaggg    360

ttccctcatc tgagatctct ggggaagagg atcaagttgg cccttgcgaa cagcttgatg    420

cactatctcc cttcaaccct ttgagcgaaa tgcggcaaaa gaaaaggaag gaaaatccat    480

ggaccgaccc catcatctcc accccgtagg aactacgaga tcaccccaag gacgccttcg    540

gcatccaggg gtcacggacc gaccatagaa ccctgttcaa taagtggaac gcattagctg    600

tccgctctca ggttgggcag tcagggtcgg agaagggcaa tccgcgg                  647


<210> SEQ ID NO 17
<211> LENGTH: 645
<212> TYPE: DNA
<213> ORGANISM: Arabidopsis thaliana

<400> SEQUENCE: 17

gatatcggat ggccctgctg cgccaaggaa aagaatataa gaaggatctg actccttcat     60

gcatgctcca cttggctcgg gggatatagc tcagttggta gagctccgct cttgcaattg    120

ggtcgttgcg attacgggtt gggtgtctaa ttgtccaggc ggtaatgata gtatcttgta    180

cctgaaccgg tggctcactt tttctaagta atggggaaaa ggaccgaaac atgccactga    240

aagactctac tgagacaaag atgggctgtc aagaacgtag aggaggtagg atggtcagtt    300

ggtcagatct agtatggatc gtacatggac ggtagttgga gtcggcggct ctcctagggt    360
```

tccctcgtct gggattgatc cctggggaag aggatcaagt tggcccttgc gaacagcttg 420
atgcactatc tcccttcaac cctttgagcg aaatgcggca aaaggaagga aaatccatgg 480
accgacccca tcgtctccac cccgtaggaa ctacgagatc accccaagga cgccttcggt 540
atccaggggt cgcggaccga ccatagaacc ctgttcaata agtggaatgc attagctgtc 600
cgctcgcagg ttgggcagta agggtcggag aagggcaatc cgcgg 645

<210> SEQ ID NO 18
<211> LENGTH: 30
<212> TYPE: DNA
<213> ORGANISM: Artificial Sequence
<220> FEATURE:
<223> OTHER INFORMATION: Synthetic sequence: Primer AS750

<400> SEQUENCE: 18
ggcatgccgc aatgtgagtt tttgtagttg 30

<210> SEQ ID NO 19
<211> LENGTH: 32
<212> TYPE: DNA
<213> ORGANISM: Artificial Sequence
<220> FEATURE:
<223> OTHER INFORMATION: Synthetic sequence: Primer Prrn-R

<400> SEQUENCE: 19
acttgtatcg atgcgcttca tattcgcccg ga 32

<210> SEQ ID NO 20
<211> LENGTH: 155
<212> TYPE: DNA
<213> ORGANISM: Nicotiana tabacum

<400> SEQUENCE: 20
gcatgccgca atgtgagttt ttgtagttgg atttgctccc ccgccgtcgt tcaatgagaa 60
tggataagag gctcgtggga ttgacgtgag ggggcaggga tggctatatt tctgggagcg 120
aactccgggc gaatatgaag cgcatcgata caagt 155

<210> SEQ ID NO 21
<211> LENGTH: 1237
<212> TYPE: DNA
<213> ORGANISM: Artificial Sequence
<220> FEATURE:
<223> OTHER INFORMATION: Synthetic sequence: aadA gene sequence

<400> SEQUENCE: 21
atggcagaag cggtgatcgc cgaagtatcg actcaactat cagaggtaag taacttttag 60
ctctcagctg ctgtttacta agttcatgcc atacattgat tctggtttat taagggttat 120
gttcagtatt actagtaaca aaatctattt cttcgtttcc gtctgcaggt agttggcgtc 180
atcgagcgcc atctcgaacc gacgttgctg gccgtacatt tgtacggctc cgcagtggat 240
ggcggcctga agccacacag tgatattgat ttgctggtta cggtgaccgt aaggcttgat 300
gaaacaacgc ggcgagcttt gatcaacgac cttttggaaa cttcggcttc ccctggagag 360
agcgagattc tccgcgctgt agaggtaatt ttcatctttg tttggccttc caagtgcttt 420
ttttgctgtt tacgggtgga acttcagtaa aaatgggatc aaaacatcat atggcataaa 480
taaattttaa gaatggcgaa ctcggggtta ccgaatatgg cttccttttt cagtgtttct 540
tagtccattg tacttatgag attgcaggtc accattgttg tgcacgacga catcattccg 600

-continued

```
tggcgttatc cagctaagcg cgaactgcaa tttggagaat ggcagcgcaa tgacattctt    660

gcaggtatct tcgagccagc cacgatcgac attgatctgg ctatcttgct gacaaaagca    720

agagaacata gcgttgcctt ggtaggtcca gcggcggagg aactctttga tccggttcct    780

gaacaggatc tatttgaggc gctaaatgaa accttaacgc tatggaactc gccgcccgac    840

tgggcaggta agaaatcttt tcccatcttg aagtcacctc aaaccgaacg ttaggaaatt    900

ccaaaatgtt ttgatagtag tctacttagt ttcaagtttt gggtttgtgt atactttcac    960

taataatatg cgtggaaaca ttgcaggtga tgagcgaaat gtagtgctta cgttgtcccg   1020

catttggtac agcgcagtaa ccggcaaaat cgcgccgaag gatgtcgctg ccgactgggc   1080

aatggagcgc ctgccggccc agtatcagcc cgtcatactt gaagctagac aggcttatct   1140

tggacaagaa gaagatcgct tggcctcgcg cgcagatcag ttggaagaat ttgtccacta   1200

cgtgaaaggc gagatcacca aggtagtcgg caaataa                            1237
```

<210> SEQ ID NO 22
<211> LENGTH: 31
<212> TYPE: DNA
<213> ORGANISM: Artificial Sequence
<220> FEATURE:
<223> OTHER INFORMATION: Synthetic sequence: Primer AS749

<400> SEQUENCE: 22

```
ggatatcaaa caaatacaaa atcaaaatag a                                    31
```

<210> SEQ ID NO 23
<211> LENGTH: 29
<212> TYPE: DNA
<213> ORGANISM: Artificial Sequence
<220> FEATURE:
<223> OTHER INFORMATION: Synthetic sequence: Primer AS778

<400> SEQUENCE: 23

```
ggaattctga gcgcgctaga gcgatcctg                                       29
```

<210> SEQ ID NO 24
<211> LENGTH: 248
<212> TYPE: DNA
<213> ORGANISM: Nicotiana tabacum

<400> SEQUENCE: 24

```
gaattctgag cgcgctagag cgatcctggc ctagtctata ggaggttttg aaaagaaagg     60

agcaataatc attttcttgt tctatcaaga gggtgctatt gctcctttct ttttttcttt    120

ttatttattt actagtattt tacttacata gactttttttg tttacattat agaaaaagaa    180

ggagaggtta ttttcttgca tttattcatg attgagtatt ctattttgat tttgtatttg    240

tttgatat                                                             248
```

<210> SEQ ID NO 25
<211> LENGTH: 35
<212> TYPE: DNA
<213> ORGANISM: Artificial sequence
<220> FEATURE:
<223> OTHER INFORMATION: Synthetic sequence: Primer AS830

<400> SEQUENCE: 25

```
ccgcggtatc tcacattcac ccaattgtca tggtt                                35
```

<210> SEQ ID NO 26
<211> LENGTH: 40

<212> TYPE: DNA
<213> ORGANISM: Artificial Sequence
<220> FEATURE:
<223> OTHER INFORMATION: Synthetic sequence: Primer AS831

<400> SEQUENCE: 26
ttagaagtat cctgtgcaca tccgcaacca tgacaattgg 40

<210> SEQ ID NO 27
<211> LENGTH: 45
<212> TYPE: DNA
<213> ORGANISM: Artificial Sequence
<220> FEATURE:
<223> OTHER INFORMATION: Synthetic sequence: Primer AS832

<400> SEQUENCE: 27
acaggatact tctaaggaag tccacacaaa tcaagaaccc ttaga 45

<210> SEQ ID NO 28
<211> LENGTH: 45
<212> TYPE: DNA
<213> ORGANISM: Artificial Sequence
<220> FEATURE:
<223> OTHER INFORMATION: Synthetic sequence: Primer AS833

<400> SEQUENCE: 28
tcacattctt ctgttttggt agctgaaacg tctaagggtt cttga 45

<210> SEQ ID NO 29
<211> LENGTH: 45
<212> TYPE: DNA
<213> ORGANISM: Artificial Sequence
<220> FEATURE:
<223> OTHER INFORMATION: Synthetic sequence: Primer AS834

<400> SEQUENCE: 29
acagaagaat gtgagaaggc ttccactaag gctaactctc aacag 45

<210> SEQ ID NO 30
<211> LENGTH: 29
<212> TYPE: DNA
<213> ORGANISM: Artificial Sequence
<220> FEATURE:
<223> OTHER INFORMATION: Synthetic sequence: Primer AS835

<400> SEQUENCE: 30
cgcggccgcg ttgtctgttg agagttagc 29

<210> SEQ ID NO 31
<211> LENGTH: 164
<212> TYPE: DNA
<213> ORGANISM: Artificial Sequence
<220> FEATURE:
<223> OTHER INFORMATION: Synthetic sequence: Primer Binding Domain

<400> SEQUENCE: 31
ccgcggtatc tcacattcac ccaattgtca tggttgcgga tgtgcacagg atacttctaa 60
ggaagtccac acaaatcaag aacccttaga cgtttcagct accaaaacag aagaatgtga 120
gaaggcttcc actaaggcta actctcaaca gacaacgcgg ccgc 164

<210> SEQ ID NO 32
<211> LENGTH: 2327
<212> TYPE: DNA
<213> ORGANISM: Artificial Sequence
<220> FEATURE:

-continued

<223> OTHER INFORMATION: Synthetic sequence: LtrASi gene sequence

<400> SEQUENCE: 32

```
gcatgcatga agccaacaat ggcaatcctc gaacgaatct ctaagaactc acaggagaac     60
atcgacgagg tacaataacc catatatatg aattgattca tgtgttactc gtacttgttt    120
gaatatgttt ggagcaagtt tgatactttt ggatgatgat atcgcaaatt cgttatcttt    180
ttggcgttat aggtcttcac aagactttac cgttaccttc tccgtcctga catctactac    240
gtggcatatc agaacctcta ctctaacaag ggagcttcta caaagggaat cctcgatgat    300
acagctgatg gattctctga ggagaagatc aagaagatca tccaatcttt gaaggacgga    360
acttactacc ctcagcctgt ccgaagaatg tacatcgcaa agaagaactc taagaagatg    420
agacctcttg gaatcccaac tttcacagac aagttgatcc aggaggctgt gagaatcatc    480
cttgaatcta tctatgagcc tgtcttcgag gatgtgtctc acggtttccg acctcagcga    540
agctgtcaca cagctttgaa gacaatcaag agagagttcg gaggtaaatt atatgctttg    600
ccacttcctc aaaagatcat tttaggttca ttggtatgtg gtttttttct taacaggtgc    660
aagatggttc gtggagggag atatcaaggg atgcttcgat aacatcgacc acgtcacact    720
catcggactc atcaacctta agatcaagga tatgaagatg agccagttga tctacaagtt    780
cctcaaggca ggttacctcg aaaactggca gtaccacaag acttacagcg gaacacctca    840
gggcggaatc ctctctcctc tcctcgctaa catctatctt catgaattgg acaagttcgt    900
tctccaactc aagatgaagt tcgaccgaga gagtccagag agaatcacac ctgaataccg    960
ggagcttcac aacgagatca aaagaatctc tcaccgtctc aagaagttgg agggcgagga   1020
gaaggctaag gttctcttgg aataccagga gaagaggaag aggttgccta cactcccttg   1080
tacatcacaa acaaacaagg ttcgttctct ccattttcat tcgtttgagt ctgatttagt   1140
gttttgtggt tgatctgaat cgatttattg ttgattagtg aatcaatttg aggctgtgtc   1200
ctaatgtttt gacttttgat tacaggtctt gaagtacgtc cgatacgctg acgacttcat   1260
catctctgtt aagggaagca aggaggactg tcaatggatc aaggagcaat tgaagctctt   1320
catccataac aagctcaaga tggaattgag tgaggagaag acactcatca cacatagcag   1380
tcagcctgct cgtttcctcg gatacgacat ccgagtcagg agaagtggaa ctatcaagcg   1440
atctggaaag gttcaattct ttctttcaca tttgtacttg ttcactcgtt ttattaatcc   1500
tctttagaat ggagattctt acctctgtgt ggcctttggc aggtcaagaa gagaacactc   1560
aacgggagtg tggagcttct catccctctc caagacaaga tccgtcaatt catcttcgac   1620
aagaagatcg ctatccagaa gaaggatagc tcatggttcc cagttcacag gaagtacctt   1680
atccgttcaa cagacttgga gatcatcaca atctacaact ctgaattgag aggtaagctg   1740
ctacctcaaa ctttctagtg cttccatatt tcctttcttc tgcaaggcag agaaccattg   1800
tggttaagtg ttttaaattg tgaatgtata ggtatctgca actactacgg tctcgcaagt   1860
aacttcaacc agctcaacta cttcgcttac cttatggaat actcttgctt gaagactatc   1920
gcatctaagc ataagggaac actctcaaag accatctcta tgttcaagga tggaagtggt   1980
tcttggggaa tcccttacga gatcaagcag gggaagcaga ggagatactt cgccaacttc   2040
agtgaatgca aatctcctta ccaattcact gatgagatca gtcaagctcc tgtgctttac   2100
ggatacgctc ggaacactct tgagaacaga cttaaggcta agtgttgtga gctttgtgga   2160
acatctgatg agaacacatc ttacgagatc caccacgtca acaaggtcaa gaaccttaag   2220
ggaaaggaga agtgggagat ggcaatgatc gctaagcagc ggaagactct tgttgtttgc   2280
```

ttccattgtc atcgtcacgt gatccataag cacaagtgaa ctagtaa 2327

<210> SEQ ID NO 33
<211> LENGTH: 34
<212> TYPE: DNA
<213> ORGANISM: Artificial Sequence
<220> FEATURE:
<223> OTHER INFORMATION: Synthetic sequence: Primer AS794

<400> SEQUENCE: 33
gctcgagaca atggcttcct cagttctttc ctct 34

<210> SEQ ID NO 34
<211> LENGTH: 36
<212> TYPE: DNA
<213> ORGANISM: Artificial Sequence
<220> FEATURE:
<223> OTHER INFORMATION: Synthetic sequence: Primer AS639

<400> SEQUENCE: 34
cgcatgctac ctgcatacat tgcactcttc caccat 36

<210> SEQ ID NO 35
<211> LENGTH: 28
<212> TYPE: DNA
<213> ORGANISM: Artificial Sequence
<220> FEATURE:
<223> OTHER INFORMATION: Synthetic sequence: Primer AS724

<400> SEQUENCE: 35
cggtacctac cggatttgga gccaagtc 28

<210> SEQ ID NO 36
<211> LENGTH: 36
<212> TYPE: DNA
<213> ORGANISM: Artificial Sequence
<220> FEATURE:
<223> OTHER INFORMATION: Synthetic sequence: Primer AS726

<400> SEQUENCE: 36
gtgtttggtg acctgaaata aaacaataga acaagt 36

<210> SEQ ID NO 37
<211> LENGTH: 1738
<212> TYPE: DNA
<213> ORGANISM: Arabidopsis thaliana

<400> SEQUENCE: 37
taccggattt ggagccaagt ctcataaacg ccattgtgga agaaagtctt gagttggtgg 60
taatgtaaca gagtagtaag aacagagaag agagagagtg tgagatacat gaattgtcgg 120
gcaacaaaaa tcctgaacat cttattttag caaagagaaa gagttccgag tctgtagcag 180
aagagtgagg agaaatttaa gctcttggac ttgtgaattg ttccgcctct tgaatacttc 240
ttcaatcctc atatattctt cttctatgtt acctgaaaac cggcatttaa tctcgcgggt 300
ttattccggt tcaacatttt ttttgttttg agttattatc tgggcttaat aacgcaggcc 360
tgaaataaat tcaaggccca actgtttttt tttttaagaa gttgctgtta aaaaaaaaaa 420
aagggaatta acaacaacaa caaaaaaaga taaagaaaat aataacaatt actttaattg 480
tagactaaaa aaacatagat tttatcatga aaaaaagaga aaagaaataa aaacttggat 540
caaaaaaaaa acatacagat cttctaatta ttaacttttc ttaaaaatta ggtccttttt 600

```
cccaacaatt aggtttagag ttttggaatt aaaccaaaaa gattgttcta aaaaatactc    660

aaatttggta gataagtttc cttattttaa ttagtcaatg gtagatactt tttttctttt    720

tctttattag agtagattag aatcttttat gccaagtatt gataaattaa atcaagaaga    780

taaactatca taatcaacat gaaattaaaa gaaaaatctc atatatagta ttagtattct    840

ctatatatat tatgattgct tattcttaat gggttgggtt aaccaagaca tagtcttaat    900

ggaaagaatc tttttgaac tttttcctta ttgattaaat tcttctatag aaaagaaaga    960

aattatttga ggaaaagtat atacaaaaag aaaaatagaa aaatgtcagt gaagcagatg   1020

taatggatga cctaatccaa ccaccaccat aggatgtttc tacttgagtc ggtcttttaa   1080

aaacgcacgg tggaaaatat gacacgtatc atatgattcc ttcctttagt ttcgtgataa   1140

taatcctcaa ctgatatctt cctttttttg ttttggctaa agatatttta ttctcattaa   1200

tagaaaagac ggttttgggc ttttggtttg cgatataaag aagaccttcg tgtggaagat   1260

aataattcat cctttcgtct ttttctgact cttcaatctc tcccaaagcc taaagcgatc   1320

tctgcaaatc tctcgcgact ctctctttca aggtatattt tctgattctt tttgtttttg   1380

attcgtatct gatctccaat ttttgttatg tggattattg aatcttttgt ataaattgct   1440

tttgacaata ttgttcgttt cgtcaatcca gcttctaaat tttgtcctga ttactaagat   1500

atcgattcgt agtgtttaca tctgtgtaat ttcttgcttg attgtgaaat taggattttc   1560

aaggacgatc tattcaattt ttgtgttttc tttgttcgat tctctctgtt ttaggtttct   1620

tatgtttaga tccgtttctc tttggtgttg ttttgatttc tcttacggct tttgatttgg   1680

tatatgttcg ctgattggtt tctacttgtt ctattgtttt atttcaggtc accaaaca     1738
```

<210> SEQ ID NO 38
<211> LENGTH: 276
<212> TYPE: DNA
<213> ORGANISM: Artificial Sequence
<220> FEATURE:
<223> OTHER INFORMATION: Synthetic sequence: nos terminator sequence
      based on gene bank sequence accession EU048864

<400> SEQUENCE: 38

```
tctagagtca agcagatcgt tcaaacattt ggcaataaag tttcttaaga ttgaatcctg     60

ttgccggtct tgcgatgatt atcatataat ttctgttgaa ttacgtgaag catgtaataa    120

ttaacatgta atgcatgacg ttatttatga gatgggtttt tatgattaga gtcccgcaat    180

tatacattta atacgcgata gaaaacaaaa tatagcgcgc aaactaggat aaattatcgc    240

gcgcggtgtc atctatgtta ctagatcgac ctgcag                               276
```

<210> SEQ ID NO 39
<211> LENGTH: 2465
<212> TYPE: DNA
<213> ORGANISM: Artificial Sequence
<220> FEATURE:
<223> OTHER INFORMATION: Synthetic sequence: RTRHi-Ty1 sequence

<400> SEQUENCE: 39

```
atgaacaatt catcccacaa catcgttcct atcaagactc caactactgt ttctgagcag     60

aacactgaag aatctatcat cgctgatctt ccacttcctg atcttcctcc agaatctcct    120

actgaatttc ctgatccatt caaagaactt ccacctatca actcaagaca aactaactct    180

tcattgggcg gaattggcga ttctaatgct tacactacta tcaactctaa gaagaggtat    240

tgtagccagc ctcaaccagt ctttttgctg ttacattttc ttgggctcat ctaatgttat    300
```

-continued

```
tttcctattt tgttttcagg tcacttgaag ataatgaaac tgaaatcaaa gtttctaggg    360
atacatggaa tactaagaat atgagatcac ttgaacctcc aagatctaag aagagaatcc    420
atcttattgc agctgttaaa gctgtgaaat caatcaaacc aattagaaca actcttagat    480
acgatgaagc aattacatac aacaaagaca tcaaggagaa ggagaaatac atcgaggctt    540
accacaaaga agttaaccaa cttcttaaga tgaaaacttg ggatactgat gaatactacg    600
atagaaaaga gattgaccct aagagagtta tcaactcaat gttcatcttc aacaagaaga    660
gagacggaac tcacaaagct agattcgttg caagaggaga tattcagcat cctgacactt    720
acgattcagg taagtattcc aatgttcttc gattatgagt caatgttgtt actgtatctg    780
tctctgtggt ttattgtttc aggcttagtt attgattagt attgaaactt cactcacata    840
tttttttgtt tgttttctga attgtgcagg tatgcaatct aatactgttc atcactacgc    900
attgatgaca tctctttcac ttgcattgga caataactac tacattacac aacttgacat    960
atcttctgca tacctttacg ctgatatcaa ggaggagctt tacattagac ctccaccaca   1020
tttgggaatg aatgataagt tgatccgttt gaagaaatca ctttacggat tgaaacaatc   1080
tggagctaat tggtacgaaa ctatcaaatc ataccttatt cagcaatgcg gtatggagga   1140
agttagggga tggtcatgcg tattcaagaa ctctcaagtt acaatctgcc tcttcgttga   1200
tgatatggtg ctcttctcta agaatcttaa ctcaaacaag agaatcattg agaagttgaa   1260
gatgcaatac gacactaaga tcatcaacct tggagaatct gatgaggaaa ttcaatacga   1320
cattcttgga ttggaaatca aataccaaag aggtgagtta tatttaacag ctcatcagtt   1380
acttaaacac tttttgggac aagcagttca aactcatgtt ccaatcctaa aattaattgc   1440
aattcacagg taagtacatg aagttgggaa tggaaaactc attgactgag aagattccta   1500
aacttaacgt tcctttgaat ccaaagggaa gaaagctctc tgctccagga caaccaggac   1560
tttacattga ccaggatgaa cttgagattg atgaggatga atacaaggag aaagtacacg   1620
agatgcagaa gttgattgga cttgcttcat acgttggata caaattcaga ttcgaccttc   1680
tttactacat caacacactt gctcagcata tacttttccc atctaggcaa gttcttgaca   1740
tgacatacga gcttatccaa ttcatgtggg acactagaga caagcaactc atatggcaca   1800
agaacaagcc tacagagcca gataacaagc tcgttgcaat ctctgatgct tcttacggaa   1860
accaaccata ctacaaatca caaattggaa acatctactt gcttaacgga aaggtacttt   1920
tctcaaagac tttaccttat tgtggaatat tgaattttct gaaagacttc accttatcta   1980
catttgtaat tttactatgg taatcaggtg attggaggaa agagcactaa ggcttcactt   2040
acatgcactt caactactga ggcagagatc cacgctatat cagaatctgt accacttctt   2100
aacaaccttt cttaccttat ccaagagctt aacaagaagc caatcatcaa gggacttctt   2160
actgactcaa gatcaacaat ctctatcatt aagtctacaa atgaagagaa attcagaaac   2220
agattcttcg gaacaaaggc aatgagactt agagatgaag tttcaggtaa gtattaactt   2280
accaaatgat caatattatt ttgaaatgca ggttttagaa taatactctc tgccgttctt   2340
gtttatttcc aggtaacaac ctttacgttt actacatcga gactaagaag aacattgctg   2400
acgttatgac aaagcctctt cctatcaaga ccttcaagtt gcttactaac aaatggattc   2460
attaa                                                                2465
```

<210> SEQ ID NO 40
<211> LENGTH: 31
<212> TYPE: DNA
<213> ORGANISM: Artificial Sequence
<220> FEATURE:
<223> OTHER INFORMATION: Synthetic sequence: Primer AS293

<400> SEQUENCE: 40
tctcgagttg atggcttctt ctgctcaaat a 31

<210> SEQ ID NO 41
<211> LENGTH: 29
<212> TYPE: DNA
<213> ORGANISM: Artificial Sequence
<220> FEATURE:
<223> OTHER INFORMATION: Synthetic sequence: Primer AS294

<400> SEQUENCE: 41
ggcatgcaac tctcaaagtg aaacccttc 29

<210> SEQ ID NO 42
<211> LENGTH: 207
<212> TYPE: DNA
<213> ORGANISM: Pisum sativum

<400> SEQUENCE: 42
ctcgagatgg cttcttctgc tcaaatacac ggtctcggaa ccgcttcttt ctcttccctc 60
aaaaaaccct cttccatttc cggtaattcc aaaacccttt tcttcggtca gcgactcaat 120
tccaaccact ctcccttcac ccgcgccgca ttccctaagt taagtagcaa aacctttaag 180
aagggtttca ctttgagagt tgcatgc 207

<210> SEQ ID NO 43
<211> LENGTH: 28
<212> TYPE: DNA
<213> ORGANISM: Artificial Sequence
<220> FEATURE:
<223> OTHER INFORMATION: Synthetic sequence: Primer AG3

<400> SEQUENCE: 43
ggtaccatga tcgcttcatg tttttatc 28

<210> SEQ ID NO 44
<211> LENGTH: 30
<212> TYPE: DNA
<213> ORGANISM: Artificial Sequence
<220> FEATURE:
<223> OTHER INFORMATION: Synthetic sequence: Primer AG4

<400> SEQUENCE: 44
ctcgaggttc cttttttgcc gatatgttag 30

<210> SEQ ID NO 45
<211> LENGTH: 1101
<212> TYPE: DNA
<213> ORGANISM: Arabidopsis thaliana

<400> SEQUENCE: 45
gtaccatgat cgcttcatgt ttttatctaa tttgttagca tattgaatga ttgattttct 60
tttaatttgg atatgttgat tgtcttgttg catcatcaat gtatgtttta tttaacaccg 120
gaagatctta tgatgggttc attacttcat aataatctcc gagttctaca agactacaac 180
tttcacgtga cttttacagc gacaaaaaat gcatctagcg aaaattaatc cacaacctat 240
gcatttttgt cactcttcac acgcgtatgt gcataaatat atagtatata ctcgacaatc 300
gatgcgtatg tgtacacaat taccaaaaca attatttgaa tattcagaca tgggttgaca 360

-continued tcaccaagta atattcacag tatctgaaaa ctatgttttg acatccctaa atagtttgac 420
taaccagttt aatatgagag catttgtaag aggcaagagc catggttttg ttggctcgtt 480
taatatgctc atttaacccc cccaaaaaat actattagat ttaaacgtaa aagaattaac 540
gaacacaaga actgctaaaa caaaaaaaaa tcaatggccg acatttcata gttcatacat 600
cactaatact aaaagatgca tcatttcact agggtctcat gaaataggag ttgacatttt 660
tttttgtaac gacagaagtt gacatgttaa gcatcaattt ttttaagagt ggattatact 720
agtttttttt ttttttttta atgtatggta tgatacaaca acaaaaacta taaaatagaa 780
aaagtcagtg aaacctcaaa ttgaaggaaa aacttttgca caaaaagaga gagagagaga 840
aagaatgtaa atccaaataa atgggcctaa ttgagaatgc tttaactttt tttttttggc 900
taaaagagaa tgctttaact aagcccataa aatgaacatc aaactcaaag ggtaagatta 960
atacatttag aaaacaatag ccgaatattt aataagttta agacatagag gagttttatg 1020
taatttagga accgatccat cgttggctgt ataaaaaggt tacatctccg gctaacatat 1080
cggcaaaaaa ggaacctcga g 1101

<210> SEQ ID NO 46
<211> LENGTH: 406
<212> TYPE: DNA
<213> ORGANISM: Artificial Sequence
<220> FEATURE:
<223> OTHER INFORMATION: Synthetic sequence: ags terminator sequence

<400> SEQUENCE: 46
gaattaacag aggtggatgg acagacccgt tcttacaccg gactgggcgc gggataggat 60
attcagattg ggatgggatt gagcttaaag ccggcgctga gaccatgctc aaggtaggca 120
atgtcctcag cgtcgagccc ggcatctatg tcgagggcat tggtggagcg cgcttcgggg 180
ataccgtgct tgtaactgag accggatatg aggccctcac tccgcttgat cttggcaaag 240
atatttgacg catttattag tatgtgttaa ttttcatttg cagtgcagta ttttctattc 300
gatctttatg taattcgtta caattaataa atattcaaat cagattattg actgtcattt 360
gtatcaaatc gtgtttaatg gatattttta ttataatatt gatgat 406

<210> SEQ ID NO 47
<211> LENGTH: 22
<212> TYPE: DNA
<213> ORGANISM: Artificial Sequence
<220> FEATURE:
<223> OTHER INFORMATION: Synthetic sequence: Primer LFS1

<400> SEQUENCE: 47
gagatgtgga tcatccaagg ca 22

<210> SEQ ID NO 48
<211> LENGTH: 22
<212> TYPE: DNA
<213> ORGANISM: Artificial Sequence
<220> FEATURE:
<223> OTHER INFORMATION: Synthetic sequence: Primer RFS1

<400> SEQUENCE: 48
ctaccataga ggccaacgat ag 22

<210> SEQ ID NO 49
<211> LENGTH: 18
<212> TYPE: DNA
<213> ORGANISM: Artificial Sequence
<220> FEATURE:
<223> OTHER INFORMATION: Synthetic sequence: Primer AS257

<400> SEQUENCE: 49
aacgtcggtt cgagatgg 18

<210> SEQ ID NO 50
<211> LENGTH: 21
<212> TYPE: DNA
<213> ORGANISM: Artificial Sequence
<220> FEATURE:
<223> OTHER INFORMATION: Synthetic sequence: Primer aadA-F1

<400> SEQUENCE: 50
cgaaggatgt cgctgccgac t 21

<210> SEQ ID NO 51
<211> LENGTH: 22
<212> TYPE: DNA
<213> ORGANISM: Artificial Sequence
<220> FEATURE:
<223> OTHER INFORMATION: Synthetic sequence: Primer LFS2

<400> SEQUENCE: 51
ctcctcctca ggaggataga tg 22

<210> SEQ ID NO 52
<211> LENGTH: 23
<212> TYPE: DNA
<213> ORGANISM: Artificial Sequence
<220> FEATURE:
<223> OTHER INFORMATION: Synthetic sequence: Primer RFS2

<400> SEQUENCE: 52
aactttcatc gtactgtgct ctc 23

<210> SEQ ID NO 53
<211> LENGTH: 20
<212> TYPE: DNA
<213> ORGANISM: Artificial Sequence
<220> FEATURE:
<223> OTHER INFORMATION: Synthetic sequence: Primer AS526

<400> SEQUENCE: 53
gagtcgatac ttcggcgatc 20

<210> SEQ ID NO 54
<211> LENGTH: 22
<212> TYPE: DNA
<213> ORGANISM: Artificial Sequence
<220> FEATURE:
<223> OTHER INFORMATION: Synthetic sequence: Primer aadA-F2

<400> SEQUENCE: 54
ctagacaggc ttatcttgga ca 22

<210> SEQ ID NO 55
<211> LENGTH: 22
<212> TYPE: DNA
<213> ORGANISM: Artificial Sequence
<220> FEATURE:
<223> OTHER INFORMATION: Synthetic sequence: Primer LP-F

<400> SEQUENCE: 55
cgtgtttagt tgccatcgtt ga 22

<210> SEQ ID NO 56
<211> LENGTH: 21
<212> TYPE: DNA
<213> ORGANISM: Artificial Sequence
<220> FEATURE:
<223> OTHER INFORMATION: Synthetic sequence: Primer LP-R

<400> SEQUENCE: 56
gctgagagcc ctcacagccc a 21

<210> SEQ ID NO 57
<211> LENGTH: 23
<212> TYPE: DNA
<213> ORGANISM: Artificial Sequence
<220> FEATURE:
<223> OTHER INFORMATION: Synthetic sequence: Primer RP-F

<400> SEQUENCE: 57
tgtcagcggt tcgagtccgc tta 23

<210> SEQ ID NO 58
<211> LENGTH: 23
<212> TYPE: DNA
<213> ORGANISM: Artificial Sequence
<220> FEATURE:
<223> OTHER INFORMATION: Synthetic sequence: Primer RP-R

<400> SEQUENCE: 58
taaccaagcc actgcctatg agt 23

<210> SEQ ID NO 59
<211> LENGTH: 21
<212> TYPE: DNA
<213> ORGANISM: Artificial Sequence
<220> FEATURE:
<223> OTHER INFORMATION: Synthetic sequence: Primer aadA1

<400> SEQUENCE: 59
gtgatcgccg aagtatcgac t 21

<210> SEQ ID NO 60
<211> LENGTH: 21
<212> TYPE: DNA
<213> ORGANISM: Artificial Sequence
<220> FEATURE:
<223> OTHER INFORMATION: Synthetic sequence: Primer aadA2

<400> SEQUENCE: 60
atctcgcctt tcacgtagtg g 21

<210> SEQ ID NO 61
<211> LENGTH: 27
<212> TYPE: DNA
<213> ORGANISM: Artificial Sequence
<220> FEATURE:
<223> OTHER INFORMATION: Synthetic sequence: Primer AS912

<400> SEQUENCE: 61
gccgcggctt tattaccgtg aatatta 27

<210> SEQ ID NO 62
<211> LENGTH: 30
<212> TYPE: DNA
<213> ORGANISM: Artificial Sequence
<220> FEATURE:
<223> OTHER INFORMATION: Synthetic sequence: Primer AS913

<400> SEQUENCE: 62
cgcggccgct ctgataagtg caacctgatt 30

<210> SEQ ID NO 63
<211> LENGTH: 333
<212> TYPE: DNA
<213> ORGANISM: Nicotiana tabacum

<400> SEQUENCE: 63
ctttattacc gtgaatatta ttttggtaag gggtttattc ccaacaactg gtatcagagc 60
acaggttctg ctcgttcact gaaatactat tcactgtcgg tagtactata cttggtgaaa 120
aataaaaatg tctggagtaa agtacgaggt agcaaaattc aatggagata acggtttctc 180
aacatggcaa agaaggatga gagatctgct catccaacaa ggattacaca aggttctaga 240
tgttgattcc aaaaagcctg ataccatgaa agctgaggat tgggctgact tggatgaaag 300
agctgctagt gcaatcaggt tgcacttatc aga 333

<210> SEQ ID NO 64
<211> LENGTH: 27
<212> TYPE: DNA
<213> ORGANISM: Artificial Sequence
<220> FEATURE:
<223> OTHER INFORMATION: Synthetic sequence: Primer AS699

<400> SEQUENCE: 64
ggcgcgccgt gggatccggg cggtccg 27

<210> SEQ ID NO 65
<211> LENGTH: 26
<212> TYPE: DNA
<213> ORGANISM: Artificial Sequence
<220> FEATURE:
<223> OTHER INFORMATION: Synthetic sequence: Primer AS700

<400> SEQUENCE: 65
ggcatgctgg cgcagctggg ccatcc 26

<210> SEQ ID NO 66
<211> LENGTH: 771
<212> TYPE: DNA
<213> ORGANISM: Oryza sativa

<400> SEQUENCE: 66
gggatccggg cggtccgggg ggggcactac ggctcctctc ttctcgagaa tccatacatc 60
ccttatcagt gtatggagag ctatctctcg agcacaggtt gaggttcgtc ctcaatggga 120
aaatggagca cctaacaacg catcttcaca gaccaagaac tacgagatca ccctttcatt 180
ctggggtgac ggagggatcg taccattcga gccttttttt catgcttttc ccggcggtct 240
ggagaaagca gcaatcaata ggacttccct aatcctccct tcctgaaagg aagaacgtga 300
aattcttttt cctttccgca gggaccagga ggttggatct agccataaga ggaatgcttg 360
gtataaataa gccacttctt ggtcttcgac tccctaagtc actacgagcg ccctcgatca 420
gtgcaatggg atgtggctat ttatctatct cttgactcga aatgggagca gagcaggttt 480
gaaaaaggat cttagagtgt ctagggttgg gccaggaggg tctcttaacg ccttcctttt 540
tctgcccatc ggagttattt cccaaggact tgccatggta agggggagaa ggggaagaag 600
cacacttgaa gagcgcagta caacggagag ttgtatgctg cgttcgggaa ggatgaatcg 660
ctcccgaaaa ggagtctatt gattctctcc caattggttg gatcgtaggg gcgatgattt 720
acttcacggg cgaggtctct ggttcaagtc caggatggcc cagctgcgcc a 771

<210> SEQ ID NO 67
<211> LENGTH: 25
<212> TYPE: DNA
<213> ORGANISM: Artificial Sequence
<220> FEATURE:
<223> OTHER INFORMATION: Synthetic sequence: Primer AS701

<400> SEQUENCE: 67
gatatcggat ggcccagctg cgcca 25

<210> SEQ ID NO 68
<211> LENGTH: 27
<212> TYPE: DNA
<213> ORGANISM: Artificial Sequence
<220> FEATURE:
<223> OTHER INFORMATION: Synthetic sequence: Primer AS702

<400> SEQUENCE: 68
gcggccgcat tgcccttctc cgaccct 27

<210> SEQ ID NO 69
<211> LENGTH: 631
<212> TYPE: DNA
<213> ORGANISM: Oryza sativa

<400> SEQUENCE: 69
ggatggccca gctgcgccag ggaaaagaat agaagaagca tctgactctt tcatgcatac 60
tccacttggc tcggggggat atagctcagt tggtagagct ccgctcttgc aattgggtcg 120
ttgcgattac gggttggctg tctaattgtc caggcggtaa tggtagtatc ttgtacctga 180
accggtggct cactttttct aagtaatggg gaagaggact gaaacatgcc actgaaagac 240
tctactgaga caaaaagatg ggctgtcaaa aaggtagagg aggtaggatg ggcagttggt 300
cagatctagt atggatcgta catggacgat agttggagtc ggcggctctc ctaggcttcc 360
ctcatctggg atccctgggg aagaggatca agttggccct tgcgaatagc ttgatgcact 420
atctcccttc aaccctttga gcgaaatgtg gcaaaaggaa ggaaaatcca tggaccgacc 480
ccattatctc caccccgtag gaactacgag atcaccccaa ggacgccttc ggcgtccagg 540
ggtcacggac cgaccataga ccctgttcaa taagtggaac acattagccg tccgctctcc 600
ggttgggcag taagggtcgg agaagggcaa t 631

<210> SEQ ID NO 70
<211> LENGTH: 30
<212> TYPE: DNA
<213> ORGANISM: Artificial Sequence
<220> FEATURE:
<223> OTHER INFORMATION: Synthetic sequence: Primer AS518

<400> SEQUENCE: 70
tatcgataac attcctctaa tttcattgca 30

<210> SEQ ID NO 71
<211> LENGTH: 31
<212> TYPE: DNA
<213> ORGANISM: Artificial Sequence
<220> FEATURE:
<223> OTHER INFORMATION: Synthetic sequence: Primer AS720

<400> SEQUENCE: 71

```
ggcatgcagg cttgtgggat tgacgtgata g                               31


<210> SEQ ID NO 72
<211> LENGTH: 172
<212> TYPE: DNA
<213> ORGANISM: Triticum aestivum

<400> SEQUENCE: 72

aggcttgtgg gattgacgtg atagggtagg gttggctata ctgctggtgg cgaactccag     60

gctaataatc tgaagcgcat ggatacaagt tatccttgga aggaaagaca attccgaatc    120

tgctttgtct acgaataagg aagctataag taatgcaact atgaatctca tg            172


<210> SEQ ID NO 73
<211> LENGTH: 1521
<212> TYPE: DNA
<213> ORGANISM: Artificial Sequence
<220> FEATURE:
<223> OTHER INFORMATION: Synthetic sequence: aadA-mGFP4 fusion sequence

<400> SEQUENCE: 73

atggcagaag cggtgatcgc cgaagtatcg actcaactat cagaggtagt tggcgtcatc     60

gagcgccatc tcgaaccgac gttgctggcc gtacatttgt acggctccgc agtggatggc    120

ggcctgaagc cacacagtga tattgatttg ctggttacgg tgaccgtaag gcttgatgaa    180

acaacgcggc gagctttgat caacgacctt ttggaaactt cggcttcccc tggagagagc    240

gagattctcc gcgctgtaga agtcaccatt gttgtgcacg acgacatcat tccgtggcgt    300

tatccagcta agcgcgaact gcaatttgga gaatggcagc gcaatgacat tcttgcaggt    360

atcttcgagc cagccacgat cgacattgat ctggctatct tgctgacaaa agcaagagaa    420

catagcgttg ccttggtagg tccagcggcg gaggaactct ttgatccggt tcctgaacag    480

gatctatttg aggcgctaaa tgaaacctta acgctatgga actcgccgcc cgactgggct    540

ggcgatgagc gaaatgtagt gcttacgttg tcccgcattt ggtacagcgc agtaaccggc    600

aaaatcgcgc cgaaggatgt cgctgccgac tgggcaatgg agcgcctgcc ggcccagtat    660

cagcccgtca tacttgaagc tagacaggct tatcttggac aagaagaaga tcgcttggcc    720

tcgcgcgcag atcagttgga agaatttgtc cactacgtga aaggcgagat caccaaggta    780

gtcggcaaat caggatccat gagtaaagga gaagaacttt tcactggagt tgtcccaatt    840

cttgttgaat tagatggtga tgttaatggg cacaaatttt ctgtcagtgg agagggtgaa    900

ggtgatgcaa catacggaaa acttaccctt aaatttattt gcactactgg aaaactacct    960

gttccatggc caacacttgt cactactttc tcttatggtg ttcaatgctt ttcaagatac   1020

ccagatcata tgaagcggca cgacttcttc aagagcgcca tgcctgaggg atacgtgcag   1080

gagaggacca tcttcttcaa ggacgacggg aactacaaga cacgtgctga agtcaagttt   1140

gagggagaca ccctcgtcaa caggatcgag cttaagggaa tcgatttcaa ggaggacgga   1200

aacatcctcg gccacaagtt ggaatacaac tacaactccc acaacgtata catcatggca   1260

gacaaacaaa agaatggaat caaagttaac ttcaaaatta gacacaacat tgaagatgga   1320

agcgttcaac tagcagacca ttatcaacaa aatactccaa ttggcgatgg ccctgtcctt   1380

ttaccagaca accattacct gtccacacaa tctgcccttt cgaaagatcc caacgaaaag   1440

agagaccaca tggtccttct tgagtttgta acagctgctg ggattacaca tggcatggat   1500

gaactataca aataatctag a                                             1521
```

<210> SEQ ID NO 74
<211> LENGTH: 29
<212> TYPE: DNA
<213> ORGANISM: Artificial Sequence
<220> FEATURE:
<223> OTHER INFORMATION: Synthetic sequence: Primer AS753

<400> SEQUENCE: 74
accgcggtca aataaatttt gcatgtcta 29

<210> SEQ ID NO 75
<211> LENGTH: 28
<212> TYPE: DNA
<213> ORGANISM: Artificial Sequence
<220> FEATURE:
<223> OTHER INFORMATION: Synthetic sequence: Primer AS723

<400> SEQUENCE: 75
gatatctcca tactccttct ttatgata 28

<210> SEQ ID NO 76
<211> LENGTH: 360
<212> TYPE: DNA
<213> ORGANISM: Triticum aestivum

<400> SEQUENCE: 76
caaataaatt ttgcatgtct actcttgtta gtagaatagg aatcgttgag aaagattttt 60
catttgaatc atgcaaaaaa gttttctttg tttttagttt agtatagtta tttaaagaat 120
agatagaaat aagattgcgt ccaataggat ttgaacctat accaaaggtt tagaagacct 180
ctgtcctatc cattagacaa tggacgcttt tctttcatat tttattcttt cttttatttt 240
tttttcttct tccgagaaaa aactgttaga ccaaaactct tttaggaaat caaaaaatcc 300
agatacaaat gcatgatgta tatattatat catgcatata tcataaagaa ggagtatgga 360

<210> SEQ ID NO 77
<211> LENGTH: 22
<212> TYPE: DNA
<213> ORGANISM: Artificial Sequence
<220> FEATURE:
<223> OTHER INFORMATION: Synthetic sequence: Primer ARP1

<400> SEQUENCE: 77
gtcattcata tgcttgagaa ga 22

<210> SEQ ID NO 78
<211> LENGTH: 22
<212> TYPE: DNA
<213> ORGANISM: Artificial Sequence
<220> FEATURE:
<223> OTHER INFORMATION: Synthetic sequence: Primer ARP2

<400> SEQUENCE: 78
gcctacaaaa aagctccgca cg 22

<210> SEQ ID NO 79
<211> LENGTH: 1366
<212> TYPE: DNA
<213> ORGANISM: Oryza sativa

<400> SEQUENCE: 79
gtcattcata tgcttgagaa gagagtcggg atagtccaaa ataaaacaaa ggtaagatta 60
cctggtcaaa agtgaaaaca tcagttaaaa ggtggtataa gtaaaatatc ggtaataaaa 120

-continued ggtggcccaa agtgaaattt actcttttct actattataa aaattgagga tgttttgtcg 180
gtactttgat acgtcatttt tgtatgaatt ggtttttaag tttattcgcg atttggaaat 240
gcatatctgt atttgagtcg gtttttaagt tcgttgcttt tgtaaataca gagggatttg 300
tataagaaat atctttaaaa aacccatatg ctaatttgac ataatttttg agaaaaatat 360
atattcaggc gaattccaca atgaacaata ataagattaa aatagcttgc cccgttgca 420 gcgatgggta ttttttctag taaaataaaa gataaactta gactcaaaac atttacaaaa 480
acaaccccta aagtcctaaa gcccaaagtg ctatgcacga tccatagcaa gcccagccca 540
acccaaccca acccaaccca ccccagtgca gccaactggc aaatagtctc cacccccggc 600
actatcaccg tgagttgtcc gcaccaccgc acgtctcgca gccaaaaaaa aaaaaagaaa 660
gaaaaaaaag aaaaagaaaa acagcaggtg ggtccgggtc gtgggggccg gaaaagcgag 720
gaggatcgcg agcagcgacg aggcccggcc ctccctccgc ttccaaagaa acgcccccca 780
tcgccactat atacataccc ccccctctcc tcccatcccc ccaaccctac caccaccacc 840
accaccacct cctcccccct cgctgccgga cgacgagctc ctccccccctc cccctccgcc 900 gccgccggta accaccccgc ccctctcctc tttctttctc cgtttttttt ttcgtctcgg 960
tctcgatctt tggccttggt agtttgggtg ggcgagagcg gcttcgtcgc ccagatcggt 1020
gcgcgggagg ggcgggatct cgcggctggc gtctccgggc gtgagtcggc ccggatcctc 1080
gcggggaatg gggctctcgg atgtagatct gcgatccgcc gttgttgggg gagatgatgg 1140
ggggtttaaa atttccgcca tgctaaacaa gatcaggaag aggggaaaag ggcactatgg 1200
tttatatttt tatatatttc tgctgcttcg tcaggcttag atgtgctaga tcttctttct 1260
ttcttctttt tgtggtagaa tttgaatccc tcagcattgt tcatcggtag tttttctttt 1320
catgatttgt gacaaatgca gcctcgtgcg gagctttttt gtaggc 1366

<210> SEQ ID NO 80
<211> LENGTH: 24
<212> TYPE: DNA
<213> ORGANISM: Artificial Sequence
<220> FEATURE:
<223> OTHER INFORMATION: Synthetic sequence: Primer AS548

<400> SEQUENCE: 80
acggtgaagt aagaccaagc tcat 24

<210> SEQ ID NO 81
<211> LENGTH: 25
<212> TYPE: DNA
<213> ORGANISM: Artificial Sequence
<220> FEATURE:
<223> OTHER INFORMATION: Synthetic sequence: Primer AS549

<400> SEQUENCE: 81
ctaggtcgga acaagttgat aggac 25

<210> SEQ ID NO 82
<211> LENGTH: 25
<212> TYPE: DNA
<213> ORGANISM: Artificial Sequence
<220> FEATURE:
<223> OTHER INFORMATION: Synthetic sequence: Primer AS550

<400> SEQUENCE: 82
ggctatgcca tcctaaggtg ctgct 25

<210> SEQ ID NO 83
<211> LENGTH: 27
<212> TYPE: DNA
<213> ORGANISM: Artificial Sequence
<220> FEATURE:
<223> OTHER INFORMATION: Synthetic sequence: Primer AS551

<400> SEQUENCE: 83
ccatgaatga taaatcatag atcgaac 27

<210> SEQ ID NO 84
<211> LENGTH: 21
<212> TYPE: DNA
<213> ORGANISM: Artificial Sequence
<220> FEATURE:
<223> OTHER INFORMATION: Synthetic sequence: Primer RC1

<400> SEQUENCE: 84
cctgacccga agatgtggat c 21

<210> SEQ ID NO 85
<211> LENGTH: 21
<212> TYPE: DNA
<213> ORGANISM: Artificial Sequence
<220> FEATURE:
<223> OTHER INFORMATION: Synthetic sequence: Primer RC2

<400> SEQUENCE: 85
acattagcat ggcgtactcc t 21

<210> SEQ ID NO 86
<211> LENGTH: 21
<212> TYPE: DNA
<213> ORGANISM: Artificial Sequence
<220> FEATURE:
<223> OTHER INFORMATION: Synthetic sequence: Primer RC3

<400> SEQUENCE: 86
aaccaggaac ggggagctct c 21

<210> SEQ ID NO 87
<211> LENGTH: 21
<212> TYPE: DNA
<213> ORGANISM: Artificial Sequence
<220> FEATURE:
<223> OTHER INFORMATION: Synthetic sequence: Primer RC4

<400> SEQUENCE: 87
cgactctttg atcttaaact t 21

<210> SEQ ID NO 88
<211> LENGTH: 20
<212> TYPE: DNA
<213> ORGANISM: Artificial Sequence
<220> FEATURE:
<223> OTHER INFORMATION: Synthetic sequence: Primer AS526

<400> SEQUENCE: 88
gagtcgatac ttcggcgatc 20

<210> SEQ ID NO 89
<211> LENGTH: 18
<212> TYPE: DNA
<213> ORGANISM: Artificial Sequence
<220> FEATURE:
<223> OTHER INFORMATION: Synthetic sequence: Primer AS527

-continued

```
<400> SEQUENCE: 89

aacgtcggtt cgagatgg                                              18


<210> SEQ ID NO 90
<211> LENGTH: 23
<212> TYPE: DNA
<213> ORGANISM: Artificial Sequence
<220> FEATURE:
<223> OTHER INFORMATION: Synthetic sequence: Primer AS528

<400> SEQUENCE: 90

ttaccagaca accattacct gtc                                        23


<210> SEQ ID NO 91
<211> LENGTH: 20
<212> TYPE: DNA
<213> ORGANISM: Artificial Sequence
<220> FEATURE:
<223> OTHER INFORMATION: Synthetic sequence: Primer AS529

<400> SEQUENCE: 91

gctgggatta cacatggcat                                            20


<210> SEQ ID NO 92
<211> LENGTH: 10
<212> TYPE: DNA
<213> ORGANISM: Artificial sequence
<220> FEATURE:
<223> OTHER INFORMATION: Synthetic sequence: Consensus sequence

<400> SEQUENCE: 92

atagaataaa                                                       10


<210> SEQ ID NO 93
<211> LENGTH: 195
<212> TYPE: DNA
<213> ORGANISM: Nicotiana tabacum

<400> SEQUENCE: 93

ctcgagacaa tggcttcctc agttctttcc tctgcagcag ttgccactcg caccaatgtt     60

gctcaagcta acatggttgc acctttcact ggtcttaagt cagctgcctc attccctgtt    120

tcaaggaagc aaaaccttga catcacttcc attgctagca atggtggaag agtgcaatgt    180

atgcaggtag catgc                                                    195
```